US012410487B2

(12) United States Patent
Soloveychik et al.

(10) Patent No.: US 12,410,487 B2
(45) **Date of Patent: *Sep. 9, 2025**

(54) SELECTIVE MODULATION OF PROTEIN-PROTEIN INTERACTIONS

(71) Applicant: SyntheX, Inc., San Francisco, CA (US)

(72) Inventors: Maria Soloveychik, San Francisco, CA (US); Charly Chahwan, San Francisco, CA (US)

(73) Assignee: SyntheX, Inc., San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/499,563

(22) Filed: Nov. 1, 2023

(65) Prior Publication Data

US 2024/0287626 A1 Aug. 29, 2024

Related U.S. Application Data

(63) Continuation of application No. 15/931,295, filed on May 13, 2020, now Pat. No. 11,840,743, which is a continuation of application No. PCT/US2018/061292, filed on Nov. 15, 2018.

(60) Provisional application No. 62/590,147, filed on Nov. 22, 2017, provisional application No. 62/587,269, filed on Nov. 16, 2017.

(51) Int. Cl.

| | |
|---|---|
| ***C12N 15/80*** | (2006.01) |
| ***C12N 15/10*** | (2006.01) |
| ***C12N 15/81*** | (2006.01) |
| ***C12Q 1/6897*** | (2018.01) |

(52) U.S. Cl.

CPC ....... *C12Q 1/6897* (2013.01); *C12N 15/1055* (2013.01); *C12N 15/1093* (2013.01); *C12N 15/80* (2013.01); *C12N 15/81* (2013.01); *C12N 15/815* (2013.01); *C12Q 2521/50* (2013.01); *C12Q 2600/158* (2013.01)

(58) Field of Classification Search

CPC ................................ C12N 15/10; C12N 15/81

See application file for complete search history.

(56) References Cited

U.S. PATENT DOCUMENTS

| | | | |
|---|---|---|---|
| 6,673,540 B1 | 1/2004 | Young et al. | |
| 11,840,743 B2 * | 12/2023 | Soloveychik .......... | C12N 15/10 |
| 2002/0004242 A1 | 1/2002 | Mcvey et al. | |
| 2004/0265791 A1 | 12/2004 | Tetsu et al. | |
| 2006/0223089 A1 | 10/2006 | Vidal et al. | |
| 2006/0292656 A1 | 12/2006 | Singh et al. | |
| 2008/0261819 A1 | 10/2008 | Lorens et al. | |
| 2009/0130676 A1 | 5/2009 | Brent et al. | |
| 2017/0010277 A1 | 1/2017 | Watanabe et al. | |
| 2017/0240883 A1 | 8/2017 | Christiansen et al. | |
| 2017/0266306 A1 | 9/2017 | Eckert et al. | |

FOREIGN PATENT DOCUMENTS

| | | |
|---|---|---|
| WO | WO-9849338 A1 | 11/1998 |
| WO | WO-2017031399 A1 | 2/2017 |
| WO | WO-2017053706 A1 | 3/2017 |
| WO | WO-2017075335 A1 | 5/2017 |
| WO | WO-2017205852 A2 | 11/2017 |
| WO | WO-2019099678 A1 | 5/2019 |

OTHER PUBLICATIONS

Akada et al. Screening and identification of yeast sequences that cause growth inhibition when overexpressed. Mol Gen Genet. Apr. 16, 1997;254(3):267-74. doi: 10.1007/s004380050415.

GenBank Accession No. ACQ65797 Version No. ACQ65797.1. prolyl oligopeptidase [Conocybe apala]. Record created May 9, 2009. 2 pages. Retrieved May 9, 2024 at URL: https://www.ncbi.nlm.nih.gov/protein/ACQ65797.1.

GenBank Accession No. ADN19205. Version No. ADN19205.1. prolyl oligopeptidase [Amanita bisporigera]. Record created Sep. 20, 2010. 1 page. Retrieved Jul. 30, 2020 at URL: https://www.ncbi.nlm.nih.gov/protein/ADN19205.1/.

GenBank Accession No. GAW09065. Version No. GAW09065.1. prolyl oligopeptidase [Lentinula edodes]. Record created Feb. 2, 2017. 2 pages. Retrieved Jul. 30, 2020 at URL: https://www.ncbi.nlm.nih.gov/protein/GAW09065.1/.

GenBank Accession No. GAW09067. Version No. GAW09067.1. tetrapyrrole methylase [Lentinula edodes]. Record created Feb. 2, 2017. 2 pages. Retrieved Jul. 30, 2020 at URL: https://www.ncbi.nlm.nih.gov/protein/GAW09067.1/.

GenBank Accession No. HQ225840. Version No. HQ225840.1. Amanita bisporigera prolyl oligopeptidase (POPA) mRNA, complete cds. Record created Sep. 20, 2010. 2 pages. Retrieved Jul. 30, 2020 at URL: https://www.ncbi.nlm.nih.gov/nuccore/HQ225840.1/.

GenBank Accession No. HQ225841. Version No. HQ225841.1. Amanita bisporigera prolyl oligopeptidase (POPB) mRNA, complete cds. Record created Sep. 20, 2010. 2 pages. Retrieved Jul. 30, 2020 at URL: https://www.ncbi.nlm.nih.gov/nuccore/HQ225841.1/.

GenBank Accession No. JN827313. Version No. JN827313.2. Galerina marginata prolyl oligopeptidase (POPA) mRNA, complete cds. Record created Jan. 10, 2012. 2 pages. Retrieved Jul. 30, 2020 at URL: https://www.ncbi.nlm.nih.gov/nuccore/JN827313.2/.

(Continued)

*Primary Examiner* — Tekchand Saidha

(74) *Attorney, Agent, or Firm* — Wilson Sonsini Goodrich & Rosati

(57) ABSTRACT

The present disclosure provides methods to identify peptides and small molecule moieties that are able to modulate protein-protein interactions (PPIs). Some moieties can disrupt specific PPIs within a complex, or disrupt variant-specific PPIs. Some moieties can alternatively bridge between two proteins in a protein-specific or a variant-specific manner. The methods described enable generation of compounds able to modulate PPI networks within cells with implications for drug development for pathological conditions.

16 Claims, 17 Drawing Sheets

Specification includes a Sequence Listing.

(56) References Cited

OTHER PUBLICATIONS

GenBank Accession No. JN827314. Version No. JN827314.2. Galerina marginata prolyl oligopeptidase (POPB) mRNA, complete cds. Record created Jan. 10, 2012. 2 pages. Retrieved Jul. 30, 2020 at URL: https://www.ncbi.nlm.nih.gov/nuccore/JN827314.2/.
GenBank Accession No. KDR68385. Version No. KDR68385.1. hypothetical protein GALMADRAFT_104945 [Galerina marginata CBS 339.88]. Record created Jun. 6, 2014. 2 pages. Retrieved Jul. 30, 2020 at URL: https://www.ncbi.nlm.nih.gov/protein/KDR68385.1.
GenBank Accession No. KDR68475. Version No. KDR68475.1. hypothetical protein GALMADRAFT_78538 [Galerina marginata CBS 339.88]. Record created Jun. 6, 2014. 2 pages. Retrieved Jul. 30, 2020 at URL: https://www.ncbi.nlm.nih.gov/protein/KDR68475.1/.
GenBank Accession No. KDR73903. Version No. KDR73903.1. hypothetical protein GALMADRAFT_141673 [Galerina marginata CBS 339.88]. Record created Jun. 6, 2014. 2 pages. Retrieved Jul. 30, 2020 at URL: https://www.ncbi.nlm.nih.gov/protein/KDR73903.1/.
GenBank Accession No. KDR74877. Version No. KDR74877.1. hypothetical protein GALMADRAFT_99137 [Galerina marginata CBS 339.88]. Record created Jun. 6, 2014. 2 pages. Retrieved Jul. 30, 2020 at URL: https://www.ncbi.nlm.nih.gov/protein/KDR74877.1/.
GenBank Accession No. KDR80488. Version No. KDR80488.1. hypothetical protein GALMADRAFT_136963 [Galerina marginata CBS 339.88]. Record created Jun. 6, 2014. 2 pages. Retrieved Jul. 30, 2020 at URL: https://www.ncbi.nlm.nih.gov/protein/KDR80488.1/.
GenBank Accession No. KDR84981. Version No. KDR84981.1. hypothetical protein GALMADRAFT_260690 [Galerina marginata CBS 339.88]. Record created Jun. 6, 2014. 2 pages. Retrieved Jul. 30, 2020 at URL: https://www.ncbi.nlm.nih.gov/protein/KDR84981.1/.
GenBank Accession No. KYQ30898 Version No. KYQ30898.1. Prolyl endopeptidase [Hypsizygus marmoreus]. Record created Mar. 31, 2016. 2 pages. Retrieved May 9, 2024 at URL: https://www.ncbi.nlm.nih.gov/protein/KYQ30898.1?report=genpept.
GenBank Accession No. KYQ37095 Version No. KYQ37095.1. hypothetical protein Hypma_08924 [Hypsizygus marmoreus]. Record created Mar. 31, 2016. 2 pages. Retrieved May 9, 2024 at https://www.ncbi.nlm.nih.gov/protein/KYQ37095.1?report=genpept.
GenBank Accession No. OAX31299. Version No. OAX31299.1. tetrapyrrole methylase [Rhizopogon vinicolor AM-OR11-026]. Record created Jun. 7, 2016. 1 page. Retrieved Jul. 30, 2020 at URL: https://www.ncbi.nlm.nih.gov/protein/OAX31299.1/.
GenBank Accession No. OAX32862. Version No. OAX32862.1. tetrapyrrole methylase [Rhizopogon vinicolor AM-OR11-026]. Record created Jun. 7, 2016. 1 page. Retrieved Jul. 30, 2020 at URL: https://www.ncbi.nlm.nih.gov/protein/OAX32862.1/.
GenBank Accession No. OAX32863. Version No. OAX32863.1. beta-lactamase/transpeptidase-like protein [Rhizopogon vinicolor AM-OR11-026]. Record created Jun. 7, 2016. 2 pages. Retrieved Jul. 30, 2020 at URL: https://www.ncbi.nlm.nih.gov/protein/OAX32863.1/.
GenBank Accession No. OAX34183. Version No. OAX34183.1. beta-lactamase/transpeptidase-like protein [Rhizopogon vinicolor AM-OR11-026]. Record created Jun. 7, 2016. 2 pages. Retrieved Jul. 30, 2020 at URL: https://www.ncbi.nlm.nih.gov/protein/OAX34183.1/.
GenBank Accession No. OAX34185. Version No. OAX34185.1. FAD/NAD(P)-binding domain-containing protein [Rhizopogon vinicolor AM-OR11-026]. Record created Jun. 7, 2016. 2 pages. Retrieved Jul. 30, 2020 at URL: https://www.ncbi.nlm.nih.gov/protein/OAX34185.1/.
GenBank Accession No. XP_567292. Version No. XP 567292. conserved hypothetical protein [Cryptococcus neoformans var. neoformans JEC21]. Record created Jan. 28, 2005. 2 pages. Retrieved Jul. 30, 2020 at URL: https://www.ncbi.nlm.nih.gov/protein/XP_567292.1/.
Kawahata et al., A positive selection for plasmid loss in *Saccharomyces cerevisiae* using galactose-inducible growth inhibitory sequences. Yeast 15(1):1-10 (1999).
Luo et al., Peptide macrocyclization catalyzed by a prolyl oligopeptidase involved in α-amanitin biosynthesis. Chemistry and Biology 21(12): 1610-1617 (2014).
PCT/US2018/061292 International Search Report and Written Opinion dated Feb. 5, 2019.
Pooggin et al., Role of a short open reading frame in ribosome shunt on the cauliflower mosaic virus RNA leader. Journal of Biological Chemistry 275(23):17288-17296 (2000).
Pulman et al. Expansion and diversification of the MSDIN family of cyclic peptide genes in the poisonous agarics Amanita phalloides and A. bisporigera. BMC Genomics. 2016; 17: 1038. Published online Dec. 15, 2016. doi: 10.1186/s12864-016-3378-7. 14 pages.
U.S. Appl. No. 15/931,295 Notice of Allowance dated Sep. 20, 2023.
U.S. Appl. No. 15/931,295 Office Action dated Jun. 9, 2023.
U.S. Appl. No. 15/931,295 Office Action dated Mar. 1, 2023.
U.S. Appl. No. 15/931,295 Office Action dated Nov. 3, 2022.
Varshavsky, 1996, The N-end rule: Functions, mysteries, uses. Proc. Nat. Acad. Sci. USA, 93:12142-12149.
Vidal et al. Prospects for drug screening using the reverse two-hybrid system. Tibtech, vol. 17, pp. 374-381 (Sep. 1999).

* cited by examiner

Disruption of specific complex components

Allele specific interaction disruption

Step 1.

Step 2.

Step 3.

Step 4.

SELECTIVE MODULATION OF PROTEIN-PROTEIN INTERACTIONS

CROSS-REFERENCE

This application is a continuation application of U.S. Non-Provisional application Ser. No. 15/931,295, filed May 13, 2020, which is a continuation application of International Application No. PCT/US2018/061292, filed Nov. 15, 2018, which claims the benefit of U.S. Provisional Application No. 62/587,269 titled SELECTIVE DISRUPTION OF PROTEIN-PROTEIN INTERACTIONS, filed on Nov. 16, 2017 and U.S. Provisional Application No. 62/590,147 titled CYCLIC AND BICYCLIC PEPTIDES AND METHODS OF MAKING AND USING THEREOF, filed on Nov. 22, 2017, which are incorporated herein by reference.

SEQUENCE LISTING

The instant application contains a Sequence Listing which has been submitted electronically in XML format and is hereby incorporated by reference in its entirety. Said XML file, created on Oct. 31, 2023, is named 50607-703_302_SL.xml and is 96,288 bytes in size.

BACKGROUND

Disruption of protein-protein interactions in a precise manner can be a key for controlling cellular functions. Many pathological conditions are characterized by aberrant functions of cellular pathways, either because of precocious protein complex formation or the incorporation of malfunctional variants. Thus, compounds that can specifically and precisely prevent the formation of such protein complexes or the malfunction of faulty variants could be beneficial to treating various ailments. The selective disruption of precise protein-protein interactions is difficult to achieve using the traditional enzyme active-site/inhibitor-based drug development scheme. Accordingly, there is a need for development of methods and compositions that target protein-protein interactions in precise and selective ways.

SUMMARY

Disclosed herein, in certain embodiments, is a method for identifying a molecule that selectively disrupts an interaction between a first test protein and a second test protein in a host cell, comprising: expressing in the host cell a first fusion protein comprising the first test protein and a DNA-binding moiety; expressing in the host cell a second fusion protein comprising the second test protein and a gene activating moiety; expressing in the host cell a third fusion protein comprising the third test protein and a different DNA-binding moiety; and delivering a molecule from a library to the host cell, wherein a sequence of gene for expressing a death agent is disposed within the host cell and operably linked a promoter DNA sequence specific for the DNA binding moiety of the first fusion protein, wherein a positive selection reporter is disposed within the host and operably linked to a promoter DNA sequence specific for the DNA binding moiety of the third fusion protein, and wherein, in the absence of the molecule, the interaction between the first test protein and the second test protein causes the gene activating moiety to activate expression of the death agent, while the interaction between the second test protein and the third test protein causes the gene activating moiety to activate the expression of the positive selection reporter. In some embodiments, the molecule from the library is delivered exogenously. In some embodiments, the host cell comprises more than one sequence for expressing a positive control reporter that is activated by a promoter DNA sequence specific for a DNA binding moiety. In some embodiments, the host cell comprises more than one sequence for expressing a death agent that is activated by a promoter DNA sequence specific for a DNA binding moiety. In some embodiments, the host cell comprises an integrated DNA encoding the first fusion protein, an integrated DNA encoding the second fusion protein, an integrated DNA encoding the third fusion protein; a plasmid DNA encoding the death agent; and a plasmid DNA encoding a positive selection reporter. In some embodiments, the first test protein is a variation of KRAS. In some embodiments, the third test protein is KRAS. In some embodiments, the second test protein is c-Raf. In some embodiments, the first test protein is YAP or TAZ. In some embodiments, the third test protein is VGLL4. In some embodiments, the second test protein is TEAD. In some embodiments, the DNA binding moiety is derived from LexA, cI, Gli-1, YY1, Glucocorticoid receptor, TetR, or Ume6. In some embodiments, the gene activating moiety is derived from VP16, GAL4, NF-κB, B42, BP64, VP64, or p65. In some embodiments, the death agent is an overexpressed product of genetic element selected from DNA or RNA. In some embodiments, the genetic element is a Growth Inhibitory (GIN) sequence such as GIN11. In some embodiments, the death agent is a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, or any combination thereof. In some embodiments, the death agent is Cholera toxin, SpvB toxin, CARDS toxin, SpyA Toxin, HopUl, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof. In some embodiments, the host cell is a fungus or bacteria. In some embodiments, the fungus is *Aspergillus*. In some embodiments, the fungus is *Pichia pastoris*. In some embodiments, the fungus is *S. cerevisiae*. In some embodiments, the molecule is small molecule. In some embodiments, the small molecule is peptidomimetic. In some embodiments, the molecule is peptide or protein. In some embodiments, the peptide or protein is derived from naturally occurring protein product. In certain embodiments, the peptide or protein is synthesized protein product. In some embodiments, the peptide or protein is product of recombinant genes. In some embodiments, the molecule is a peptide or protein expressed from test DNA molecule inserted into the host cell, wherein the test DNA molecule comprises DNA sequences that encodes polypeptides, forming the library. In some embodiments, the library comprises polypeptides 60 or fewer amino acids in length. In some embodiments, the DNA sequence encodes a 3'UTR of mRNA. In some embodiments, the 3'UTR is the 3'UTR of sORF1. In some embodiments, the polypeptides comprise a common N-terminal sequence of Methionine-Valine-Asparagine. In some embodiments, the polypeptides in the library are processed into cyclic or bicyclic peptides in the host cell.

Disclosed herein, in certain embodiments, is a plasmid vector, comprising the components of PLASMID 1, or any combination of the components of PLASMID 1. In some embodiments, the plasmid vector comprises a DNA sequence encoding a first polypeptide inserted in frame with Gal4-DNA binding domain ("DBD"), a DNA sequence encoding a second polypeptide inserted in frame with LexA-DBD, and a DNA sequence encoding a third polypeptide inserted in frame with Dof1-AD. In certain embodiments, a host cell comprises the plasmid vectors.

Disclosed herein, in certain embodiments, is a library of plasmid vectors, each plasmid vector comprising: a DNA sequence encoding a different peptide sequence operably linked to a first switchable promoter; a DNA sequence encoding a death agent under control of a second switchable promoter; and a DNA sequence encoding a positive selection reporter under control of a third switchable promoter. In some embodiments, the different peptide sequence encodes a common N-terminal stabilization sequence. In some embodiments, the DNA sequence encodes a mRNA sequence comprising a 3'UTR. In some embodiments, the different peptide sequence is 60 amino acids or fewer in length. In some embodiments, the different peptide sequences are random. In some embodiments, the different peptide sequences are pre-enriched for binding to a target. In some embodiments is a library of host cells, each comprises a library of the plasmid vectors.

Disclosed herein, in certain embodiments, is a host cell configured to express: a first fusion protein comprising a DNA-binding moiety; a second fusion protein comprising a gene activating moiety; a third fusion protein comprising a different DNA-binding moiety; a death agent, wherein the expression of the death agent is under control of a promoter DNA sequence specific for one of the DNA-binding moiety; a positive selection reporter, wherein the expression of the positive reporter is under control of a promoter DNA sequence specific for the other DNA-binding moiety; and a polypeptide of 60 or fewer amino acids, wherein the polypeptide modulates an interaction between the first test protein and the second test protein; wherein the host cell optionally has a mutant background enabling uptake of small molecules; and wherein the host cell optionally has a mutant background enabling increased transformation efficiency. In some embodiments, the polypeptide encodes an N-terminal sequence for peptide stabilization. In some embodiments, the polypeptide is an encoded product of an mRNA, wherein the mRNA comprises a 3'UTR. In some embodiments, the mRNA is an encoded product of a DNA molecule, wherein the DNA molecule is delivered into the host cell exogenously. In some embodiments, synthetic compound libraries can be tested. In some embodiments, the host cell is a eukaryote or a prokaryote. In some embodiments, the host cell is animal, plant, a fungus, or bacteria. In some embodiments, the host cell is a haploid yeast cell. In some embodiments, the host cell is a diploid yeast cell. In some embodiments, the diploid yeast cell is produced by mating a first host cell comprising DNA sequences encoding the first chimeric gene, the second chimeric gene, and the third chimeric gene, to a second host cell comprising DNA sequences encoding the death agent, positive selection reporter, and the mRNA comprising a nucleotide sequence encoding a polypeptide. In some embodiments, the fungus is *Aspergillus*. In some embodiments, the fungus is *Pichia pastoris*. In some embodiments, the fungus is *S. cerevisiae*. In some embodiments is a kit, comprising: the plasmid vector and the library of plasmid vectors.

Disclosed herein, in certain embodiments, is a method for identifying a molecule that selectively facilitates an interaction between a first test protein and a second test protein, comprising: expressing in the host cell a first fusion protein comprising the first test protein and a DNA-binding moiety; expressing in the host cell a second fusion protein comprising the second test protein and a gene activating moiety; expressing in the host cell a third fusion protein comprising the third test protein and a different DNA-binding moiety; and delivering a molecule from a library to the host cell such that the molecule forms a bridging interaction between the first test protein and the second test protein; wherein a sequence of a gene for expressing a death agent is disposed within the host cell and operably linked a promoter DNA sequence specific for the DNA binding moiety of the third fusion protein; wherein a positive selection reporter is disposed within the host cell and operably linked to a promoter DNA sequence specific for the DNA binding moiety of the first fusion protein; and wherein the first test protein and second test protein to form a functional transcription factor that activates expression of the death agent when the molecule from the library forms the bridging interaction. In some embodiments, the molecule from the library is delivered exogenously. In some embodiments, the host cell comprises more than one sequence for expressing a death agent that is activated by the promoter DNA sequence specific for a DNA binding moiety. In some embodiments, the host cell comprises more than one sequence for expressing a positive control reporter that is activated by a promoter DNA sequence specific for a DNA binding moiety. In some embodiments, the host cell comprises an integrated DNA encoding the first fusion protein, an integrated DNA encoding the second fusion protein, an integrated DNA encoding the third fusion protein; a plasmid DNA encoding the death agent; and a plasmid DNA encoding a positive selection reporter. In some embodiments, the DNA binding moiety is derived from LexA, cI, Gli-1, YY1, Glucocorticoid receptor, TetR, or Ume6. In some embodiments, the gene activating moiety is derived from VP16, Gal4, NF-κB, B42, BP64, VP64, or p65. In some embodiments, the death agent is a genetic element wherein overexpression of genetic material results in growth inhibition of the host cell. In some embodiments, the death agent is an overexpressed product of DNA. In some embodiments, the death agent is an overexpressed product of RNA. In some embodiments, the sequence of the gene for expressing the death agent is a Growth Inhibitory (GIN) sequence such as GIN11. In some embodiments, the death agent is a ribosomally encoded xenobiotic agent, a ribosomally-encoded poison, a ribosomally-encoded endogenous or exogenous gene that results in severe growth defects upon mild overexpression, a ribosomally-encoded recombinase that excises an essential gene for viability, a limiting factor involved in the synthesis of a toxic secondary metabolite, or any combination thereof. In some embodiments, the death agent is Cholera toxin, SpvB toxin, CARDS toxin, SpyA Toxin, HopUl, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof. In some embodiments, the first test protein is a variation of KRAS. In some embodiments, the third test protein is KRAS. In some embodiments, the second test protein is c-Raf. In some embodiments, the first test protein is YAP or TAZ. In some embodiments, the third test protein is VGLL4. In some embodiments, the second test protein is TEAD. In some embodiments, the molecule is small molecule. In some embodiments, the small molecule is peptidomimetic. In some embodiments, the molecule is peptide or protein. In some embodiments, the peptide or protein is derived from naturally occurring protein product. In some embodiments, the peptide or protein is synthesized protein product. In some embodiments, the peptide or protein is product of recombinant genes. In some embodiments, the peptide or protein is expressed product of test DNA molecule inserted into the host cell, wherein the test DNA molecule comprises of DNA sequences that encodes polypeptides, forming the library. In some embodiments, the library comprises of sixty or fewer amino acids. In some embodiments, the peptide or protein is a product of post-translational modification. In some embodiments, the post-translational modification includes cleavage. In some embodiments, the post-translational modification includes cyclization. In some embodiments, the post-translational modification includes bi-cyclization. In some embodiments, the cyclization comprises reacting with prolyl endopeptidase. In some embodiments, the cyclization comprises reacting with beta-lactamase. In some embodiments, the bicyclization comprises reacting with hydroxylase and dehydratase. In some embodiments, the bicyclization is formed by a tryptathionine bridge. In some embodiments, the post-translational modification includes methylation. In some embodiments, the methylation comprises reacting with N-methyltransferase. In some embodiments, the post-translational modification includes halogenation. In some embodiments, the post-translational modification includes glycosylation. In some embodiments, the post-translational modification includes acylation. In some embodiments, the post-translational modification includes phosphorylation. In some embodiments, the post-translational modification includes acetylation. In some embodiments, the test DNA molecule comprises of gene sequence expressing modifying enzyme. In some embodiments, the test DNA molecule comprises of a gene sequence expressing N-terminal sequence of methionine-valine-asparagine. In some embodiments, the test DNA molecule comprises of a gene sequence encoding a 3'UTR. In some embodiments, the 3'UTR is 3'UTR of sORF1. In some embodiments, the host cell is a eukaryote or a prokaryote. In some embodiments, the host cell is animal, plant, a fungus, or bacteria. In some embodiments, the fungus is *Aspergillus*. In some embodiments, the fungus is *Pichia pastoris*. In some embodiments, the fungus is *S. cerevisiae*.

Disclosed herein, in certain embodiments, is a method of identifying a molecule that selectively modulates a first test protein and a second test protein in a host cell, comprising: expressing in the host cell a first fusion protein comprising the first test protein and a second fusion protein comprising the second test protein; delivering a first molecule to the host cell; modifying the first molecule while in the host cell via a modifying enzyme; and allowing the first molecule to modulate the interaction between the first test protein and the second test protein, wherein the first molecule is a product of an encoded DNA sequence, wherein the first molecule comprises a library and one or more modifying enzymes, and wherein the one or more modifying enzymes modify the library. In some embodiments, the first molecule is a small molecule. In some embodiments, the small molecule is peptidomimetic. In some embodiments, the first molecule is peptide or protein. In certain embodiments, the peptide or protein is derived from naturally occurring protein product. In some embodiments, the peptide or protein is synthesized protein product. In some embodiments, the first molecule is encoded in the host cell. In some embodiments, the first molecule is delivered exogenously. In some embodiments, the one or more modifying enzymes cause cleavage of the library. In some embodiments, the one or more modifying enzymes cause cyclization of the library. In some embodiments, the one or more modifying enzymes cause bicyclization of the library. In some embodiments, the cyclization comprises reacting with prolyl endopeptidase. In some embodiments, the cyclization comprises reacting with beta-lactamase. In some embodiments, the bicyclization comprises reacting with hydroxylase and dehydratase. In some embodiments, the bicyclization comprises formation of a tryptathionine bridge. In some embodiments, the one or more modifying enzymes cause methylation. In some embodiments, the one or more modifying enzymes is a methyltransferase. In some embodiments, the one or more modifying enzyme is a halogenase. In some embodiments, the one or more modifying enzymes cause glycosylation. In some embodiments, the one or more modifying enzymes cause acylation. In some embodiments, the one or more modifying enzymes cause phosphorylation. In some embodiments, the one or more modifying enzymes cause acetylation. In some embodiments, the library comprises of sixty or fewer amino acids. In some embodiments, the first test protein is KRAS or a variation of KRAS. In some embodiments, the second test protein is c-Raf. In some embodiments, the first test protein is YAP, TAZ, or VGLL4. In some embodiments, the second test protein is TEAD. In some embodiments, the host cell is a eukaryote or a prokaryote. In some embodiments, the host cell is animal, plant, a fungus, or bacteria. In some embodiments, the fungus is *Aspergillus*. In some embodiments, the fungus is *Pichia pastoris*. In some embodiments, the fungus is *S. cerevisiae*.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A illustrates a case where a peptide is unable to disrupt the pairwise interaction of interest (A-C). FIG. 1B illustrates a case where a peptide is able to disrupt the pairwise interaction of interest (A-C) without disrupting another interaction (A-B).

FIG. 2A illustrates a case where a peptide is unable to disrupt the pairwise interaction of interest (A-B'). FIG. 2B illustrates a case where a peptide is able to disrupt the pairwise interaction of interest between one variant (B') and a protein (A) without disrupting the interaction between another variant (B) and the protein (A).

FIG. 3A shows a case where a peptide is able to bridge one variant (B) and a protein (A). FIG. 3B illustrates a case where a peptide is able to bridge the secondary variant (B') and a protein (A).

FIG. 4A illustrates a case where a peptide is unable to disrupt the pairwise interaction of interest. FIG. 4B illustrates a case where a peptide is able to disrupt the Prey and BaitMut interaction by acting on the Prey without disrupting the interaction between BaitWT and Prey.

FIG. 5A illustrates a case where a peptide is unable to disrupt the pairwise interaction of interest. FIG. 5B illustrates a case where a peptide disrupts the Prey-BaitMut interaction by acting on the BaitMut without disrupting the interaction between BaitWT and Prey.

DETAILED DESCRIPTION

Figure 1A:
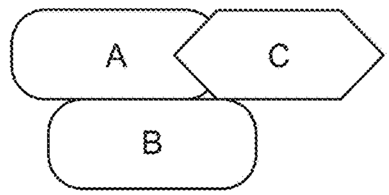
FIGS. 1A and 1B illustrate a platform to identify a compound that specifically disrupts a protein-protein interaction.
Figure 1A:
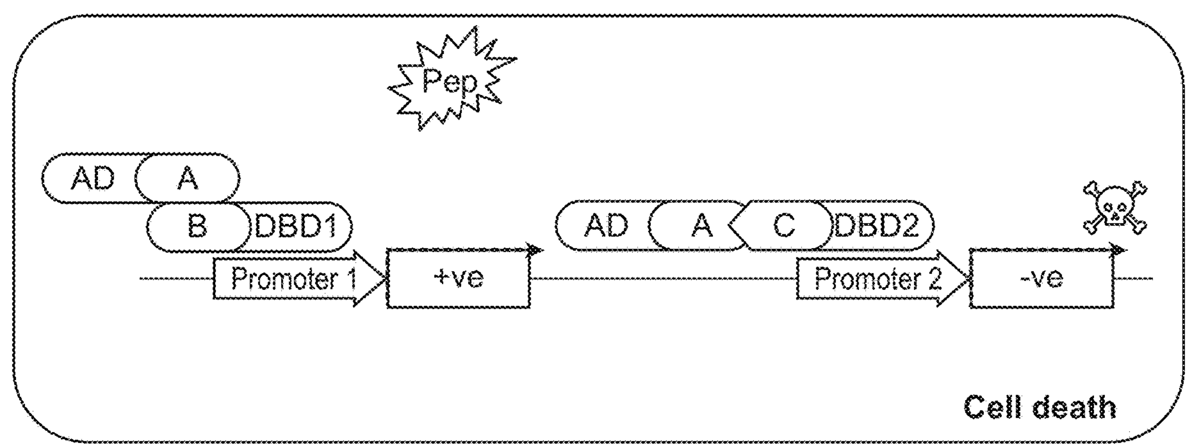

Two-hybrid screening can be used to identify and characterize protein-protein interactions. The two-hybrid system was initially developed using yeast as a host organism. However, bacterial or animal cell two-hybrid systems can also be used to characterize protein-protein interactions. The present disclosure provides a system that can use a unified eukaryotic or prokaryotic two-hybrid system in which bait and prey expression plasmid is used in both organismal contexts. Additionally, an extensive series of leucine zipper fusion proteins of known affinities can be generated to compare the efficiency of interaction detection using both systems. The yeast system can produce a quantitative readout over a dynamic range. "Auto-activation" by baits can be less prevalent in the bacterial system. In addition, modified expression vectors disclosed herein can be used for expression of a protein of interest in both eukaryotes and prokaryotes.

Three-hybrid systems rely on similar principles as two-hybrid systems, but involve an additional factor to bridge a protein-protein interaction to result in a gene expression readout.

The present disclosure also provides a system for delivering molecules across the cell membrane. The cell membrane presents a major challenge in drug discovery, especially for biologics such as peptides, proteins, and nucleic acids. One potential strategy to subvert the membrane barrier and deliver biologics into cells is to attach them to "cell penetrating peptides" (CPPs). Despite three decades of investigation, the fundamental basis for CPP activity remains elusive. CPPs that enter cells via endocytosis generally exit from endocytic vesicles in order to reach the cytosol. Unfortunately, the endosomal membrane has proven to be a significant barrier towards cytoplasmic delivery of these CPPs such that often a negligible fraction of the peptides escapes into the cell interior. What are thus needed are new scaffolds and structures that impart peptides with highly proficient intrinsic cell penetrating ability to various cell types. Several naturally occurring polyketides and peptides exhibit remarkable cell permeability (e.g. cyclosporine and amanitins). These peptides are characterized by specific modifications (e.g., N-methylation of the backbone and cyclization) that can play a crucial role in their cell membrane permeability. The compositions and methods disclosed herein describe methods and approaches that enable the general utilization of similar modifications to generate compositions that may be of high therapeutic value and that may be capable of disrupting select protein-protein interactions with high selectivity.

Definitions

As used herein, "reporter gene" refers to a gene whose expression can be assayed. Such genes include, for example, LacZ, β-glucuronidase (GUS), amino acid biosynthetic genes, the yeast LEU2, HIS3, LYS2, or URA3 genes, nucleic acid biosynthetic genes, the mammalian chloramphenicol transacetylase (CAT) gene, the green fluorescent protein (GFP) or any surface antigen gene for which specific antibodies are available. Reporter genes can result in both positive and negative selection.

An "allele" refers to a DNA sequence of a gene which includes a naturally occurring, or pathogenic variant of a gene. Expression of differing alleles may lead to different protein variants.

A "promoter" is a DNA sequence located proximal to the start of transcription at the 5' end of an operably linked transcribed sequence. The promoter can contain one or more regulatory elements or modules, which interact in modulating transcription of the operably linked gene. Promoters can be switchable or constitutive. Switchable promoters allow for reversible induction or repression of operably linked target genes upon administration of an agent. Examples of switchable promoters include but are not limited to the LexA operator and the alcohol dehydrogenase I (alcA) gene promoter. Examples of constitutive promoters include the human beta-actin gene promoter.

"Operably linked" describes two macromolecular elements arranged such that modulating the activity of the first element induces an effect on the second element. In this manner, modulation of the activity of a promoter element can be used to alter or regulate the expression of an operably-linked coding sequence. For example, the transcription of a coding sequence that is operably-linked to a promoter element can be induced by factors that activate the promoter's activity; transcription of a coding sequence that is operably-linked to a promoter element can be inhibited by factors that repress the promoter's activity. Thus, a promoter region is operably-linked to the coding sequence of a protein if transcription of such coding sequence activity is influenced by the activity of the promoter.

"In frame" as used herein throughout, refers to the proper positioning of a desired sequence of nucleotides within a DNA fragment or coding sequence operably linked to a promoter sequence, thereby permitting transcription and/or translation.

"Fusion construct" refers to recombinant genes that encode fusion proteins.

A "fusion protein" is a hybrid protein, i.e., a protein that has been constructed to contain domains from at least two different proteins. Fusion proteins described herein can be a hybrid proteins that possess both (1) a transcriptional regulatory domain from a transcriptional regulatory protein or a DNA binding domain from a DNA binding protein and (2) a heterologous protein to be assayed for interaction status. The protein that is the source of the transcriptional regulatory domain may different from the protein that is the source of the DNA binding domain. In other words, the two domains may be heterologous to each other.

A transcriptional regulatory domain of a prey fusion protein can either activate or repress transcription of target genes, depending on the biological activity of the domain. Bait proteins of the disclosure may also be fusion proteins, where the fusion protein is encoded by a fusion gene that can encodes for a protein of interest that is operably linked to a DNA binding moiety.

"Bridging interaction" refers to an interaction between a first protein and a second that occurs only when one or both of the first protein and the second protein interact with a molecule, such as a peptide or small molecule from a library. In some cases, the bridging interaction between the first protein and the second protein is direct, while in other cases the bridging interaction between the first protein and the second protein is indirect.

"Expression" is the process by which the information encoded within a gene is revealed. If the gene encodes a protein, then expression involves both transcription of the DNA into mRNA, the processing of mRNA (if necessary) into a mature mRNA product, and translation of the mature mRNA into protein.

As used herein, a "cloning vehicle" is any entity that is capable of delivering a nucleic acid sequence into a host cell for cloning purposes. Examples of cloning vehicles include plasmids or phage genomes. A plasmid that can replicate autonomously in the host cell is especially desired. Alternatively, a nucleic acid molecule that can insert (integrate) into the host cell's chromosomal DNA is useful, especially a molecule that inserts into the host cell's chromosomal DNA in a stable manner, that is, a manner that allows such molecule to be inherited by daughter cells.

Cloning vehicles are often characterized by one or a small number of endonuclease recognition sites at which such DNA sequences may be cut in a determinable fashion without loss of an essential biological function of the vehicle, and into which DNA may be spliced in order to bring about its replication and cloning.

The cloning vehicle can further contain a marker suitable for use in the identification of cells transformed with the cloning vehicle. For example, a marker gene can be a gene that confers resistance to a specific antibiotic on a host cell.

The word "vector" can be used interchangeably with "cloning vehicle."

As used herein, an "expression vehicle" is a vehicle or vector similar to the cloning vehicle that is especially designed to provide an environment that allows the expression of the cloned gene after transformation into the host. One manner of providing such an environment is to include transcriptional and translational regulatory sequences on such expression vehicles, such transcriptional and translational regulatory sequences being capable of being operably linked to the cloned gene. Another manner of providing such an environment is to provide a cloning site or sites on such vehicle, wherein a desired cloned gene and a desired expression regulatory element can be cloned.

In an expression vehicle, the gene to be cloned is usually operably-linked to certain control sequences such as promoter sequences. Expression control sequences will vary depending on whether the vector is designed to express the operably-linked gene in a prokaryotic or eukaryotic host and can additionally contain transcriptional elements such as enhancer elements, termination sequences, tissue-specificity elements, or translational initiation and termination sites.

A "host" refers to any organism that is the recipient of a cloning or expression vehicle. The host may be a yeast cell or a cultured animal cell such as a mammalian or insect cell. The yeast host may be *Saccharomyces cerevisiae*.

A "host cell" as described herein can be a bacterial, fungal, or mammalian cell or from an insect or plant. Examples of bacterial host cells are *E. coli* and *B. subtilis*. Examples of fungal cells are *S. cerevisiae* and *S. pombe*. Non-limiting examples of mammalian cells are immortalized mammalian cell lines, such as HEK293, A549, HeLa, or CHO cells, or isolated patient primary tissue cells that have been genetically immortalized (such as by transfection with hTERT). Non-limiting example of the plant is *Nicotiana tabacum* or *Physcomitrella patens*. A non-limiting example of insect cell is a sf9 (*Spodoptera frugiperda*) cell.

A "DNA-binding domain (DBD)," or a "DNA-binding moiety" is a moiety that is capable of directing specific polypeptide binding to a particular DNA sequence (i.e., a "protein binding site"). These proteins can be homodimers or monomers that bind DNA in a sequence specific manner. Exemplary DNA-binding domains of the disclosure include LexA, cI, glucocorticoid receptor binding domains, and the Ume6 domain.

A "gene activating moiety" or "activation domain" ("AD") is a moiety that is capable of inducing (albeit in many instances weakly inducing) the expression of a gene to whose control region it is bound (one example is an activation domain from a transcription factor). As used herein, "weakly" is meant below the level of activation effected by GAL4 activation region II and is preferably at or below the level of activation effected by the B42 activation domain. Levels of activation can be measured using any downstream reporter gene system and comparing, in parallel assays, the level of expression stimulated by the GAL4 region II-polypeptide with the level of expression stimulated by the polypeptide to be tested.

Screening for Disruptors to a Protein-Protein Interaction (PPI)

The often large and broad surfaces that can form the contact interface between two proteins can be potential targets of canonical small molecule inhibitors. However, the large and broad surfaces can have size limitations, and evolved resistance can occur readily. The specificity of antibodies can be combined with cell permeability in the form of short peptides, for example, peptides of less than 25 residues. Screening for short peptide disruptors of protein-protein interactions (PPIs) can be performed using technologies such as phage display or mRNA display. However, these screens are performed in vitro and require the purification of one of the interacting proteins of interest. Upon selection of a peptide sequence with affinity toward one of the proteins, secondary screens can be performed to validate that the peptide interferes with the binding interface of the second protein. This secondary screening can further rely upon the proper folding of the proteins and the replication of intracellular biophysical conditions in the assays.

Methods and systems of the disclosure can involve the intracellular selection of peptide disruptors of PPIs. Stated differently, various systems described herein can be used to screen for molecules that selectively disrupt an interaction between two proteins. A model organism, for example *Saccharomyces cerevisiae*, can be employed, and the coexpression of a PPI of interest with a test DNA molecule comprising a DNA sequence that encodes a randomized peptide library can allow for the selection of unbiased peptides that interfere with a specific PPI using selection mechanisms (e.g., a stringent viability readout selection mechanisms). The method can involve a permutation of a yeast two-hybrid system that can rely on the reconstitution of a transcription factor that requires an interaction between one or two test proteins fused to one or two DNA binding domain(s) (DBDs) and a second test protein fused to a transcription activation domain (AD) or gene activating moiety.

Methods and systems of the disclosure can use the reconstitution of a transcription factor mediated by the interaction between a protein fused to an AD, for example, VP16, NF-κB AD, VP64AD, BP64 AD, B42 acidic activation domain (B42AD), or p65 transactivation domain (p65AD) and another protein fused to a DBD, for example, LexA, cI, Gli-1, YY1, glucocorticoid receptor binding domain, or Ume6 domain.

Methods and system of the disclosure can also use two different proteins, or two variants of one protein, fused to different DBDs. These proteins may interact with the same protein fused to an AD to drive two different or identical reporters. The system can identify inhibitors against a specific PPI in a complex without affecting the rest of the complex integrity (see FIGS. 1A and 1B). This system can also be used to identify selective inhibitors that disrupt a PPI between a specific isoform and its binding partner without affecting another variant (see FIGS. 2A and 2B).

An efficient interaction between the two proteins of interest can direct RNA polymerase to a specific genomic site, and allow for the expression of a genetic element. The genetic element can be, for example, a gene that encodes a protein that enables an organism to grow on selection media. The selection media can be specific to, for example, ADE2, URA3, TRP1, KANR, or NATR, and will lack the essential component (Ade, Ura, Trp) or include a drug (G418, NAT). Markers that can detect when an interaction is no longer present (for example when the interaction is disrupted by an external composition) can be referred to as counter-selection markers, such as the URA3 gene, and can be poor or leaky (easily masked by the selection of mutants that escape the selection). This leakiness of the selection marker can lead to a high false positive rate.

Methods and systems of the disclosure can combine a strong negative selection marker with the intracellular stabilization of the production of short peptides to screen for blockers of PPIs. An inducible two-hybrid approach can be employed, which can drive the expression of any one or combination of several cytotoxic reporters (death agents) as well as positive selection markers. A method of the disclosure involving induced expression of a combination of cytotoxic reporters in a two-hybrid system can allow for a multiplicative effect in lowering the false-positive rate of the two-hybrid assay, as all of the cytotoxic reporters must simultaneously be "leaky" to allow for an induced cell to survive.

Disclosed herein, in certain embodiments, is a method for identifying a molecule that selectively disrupts an interaction between a first test protein and a second test protein in a host cell, comprising: expressing in the host cell a first fusion protein comprising the first test protein and a DNA-binding moiety; expressing in the host cell a second fusion protein comprising the second test protein and a gene activating moiety; expressing in the host cell a third fusion protein comprising the third test protein and a different DNA-binding moiety; and delivering a molecule from a library to the host cell; wherein a sequence of gene for expressing a death agent is disposed within the host cell and operably linked a promoter DNA sequence specific for the DNA binding moiety of the first fusion protein, wherein a positive selection reporter is disposed within the host and operably linked to a promoter DNA sequence specific for the DNA binding moiety of the third fusion protein, wherein, in the absence of the molecule, the interaction between the first test protein and the second test protein causes the gene activating moiety to activate expression of the death agent, while the interaction between the second test protein and the third test protein causes the gene activating moiety to activate the expression of the positive selection reporter.

Figure 1B:
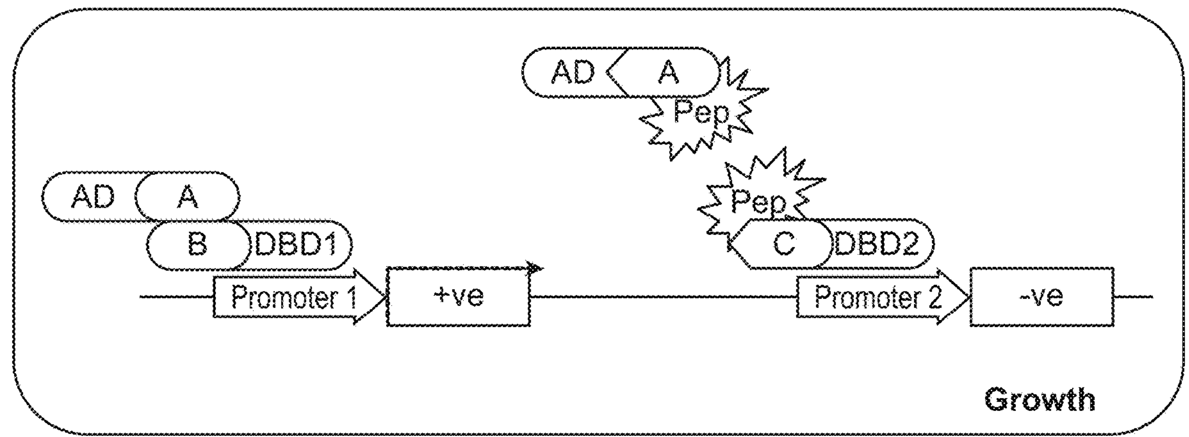

FIGS. 1A and 1B show a platform to identify a compound that disrupts a protein-protein interaction within a complex in a specific manner. DBD1 and DBD2 are promoter specific DNA-binding domains. AD refers to an activation domain. A, B, and C refer to three proteins, wherein B and C each interact with A. Broken arrows indicate active expression of the reporter. +ve refers to positive selection markers, −ve refers to death agents (negative selection markers). Pep refers to a peptide, such as a peptide from a library. In some embodiments, a peptide library may be replaced with a library that includes compounds other than peptides like small molecules. In some embodiments, the small molecules are peptidomimetics. Two scenarios are shown; FIG. 1A illustrates a case where a peptide (e.g., a peptide from a library) is unable to disrupt the pairwise interaction of interest (A-C), and a death agent is expressed, leading to cell death. FIG. 1B illustrates a case where a peptide (e.g., a peptide from a library) is able to disrupt the pairwise interaction of interest (A-C) without disrupting the A-B interaction. Selective peptide disruption activity is assayed by survival due to (1) the absence of expression of the death agent and (2) expression of the positive selection reporter (which provides evidence of selectivity).

Figure 2A:
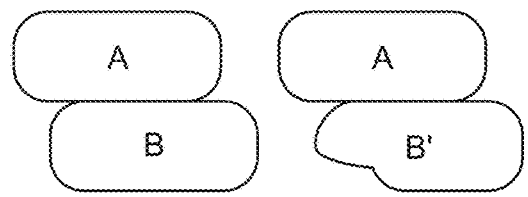
FIGS. 2A and 2B illustrate a platform to identify a compound that disrupts a protein-protein interaction (A-B') in a variant-specific manner.
Figure 2A:
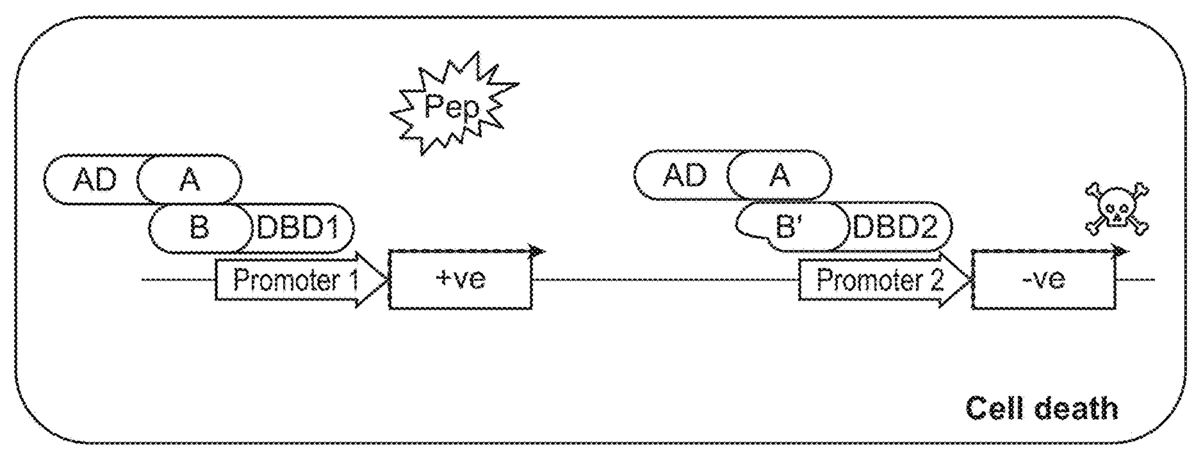
Figure 2B:
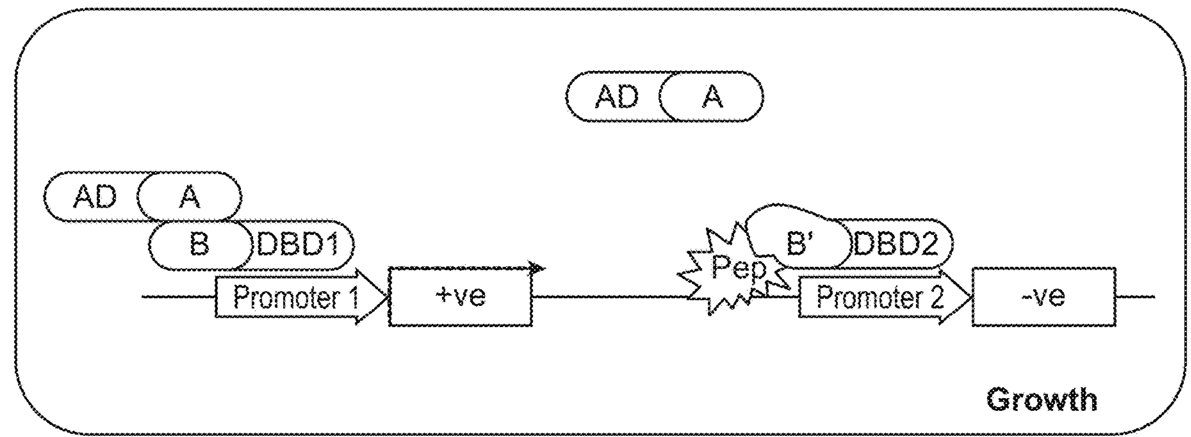

FIGS. 2A and 2B show a platform to identify a compound that disrupts a protein-protein interaction in a variant-specific manner. In other words, in contrast to FIGS. 1A and 1B in which B and C were unrelated protein, FIGS. 2A and 2B describe an analogous assay in which B and B' are related (but different) proteins (e.g., protein variants). As in FIGS. 1A and 1B, DBD1 and DBD2 are promoter-specific DNA-binding domains. AD refers to an activation domain. A, B, and B' refer to three proteins, wherein B and B' are two variants that are configured to interact with A. Broken arrows indicate active expression of the reporter. +ve refers to a positive selection marker, while −ve refers to a death agent. Pep refers to a peptide. Two scenarios are shown; FIG. 2A illustrates a case where a peptide is unable to disrupt the pairwise interaction of interest (A-B'), and a death is expressed, leading to cell death. FIG. 2B illustrates a case where a peptide is able to disrupt the pairwise interaction between A and B' without disrupting the interaction between the A and B. Selective peptides disruption is assayed by survival due to (1) the absence of expression of the death agent and (2) and expression of the positive selection reporter (which provides evidence of selectivity).

Screening for Facilitators to Protein-Protein Interaction

The system can additionally be used to screen for molecules that "bridge" an interaction between two proteins in a selective manner. In some embodiments, the system can be used to identify molecules which can bind to one isoform, or one protein, and bridge its interaction with another macromolecule, such as a protein, RNA, or DNA. For example, the bridging could occur to link the protein to an E3 ligase to mediate its degradation. For example, bridging can occur between an oncogenic protein such as K-Ras oncogenic alleles, Cyclin D family, Cyclin E family, c-MYC, EGFR, HER2, PDGFR, Raf kinase, VEGF and beta-catenin, or oncogenic variants such as IDH1(R132H, R132S, R132C, R132G, and R132L) or IDH2(R140Q, R172K), and an E3 ligase. An E3 ligase can be chosen from a list including, but not limited to, Cereblon, Skp2, MDM2, FBXW7, DCAF15, VHL, AMFR, ANAPC11, ANKIB1, AREL1, ARIH1, ARIH2, BARD1, BFAR, BIRC2, BIRC3, BIRC7, BIRC8, BMI1, BRAP, BRCA1, CBL, CBLB, CBLC, CBLL1, CCDC36, CCNB1IP1, CGRRF1, CHFR, CNOT4, CUL9, CYHR1, DCST1, DTX1, DTX2, DTX3, DTX3L, DTX4, DZIP3, E4F1, FANCL, G2E3, HACE1, HECTD1, HECTD2, HECTD3, HECTD4, HECW1, HECW2, HERC1, HERC2, HERC3, HERC4, HERC5, HERC6, HLTF, HUWE1, IRF2BP1, IRF2BP2, IRF2BPL, Itch, KCMF1, KMT2C, KMT2D, LNX1, LNX2, LONRF1, LONRF2, LONRF3, LRSAM1, LTN1, MAEA, MAP3K1, MARCH1, MARCH10, MARCH11, MARCH2, MARCH3, MARCH4, MARCH5, MARCH6, MARCH7, MARCH8, MARCH9, MDM4, MECOM, MEX3A, MEX3B, MEX3C, MEX3D, MGRN1, MIB1, MIB2, MID1, MID2, MKRN1, MKRN2, MKRN3, MKRN4P, MNAT1, MSL2, MUL1, MYCBP2, MYLIP, NEDD4, NEDD4L, NEURL1, NEURL1B, NEURL3, NFX1, NFXL1, NHLRC1, NOSIP, NSMCE1, PARK2, PCGF1, PCGF2, PCGF3, PCGF5, PCGF6, PDZRN3, PDZRN4, PELI1, PELI2, PELI3, PEX10, PEX12, PEX2, PHF7, PHRF1, PJA1, PJA2, PLAG1, PLAGL1, PML, PPIL2, PRPF19, RAD18, RAG1, RAPSN, RBBP6, RBCK1, RBX1, RC3H1, RC3H2, RCHY1, RFFL, RFPL1, RFPL2, RFPL3, RFPL4A, RFPL4AL1, RFPL4B, RFWD2, RFWD3, RING1, RLF, RLIM, RMND5A, RMND5B, RNF10, RNF103, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, RSPRY1, SCAF11, SH3RF1, SH3RF2, SH3RF3, SHPRH, SIAH1, SIAH2, SIAH3, SMURF1, SMURF2, STUB1, SYVN1, TMEM129, TOPORS, TRAF2, TRAF3, TRAF4, TRAF5, TRAF6, TRAF7, TRAIP, TRIM10 TRIM11 TRIM13 TRIM15 TRIM17 TRIM2 TRIM21 TRIM22 TRIM23 TRIM24 TRIM25 TRIM26, TRIM27, TRIM28, TRIM3, TRIM31, TRIM32, TRIM33, TRIM34, TRIM35, TRIM36, TRIM37 TRIM38 TRIM39 TRIM4 TRIM40 TRIM41 TRIM42 TRIM43 TRIM43B TRIM45 TRIM46, TRIM47, TRIM48, TRIM49, TRIM49B, TRIM49C, TRIM49D1, TRIM5, TRIM50, TRIM51, TRIM52, TRIM54, TRIM55, TRIM56, TRIM58, TRIM59, TRIM6, TRIM60, TRIM61, TRIM62, TRIM63, TRIM64, TRIM64B, TRIM64C, TRIM65, TRIM67, TRIM68, TRIM69, TRIM7, TRIM71, TRIM72, TRIM73, TRIM74, TRIM75P, TRIM77, TRIM8, TRIM9, TRIML1, TRIML2, TRIP12, TTC3, UBE3A, UBE3B, UBE3C, UBE3D, UBE4A, UBE4B, UBOX5, UBR1, UBR2, UBR3, UBR4, UBR5, UBR7, UHRF1, UHRF2, UNK, UNKL, VPS11, VPS18, VPS41, VPS8, WDR59, WDSUB1, WWP1, WWP2, XIAP, ZBTB12, ZFP91, ZFPL1, ZNF280A, ZNF341, ZNF511, ZNF521, ZNF598, ZNF645, ZNRF1, ZNRF2, ZNRF3, ZNRF4, Zswim2, and ZXDC. The peptide-mediated bridging event can be specific to a mutant variant, or to one member of a complex, without disrupting the integrity of the WT variant or the rest of the complex.

Disclosed herein, in certain embodiments, is a method for identifying a molecule that selectively facilitates an interaction between a first test protein and a second test protein comprising: expressing in the host cell a first fusion protein comprising the first test protein and a DNA-binding moiety; expressing in the host cell a second fusion protein comprising the second test protein and a gene activating moiety; expressing in the host cell a third fusion protein comprising the third test protein and a different DNA-binding moiety; and delivering a molecule from a library to the host cell such that the molecule forms a bridging interaction between the first test protein and the second test protein; wherein a sequence of a gene for expressing a death agent is disposed within the host cell and operably linked a promoter DNA sequence specific for the DNA binding moiety of the third fusion protein; wherein a positive selection reporter is disposed within the host cell and operably linked to a promoter DNA sequence specific for the DNA binding moiety of the first fusion protein; and wherein the first test protein and second test protein to form a functional transcription factor that activates expression of the death agent when the molecule from the library forms the bridging interaction.

Figure 3A:
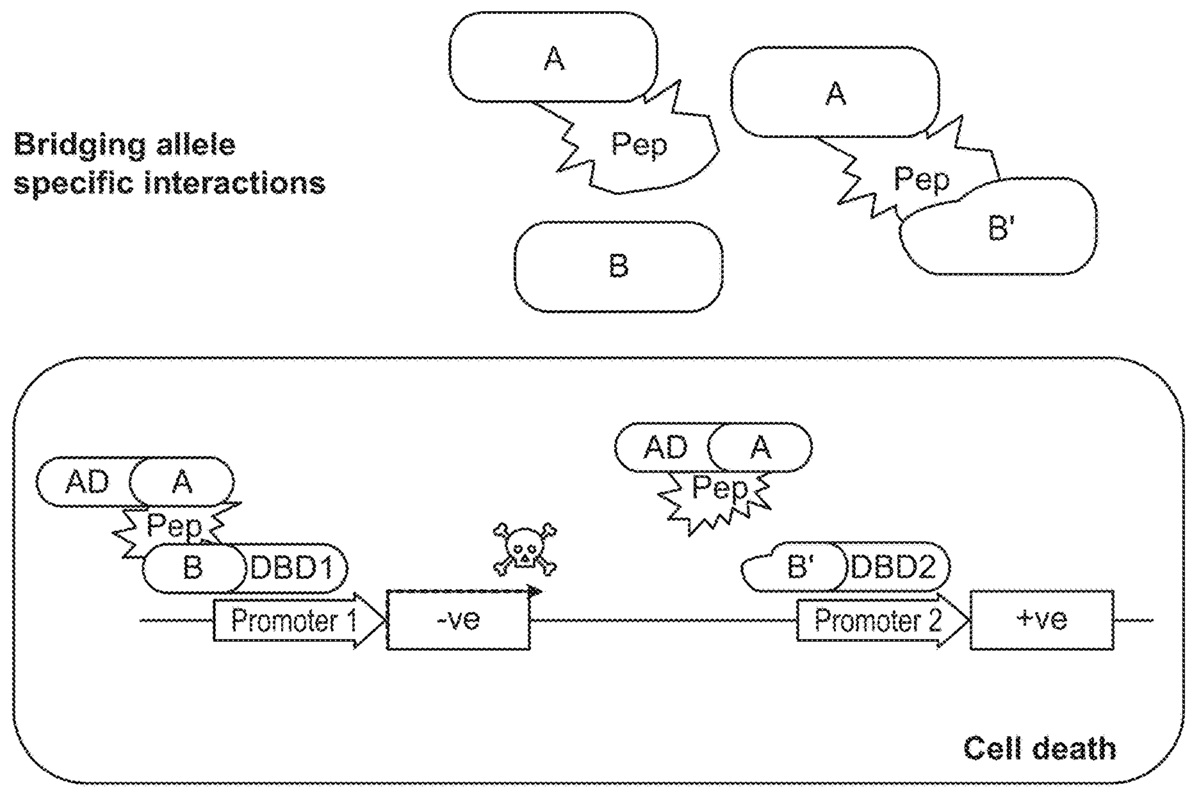
FIGS. 3A and 3B exemplify an embodiment of a platform to identify a compound that bridges two proteins in a variant- or protein-specific manner.
Figure 3B:
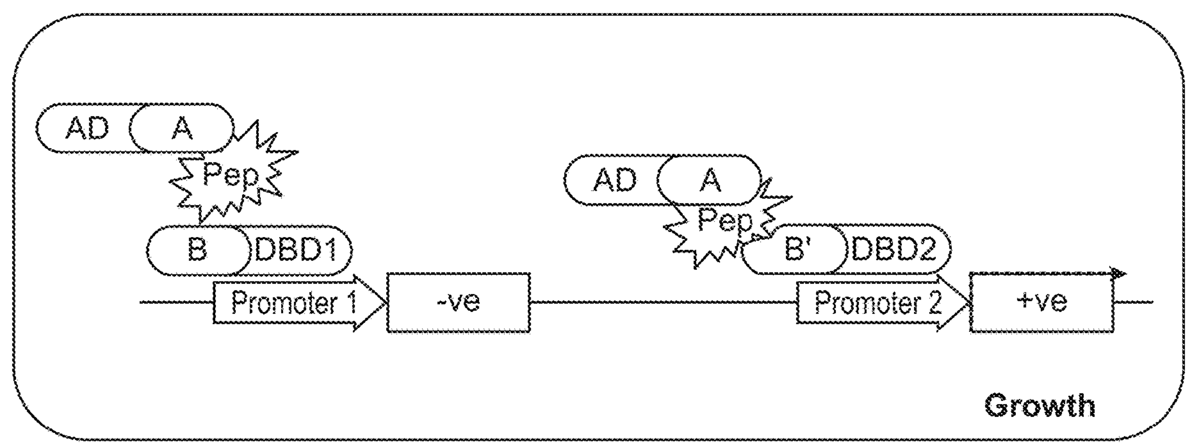

FIGS. 3A and 3B show a platform to identify a compound that bridges a protein-protein interaction in a variant- or protein-specific manner. DBD1 and DBD2 are promoter specific DNA-binding domains. AD refers to an activation domain. A, B, and B' refer to three proteins, wherein B and B' are two variants to be assayed for interaction with A. Broken arrows indicate active expression of the reporter. +ve refers to positive selection markers, −ve refers to death agents. Pep refers to a peptide (e.g., a peptide from a library). Two scenarios are shown; FIG. 3A illustrates a case where a peptide is able to bridge an interaction between one variant (B) and a protein (A). In this case, this is the control variant (B) and it leads to expression of the death and cell death. FIG. 3B illustrates a case where a peptide is able to bridge the secondary variant (B') and a protein (A). In this case, the peptide is bridging the variant of interest (B') and enables its binding to protein A. This combination of results leads to (1) the activation of a positive selection marker and (2) the lack of activation of the death agent (due to the lack of bridging to the unintended variant).

In some embodiments, the host cell disclosed herein further comprises an integrated DNA encoding the first fusion protein, an integrated DNA encoding the second fusion protein, an integrated DNA encoding the third fusion protein; a plasmid DNA encoding the death agent; and a plasmid DNA encoding a positive selection reporter.

Figure 8:
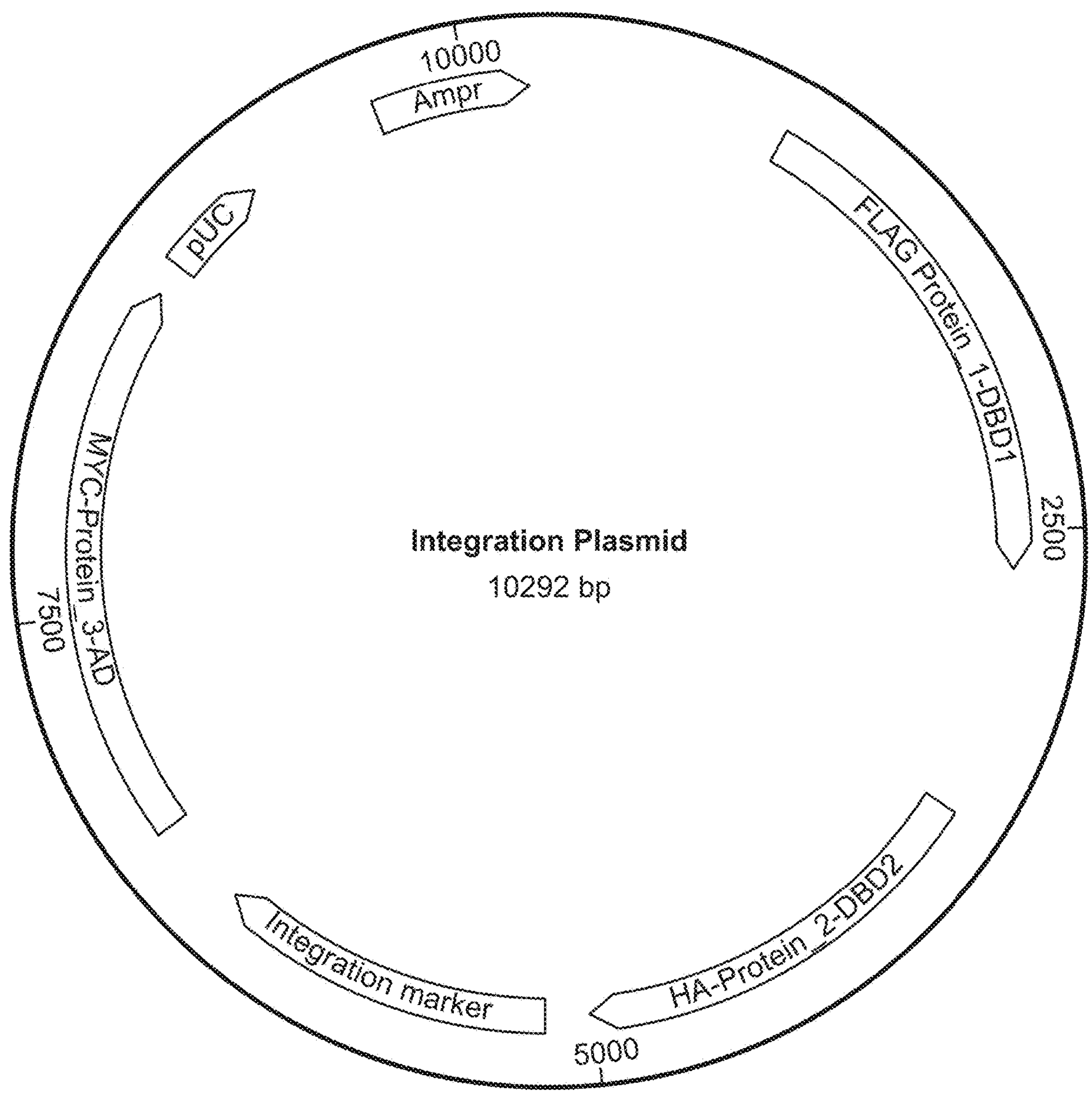
FIG. 8 shows an embodiment of an integration plasmid that encodes two bait proteins, each with its own DNA binding domain ("DBD"), and a prey protein with an activation domain ("AD").
Figure 9:
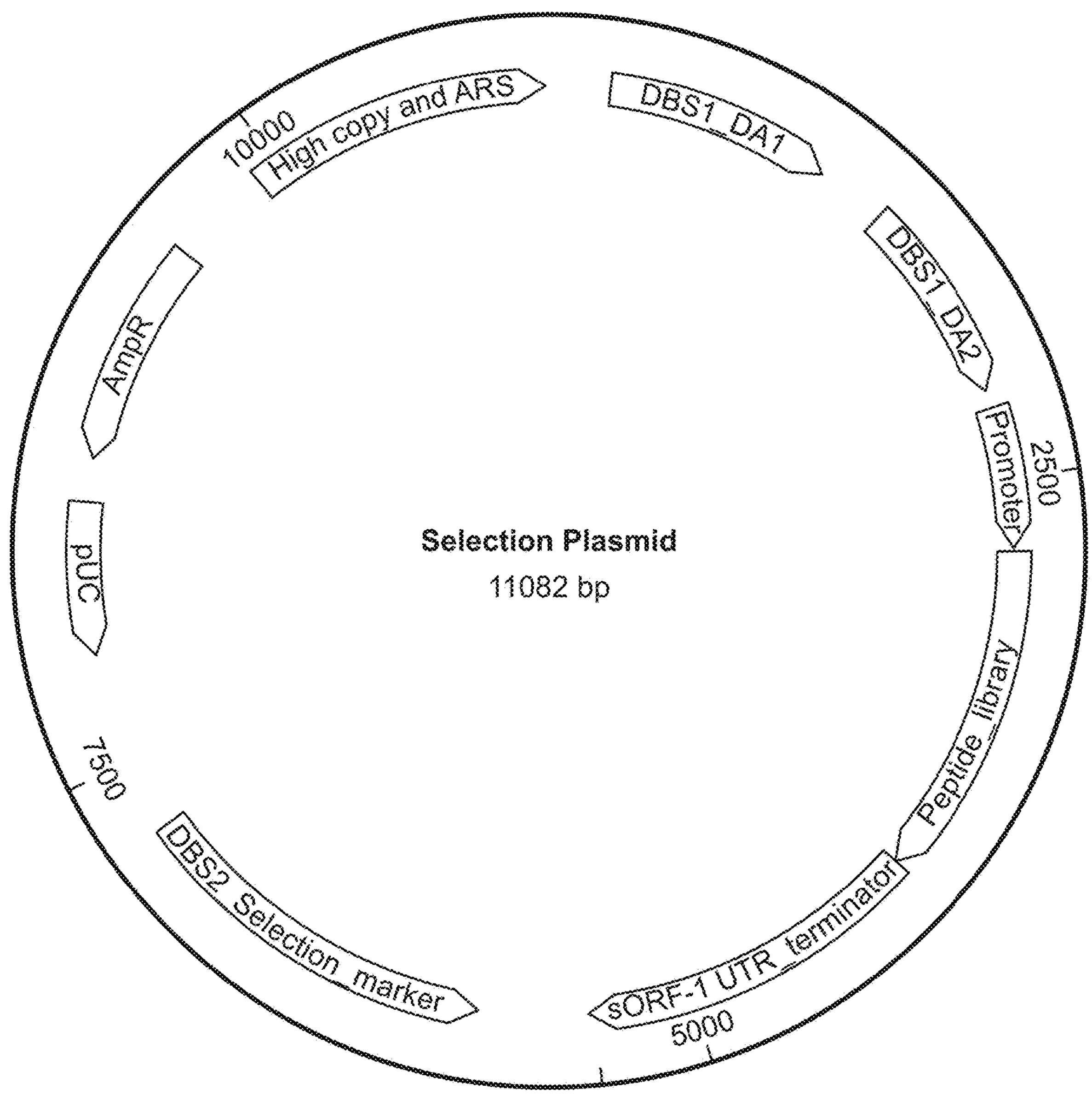
FIG. 9 shows an embodiment of a selection and library plasmid that encodes two death agents, both with the same DNA binding sequence, a positive selection agent driven by another DNA binding sequence and an inducible stabilized peptide library.
Figure 10:
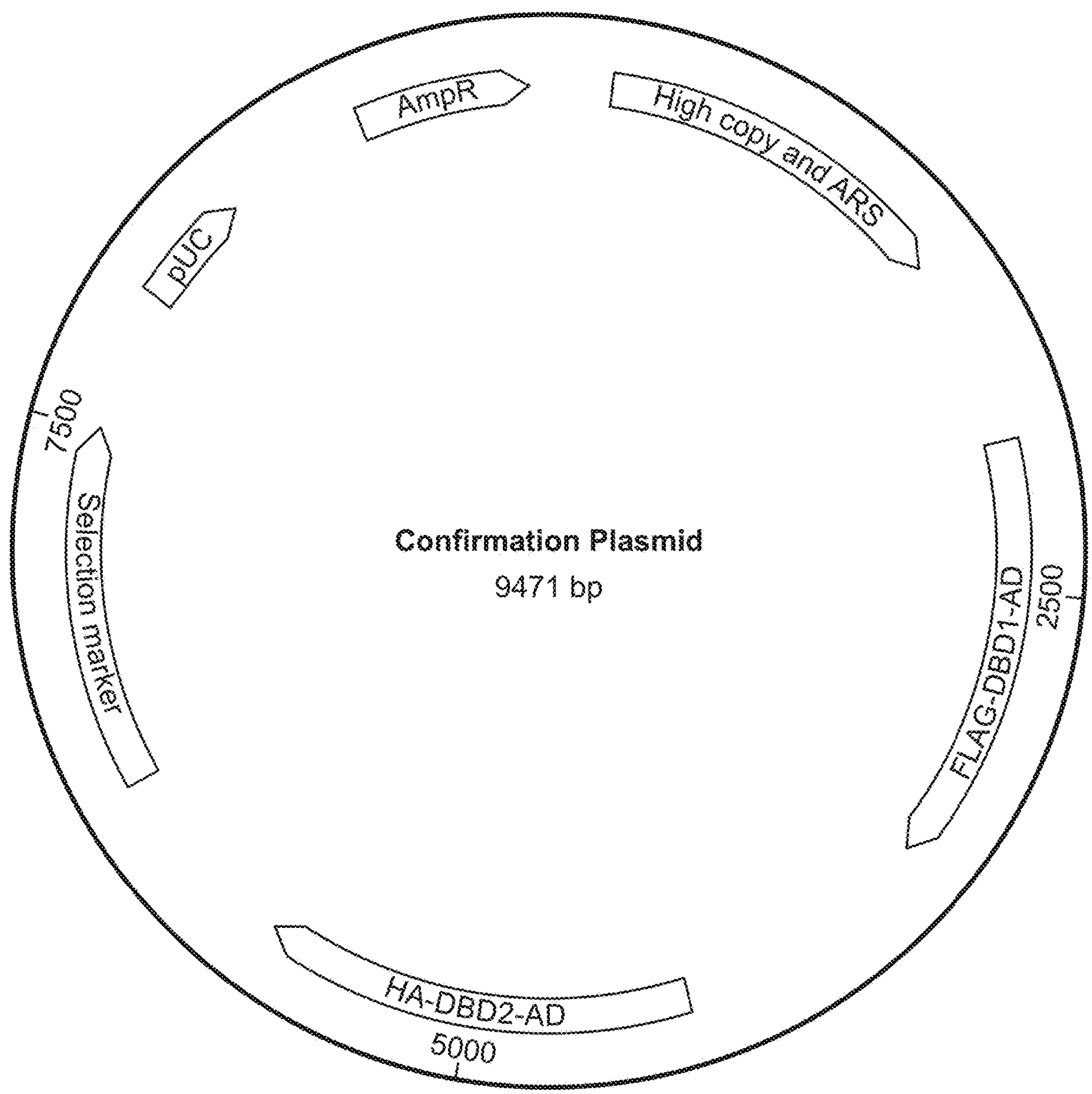
FIG. 10 shows an embodiment of a confirmation plasmid that encodes two bait-prey fusion proteins, each with its own DBD.

To identify peptides that can disrupt or facilitate a PPI, a PPI integration plasmid (PLASMID 1; FIG. 8), a selection and library plasmid (PLASMID 2; FIG. 9), and a confirmation plasmid (PLASMID 3; FIG. 10) can be used. The integration of PLASMID 1 into the genome of the host cell (as confirmed using PLASMID 3) can be followed by transformation of a library of PLASMID 2 encoding random peptides with, for example, NNK or NNN codons.

Expression of Fusion Proteins for PPI

In some embodiments, the host cell disclosed herein comprises a plasmid vector, which comprises the components of PLASMID 1 (FIG. 8), or any combination of the components of PLASMID 1. PLASMID 1 can contain, for example, two restriction sites that enable the integration of two proteins that constitute the PPI of interest. The PPI of interest can involve a pair of domains having known importance for carcinogenesis, such as p53-MDM2, RAS-RASBDPs, and MYC-MAX. The PPI of interest can also involve the interaction of an oncogene (such as Cyclin E family, Cyclin D family, c-MYC, EGFR, HER2, K-Ras, PDGFR, Raf kinase, and VEGF) or a tumor suppressor (such as BRCA1, BRCA2, cyclin-dependent kinase inhibitor 1C, PTEN, p16, p27, p53, p73, and Retinoblastoma protein (pRb)) with a known cellular interaction partner. The PPI of interest can involve the interaction of a protein involved in the DNA repair pathway (such as ATM, ATRX, BRCA1, BRCA2, ERCC1, FANCB, FANCF, FEN1, HMGA1, HMGA1, MDC1, MGMT, MLH1, MSH2, MSH4, Mre11A, NBS1, NEIL1, PARP1, PARP2, PMS2, RAD51, RAD52, RAD54, RAD51AP1, WRN, and XPF) with another cellular factor.

PLASMID 1 can be configured to express two proteins that constitute a PPI and an additional factor, for example, a variant of one of the proteins, such as KRAS (G12D, G12V, G12C, G12S, G13D, Q61K, or Q61L, etc.) and WT KRAS along with BRAF. The additional factor can also be another protein bound to one of the components of the PPI, or as member of a larger complex (such as YAP or TAZ disruption from TEAD without compromising VGLL4 binding to TEAD, or maintaining binding of BAX to BAK but preventing binding of BAX to BCL-2).

In some embodiments, the host cell disclosed herein comprises PLASMID 1, wherein a DNA sequence encoding a first polypeptide is inserted in frame with Gal4-DBD, a second polypeptide is inserted in frame with LexA-DBD, and wherein a DNA sequence encoding a third polypeptide is inserted in frame with VP64-AD.

In some embodiments, the first test protein is a variant of KRAS, the second test protein is c-Raf, and the third test protein is KRAS.

In some embodiments, the first test protein is YAP or TAZ, the second test protein is TEAD, and the third test protein is VGLL4.

PLASMID 1 can encode for the fusion of an activation domain or another gene activating moiety and a DBD to each protein driven by either a strong promoter and terminator (such as ADH1), or by an inducible promoter (such as GAL1). Other exemplary activation domains include those of VP16 and B42AD. In some embodiments, the DNA binding moiety is derived from LexA, TetR, LacI, Gli-1, YY1, glucocorticoid receptor, or Ume6 domain and the gene activating moiety is derived from Gal4, B42, or VP64, Gal4, NF-κB AD, Dof1, BP64, B42, or p65. Each protein fusion can be tagged for subsequent biochemical experiments with, for example, a FLAG, HA, MYC, or His tag. PLASMID 1 can also include bacterial selection and propagation markers (i.e. ori and AmpR), and yeast replication and selection markers (i.e. TRP1 and CEN or 2 um). The plasmid may contain multiple bait proteins fused to different DBDs. The plasmid can also be integrated into the genome at a specified locus.

Disclosed herein, in certain embodiments, is a library of plasmid vectors, each plasmid vector comprising: a DNA sequence encoding a different peptide sequence operably linked to a first switchable promoter; a DNA sequence encoding a death agent under control of a second switchable promoter; and a DNA sequence encoding a positive selection reporter under control of a third switchable promoter.

Expression of Selection Markers

Positive Selection Markers

An efficient interaction between the two test proteins can direct RNA polymerase to a specific genomic site, and allow expression of a protein that enables an organism to grow on selection media. The selection media can be specific to, for example, ADE2, URA3, TRP1, $KAN^R$, or $NAT^R$, and can lack the essential component (Ade, Ura, Trp) or can include a drug (G418, NAT). PLASMID 2 (FIG. 9) can encode for one or more positive selection markers that enable an organism to grow on selection media.

Figure 6:
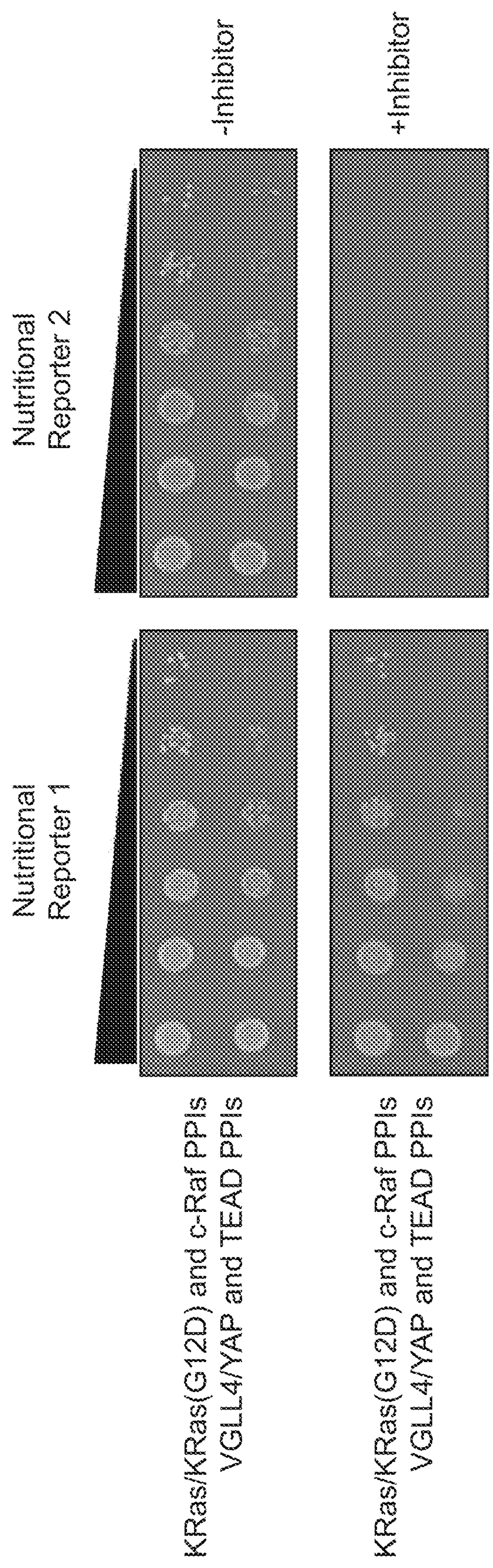
FIG. 6 illustrates two platforms to identify a compound that specifically disrupts a protein-protein interaction in cell culture by selecting for nutritional reporter.

FIG. 6 shows the results of two systems for identifying a compound that specifically disrupts a protein-protein interaction in cell culture using a positive selection marker. In the first platform, KRas and KRas(G12D) fused to DBDs and c-Raf fused to AD were expressed in yeast cells. In the absence of any inhibitors, the DBD fusion protein and AD fusion protein pairs maintain interaction to drive expression of nutritional reporters 1 and 2. A 5-fold dilution series starting at $10^4$ cells were spotted onto selective media with or without inhibitor and visualized after 2 days of growth at 30° C. The results showed that the cells grown on media that selected for nutritional reporter 2 had particularly poor survival rate when the inhibitor was added, illustrating both (1) the specificity of the inhibitor for KRas(G12D) and c-Raf and (2) the validity of the screening assay.

In the second platform, VGLL4 and YAP fused to DBDs and TEAD fused to AD were expressed in cells. In the absence of any inhibitors, the DBD fusion protein and AD fusion protein pairs maintain interaction to drive expression of nutritional reporters 1 and 2. A 5-fold dilution series starting at $10^4$ cells were spotted onto selective media with or without inhibitor and visualized after 2 days of growth at 30° C. The results showed that the cells grown on media that selected for nutritional reporter 2 had particularly poor survival rate when the inhibitor was added, illustrating both (1) the specificity of the inhibitor for the YAP and TEAD interaction and (2) the validity of the screening assay.

Negative Selection Markers

An inducible two-hybrid approach can be employed, which can drive the expression of any one or combination of several cytotoxic reporters (death agents) as well as positive selection markers. A method of the disclosure involving induced expression of a combination of cytotoxic reporters in a two-hybrid system can allow for a multiplicative effect in lowering the false-positive rate of the two-hybrid assay, as all of the cytotoxic reporters must simultaneously be "leaky" to allow for an induced cell to survive. The cytotoxic reporters can be, for example:

TABLE 1

| | | |
|---|---|---|
| Cholera toxin (CtxA) | SEQ ID NO.: 1 | MVKIIFVFFIFLSSFSYANDDKLYRADSRPPDEIKQSGGLMPRGQSEYFDRGTQMN<br>INLYDHARGTQTGFVRHDDGYVSTSISLRSAHLVGQTILSGHSTYYIYVIATAPNM<br>FNVNDVLGAYSPHPDEQEVSALGGIPYSQIYGWYRVHFGVLDEQLHRNRGYRDRYY<br>SNLDIAPAADGYGLAGFPPEHRAWREEPWIHHAPPGCGNAPRSSMSNTCDEKTQSL<br>GVKFLDEYQSKVKRQIFSGYQSDIDTHNRIKDEL |
| SpvB toxin (*Salmonella enterica*) | SEQ ID NO.: 2 | MLILNGFSSATLALITPPFLPKGGKALSQSGPDGLASITLPLPISAERGFAPALAL<br>HYSSGGGNGPFGVGWSCATMSIARRTSHGVPQYNDSDEFLGPDGEVLVQTLSTGDA<br>PNPVTCFAYGDVSFPQSYTVTRYQPRTESSFYRLEYWVGNSNGDDFWLLHDSNGIL<br>HLLGKTAAARLSDPQAASHTAQWLVEESVTPAGEHIYYSYLAENGDNVDLNGNEAG<br>RDRSAMRYLSKVQYGNATPAADLYLWTSATPAVQWLFTLVFDYGERGVDPQVPPAF<br>TAQNSWLARQDPFSLYNYGFEIRLHRLCRQVLMFHHFPDELGEADTLVSRLLLEYD<br>ENPILTQLCAARTLAYEGDGYRRAPVNNMMPPPPPPPPPMMGGNSSRPKSKWAIVE<br>ESKQIQALRYYSAQGYSVINKYLRGDDYPETQAKETLLSRDYLSTNEPSDEEFKNA<br>MSVYINDIAEGLSSLPETDHRVVYRGLKLDKPALSDVLKEYTTIGNIIIDKAFMST<br>SPDKAWINDTILNIYLEKGHKGRILGDVAHFKGEAEMLFPPNTKLKIESIVNCGSQ<br>DFASQLSKLRLSDDATADTNRIKRIINMRVLNS |
| CARDS toxin (*Mycoplasma pneumoniae*) | SEQ ID NO.: 3 | MSENLYFQGHMPNPVRFVYRVDLRSPEEIFEHGFSTLGDVRNFFEHILSTNFGRSY<br>FISTSETPTAAIRFFGSWLREYVPEHPRRAYLYEIRADQHFYNARATGENLLDLMR<br>QRQVVFDSGDREMAQMGIRALRTSFAYQREWFTDGPIAAANVRSAWLVDAVPVEPG<br>HAHHPAGRVVETTRINEPEMHNPHYQELQTQANDQPWLPTPGIATPVHLSIPQAAS<br>VADVSEGTSASLSFACPDWSPPSSNGENPLDKCIAEKIDNYNLQSLPQYASSVKEL<br>EDTPVYLRGIKTQKTFMLQADPQNNNVFLVEVNPKQKSSFPQTIFFWDVYQRICLK<br>DLTGAQISLSLTAFTTQYAGQLKVHLSVSAVNAVNQKWKMTPQDIAITQFRVSSEL<br>LGQTENGLFWNTKSGGSQHDLYVCPLKNPPSDLEELQIIVDECTTHAQFVTMRAAS<br>TFFVDVQLGWYWRGYYYTPQLSGWSYQMKTPDGQIFYDLKTSKIFFVQDNQNVFFL<br>HNKLNKQTGYSWDWVEWLKHDMNEDKDENFKWYFSRDDLTIPSVEGLNFRHIRCYA<br>DNQQLKVIISGSRWGGWYSTYDKVESNVEDKILVKDGFDRF |
| SpyA Toxin (*Streptococcus pyogenes*) | SEQ ID NO.: 4 | MLKKRYQLAMILLLSCFSLVWQTEGLVELFVCEHYERAVCEGTPAYFTFSDQKGAE<br>TLIKKRWGKGLVYPRAEQEAMAAYTCQQAGPINTSLDKAKGKLSQLTPELRDQVAQ<br>LDAATHRLVIPWNIVVYRYVYETFLRDIGVSHADLTSYYRNHQFNPHILCKIKLGT<br>RYTKHSFMSTTALKNGAMTHRPVEVRICVKKGAKAAFVEPYSAVPSEVELLFPRGC<br>QLEVVGAYVSQDHKKLHIEAYFKGSL |
| HopU1 (*Pseudomonas syringae*) | SEQ ID NO.: 5 | MNINRQLPVSGSERLLTPDVGVSRQACSERHYSTGQDRHDFYRFAARLHVDAQCFG<br>LSIDDLMDKFSDKHFRAEHPEYRDVYPEECSAIYMHTAQDYSSHLVRGEIGTPLYR<br>EVNNYLRLQHENSGREAEIDNHDEKLSPHIKMLSSALNRLMDVAAFRGTVYRGIRG<br>DLDTIARLYHLFDTGGRYVEPAFMSTTRIKDSAQVFEPGTPNNIAFQISLKRGADI<br>SGSSQAPSEEEIMLPMMSEFVIEHASALSEGKHLFVLSQI |
| Chelt toxin | SEQ ID NO.: 6 | MKTIISLIFIMFPLFVSAHNGNFYRADSRSPNEIKDLGGLYPRGYYDFFERGTPMS<br>ISLYDHARGAPSGNTRYDDGFVSTTTDIDSAHEIGQNILSGYTEYYIYLIAPAPNL<br>LDVNAVLGRYSPHPQENEYSALGGIPWTQVIGWYVVNNGVLDRNIHRNRQFRADLF<br>NNLSPALPSESYQFAGFEPEHPAWRQEPWINFAPPGCGRNVRLTKHINQQDCSNSQ<br>EELVYKKLQDLRTQFKVDKKLKLVNKTSSNNIIFPNHDFIREWVDLDGNGDLSYCG<br>FTVDSDGSRKRIVCAHNNGNFTYSSINISLSDYGWPKGQRFIDANGDGLVDYCRVQ<br>YVWTHLYCSLSLPGQYFSLDKDAGYLDAGYNNSRAWAKVIGTNKYSFCRLTSNGYI<br>CTDIDSYSTAFKDDDQGWADSRYWMDIDGNGGDDYCRLVYNWTHLRCNLQGKDGLW<br>KRVESKYLDGGYPSLRFKIKMTSNKDNYCRIVRNHRVMECAYVSDNGEFHNYSLNM<br>PFSLYNKNDIQFIDIDGDNRDDICRYNSAPNTMECYLNQDKSFSQNKLVLYLSAKP<br>ISSLGSGSSKIIRTFNSEKNSSAYCYNAGYGTLRCDEFVIY |

TABLE 1-continued

| | | |
|---|---|---|
| Certhrax toxin | SEQ ID NO.: 7 | MKEIIRNLVRLDVRSDVDENSKKTQELVEKLPHEVLELYKNVGGEIYITDKRLTQH<br>EELSDSSHKDMFIVSSEGKSFPLREHFVFAKGGKEPSLIIHAEDYASHLSSVEVYY<br>ELGKAIIRDTFPLNQKELGNPKFINAINEVNQQKEGKGVNAKADEDGRDLLFGKEL<br>KKNLEHGQLVDLDLISGNLSEFQHVFAKSFALYYEPHYKEALKSYAPALFNYMLEL<br>DQMRFKEISDDVKEKNKNVLDFKWYTRKAESWGVQTFKNWKENLTISEKDIITGYT<br>GSKYDPINEYLRKYDGEIIPNIGGDLDKKSKKALEKIENQIKNLDAALQKSKITEN<br>LIVYRRVSELQFGKKYEDYNLRQNGIINEEKVMELESNFKGQTFIQHNYMSTSLVQ<br>DPHQSYSNDRYPILLEITIPEGVHGAYIADMSEYPGQYEMLINRGYTFKYDKFSIV<br>KPTREEDKGKEYLKVNLSIYLGNLNREK |
| EFV toxin | SEQ ID NO.: 8 | MSQLNKWQKELQALQKANYQETDNQLFNVYRQSLIDIKKRLKVYTENAESLSFSTR<br>LEVERLFSVADEINAILQLNSPKVEKTIKGYSAKQAEQGYYGLWYTLEQSQNIALS<br>MPLINHDYIMNLVNAPVAGKRLSKRLYKYRDELAQNVTNNIITGLFEGKSYAEIAR<br>WINEETEASYKQALRIARTEAGRTQSVTTQKGYEEAKELGINIKKKWLATIDKHTR<br>RTHQELDGKEVDVDEEFTIRGHSAKGPRMFGVASEDVNCRCTTIEVVDGISPELRK<br>DNESKEMSEFKSYDEWYADRIRQNESKPKPNFTELDFFGQSDLQDDSDKWVAGLKP<br>EQVNAMKDYTSDAFAKMNKILRNEKYNPREKPYLVNIIQNLDDAISKFKLKHDIIT<br>YRGVSANEYDAILNGNVFKEFKSTSINKKVAEDFLNFTSANKDGRVVKFLIPKGTQ<br>GAYIGTNSSMKKESEFLLNRNLKYTVEIVDNILEVTILG |
| ExoT | SEQ ID NO.: 9 | MHIQSSQQNPSFVAELSQAVAGRLGQVEARQVATPREAQQLAQRQEAPKGEGLLSR<br>LGAALARPFVAIIEWLGKLLGSRAHAATQAPLSRQDAPPAASLSAAEIKQMMLQKA<br>LPLTLGGLGKASELATLTAERLAKDHTRLASGDGALRSLATALVGIRDGSLIEASR<br>TQAARLLEQSVGGIALQQWGTAGGAASQHVLSASPEQLREIAVQLHAVMDKVALLR<br>HAVESEVKGEPVDKALADGLVEHFGLEAEQYLGEHPDGPYSDAEVMALGLYTNGEY<br>QHLNRSLRQGRELDAGQALIDRGMSAAFEKSGPAEQVVKTFRGTQGRDAFEAVKEG<br>QVGHDAGYLSTSRDPSVARSFAGLGTITTLFGRSGIDVSEISIEGDEQEILYDKGT<br>DMRVLLSAKDGQGVTRRVLEEATLGERSGHSEGLLDALDLATGTDRSGKPQEQDLR<br>LRMRGLDLA |
| CdtB | SEQ ID NO.: 10 | MKKIICLFLSFNLAFANLENFNVGTWNLQGSSAATESKWSVSVRQLVSGANPLDIL<br>MIQEAGTLPRTATPTGRHVQQGGTPIDEYEWNLGTLSRPDRVFIYYSRVDVGANRV<br>NLAIVSRMQAEEVIVLPPPTTVSRPIIGIRNGNDAFFNIHALANGGTDVGAIITAV<br>DAHFANMPQVNWMIAGDFNRDPSTITSTVDRELANRIRVVFPTSATQASGGTLDYA<br>ITGNSNRQQTYTPPLLAAILMLASLRSHIVSDHFPVNFRKF |
| Diptheria toxin | SEQ ID NO.: 11 | MSRKLFASILIGALLGIGAPPSAHAGADDVVDSSKSFVMENFSSYHGTKPGYVDSI<br>QKGIQKPKSGTQGNYDDDWKGFYSTDNKYDAAGYSVDNENPLSGKAGGVVKVTYPG<br>LTKVLALKVDNAETIKKELGLSLTEPLMEQVGTEEFIKRFGDGASRVVLSLPFAEG<br>SSSVEYINNWEQAKALSVELEINFETRGKRGQDAMYEYMAQACAGNRVRRSVGSSL<br>SCINLDWDVIRDKTKTKIESLKEHGPIKNKMSESPNKTVSEEKAKQYLEEFHQTAL<br>EHPELSELKTVTGTNPVFAGANYAAWAVNVAQVIDSETADNLEKTTAALSILPGIG<br>SVMGIADGAVHHNTEEIVAQSIALSSLMVAQAIPLVGELVDIGFAAYNFVESIINL<br>FQVVHNSYNRPAYSPGHKTQPFLHDGYAVSWNTVEDSIIRTGFQGESGHDIKITAE<br>NTPLPIAGVLLPTIPGKLDVNKSKTHISVNGRKIRMRCRAIDGDVTFCRPKSPVYV<br>GNGVHANLHVAFHRSSSEKIHSNEISSDSIGVLGYQKTVDHTKVNSKLSLFFEIKS |
| ExoU/VipB | SEQ ID NO.: 12 | MKLAEIMTKSRKLKRNLLEISKTEAGQYSVSAPEHKGLVLSGGGAKGISYLGMIQA<br>LQERGKIKNLTHVSGASAGAMTASILAVGMDIKDIKKLIEGLDITKLLDNSGVGFR<br>ARGDRFRNILDVIYMMQMKKHLESVQQPIPPEQQMNYGILKQKIALYEDKLSRAGI<br>VINNVDDIINLTKSVKDLEKLDKALNSIPTELKGAKGEQLENPRLTLGDLGRLREL<br>LPEENKHLIKNLSVVVTNQTKHELERYSEDTTPQQSIAQVVQWSGAHPVLFVPGRN<br>AKGEYIADGGILDNMPEIEGLDREEVLCVKAEAGTAFEDRVNKAKQSAMEAISWFK<br>ARMDSLVEATIGGKWLHATSSVLNREKVYYNIDNMIYINTGEVTTTNTSPTPEQRA<br>RAVKNGYDQTMQLLDSHKQTFDHPLMAILYIGHDKLKDALIDEKSEKEIFEASAHA<br>QAILHLQEQIVKEMNDGDYSSVQNYLDQIEDILTVDAKMDDIQKEKAFALCIKQVN<br>FLSEGKLETYLNKVEAEAKAAAEPSWATKILNLLWAPIEWVVSLFKGPAQDFKVEV<br>QPEPVKVSTSENQETVSNQKDINPAVEYRKIIAEVRREHTDPSPSLQEKERVGLST<br>TFGGH |
| HopPtoE | SEQ ID NO.: 13 | MNRVSGSSSATWQAVNDLVEQVSERTTLSTTGYQTAMGRLNKPEKSDADALMTMRR<br>AQQYTDSAKRTYISETLMNLADLQQRKIYRTNSGNLRGAIEMTPTQLTDCVQKCRE<br>EGFSNCDIQALEIGLHLRHKLGISDFTIYSNRKLSHNYVVIHPSNAFPKGAIVDSW<br>TGQGVVELDFKTRLKFKHREENYAVNANMHEWIERYGQAHVID |
| HopPtoF | SEQ ID NO.: 14 | MGNICGTSGSRHVYSPSHTQRITSAPSTSTHVGGDTLTSIHQLSHSQREQFLNMHD<br>PMRVMGLDHDTELFRTTDSRYIKNDKLAGNPQSMASILMHEELRPNRFASHTGAQP<br>HEARAYVPKRIKATDLGVPSLNVMTGSLARDGIRAYDHMSDNQVSVKMRLGDFLER<br>GGKVYADASSVADDGETSQALIVTLPKGQKVPVERV |
| HopPtoG | SEQ ID NO.: 15 | MQIKNSHLYSASRMVQNTFNASPKMEVTNAIAKNNEPAALSATQTAKTHEGDSKGQ<br>SSNNSKLPFRAMRYAAYLAGSAYLYDKTANNFFLSTTSLHDGKGGFTSDARLNDAQ<br>DKARKRYQNNHSSTLENKNSLLSPLRLCGENQFLTMIDYRAATKIYLSDLVDTEQA<br>HTSILKNIMCLKGELTNEEAIKKLNPEKTPKDYDLTNSEAYISKNKYSLTGVKNEE<br>TGSTGYTSRSITKPFVEKGLKHFIKATHGEKALTPKQCMETLDNLLRKSITLNSDS<br>QFAAGQALLVFRQVYAGEDAWGDAERVILKSHYNRGTVLQDEADKIELSRPFSEQD<br>LAKNMFKRNTSIAGPVLYHAYIYIQEKIFKLPPDKIEDLKHKSMADLKNLPLTHVK<br>LSNSGVGFEDASGLGDSFTALNATSCVNHARIMSGEPPLSKDDVVILIGCLNAVYD<br>NSSGIRHSLREIARGCFVGAGFTVQDGDDFYKQICKNASKQFYNG |

TABLE 1-continued

| | | |
|---|---|---|
| VopF | SEQ ID NO.: 16 | MFKISVSQQANVMSTSDTAQRSSLKISIKSICNKSLSKKLHTLAEKCRRFSQELKE<br>HTASKKQIVEQATTTVRESSLTKSDSELGSSRSLLTSDVLSSSSSHEDLTAVNLED<br>NDSVFVTIESSSELIVKQDGSIPPAPPLPGNIPPAPPLPSAGNIPTAPGLPKQKAT<br>TESVAQTSDNRSKLMEEIRQGVKLRATPKSSSTEKSASDPHSKLMKELINHGAKLK<br>KVSTSDIPVPPPLPAAFASKPTDGRSALLSEIAGESKDRLRKAGSSETLNVSQPTV<br>AESSIPEAYDLLLSDEMFNLSPKLSETELNTLADSLADYLFKAADIDWMQVIAEQT<br>KGSTQATSLKSQLEQAPEYVKAFCDEILKFPDCYKSADVASPESPKAGPSSVIDVA<br>LKRLQAGRNRLFSTIDAKGTNELKKGEAILESAINAARSVMTAEQKSALLSSNVKS<br>ATFKVFSELPCMEGFAEQNGKAAFNALRLAFYSSIQSGDTAQQDIARFMKENLATG<br>FSGYSYLGLTSRVAQLEAQLAALTTK |
| YopJ | SEQ ID NO.: 17 | MIGPISQINISGGLSEKETSSLISNEELKNIITQLETDISDGSWFHKNYSRMDVEV<br>MPALVIQANNKYPEMNLNLVTSPLDLSIEIKNVIENGVRSSRFIINMGEGGIHFSV<br>IDYKHINGKTSLILFEPANFNSMGPAMLAIRTKTAIERYQLPDCHFSMVEMDIQRS<br>SSECGIFSFALAKKLYIERDSLLKIHEDNIKGILSDGENPLPHDKLDPYLPVTFYK<br>HTQGKKRLNEYLNTNPQGVGTVVNKKNETIVNREDNNKSIVDGKELSVSVHKKRIA<br>EYKTLLKV |
| AvrPtoB | SEQ ID NO.: 18 | MAGINGAGPSGAYFVGHTDPEPASGGAHGSSSGASSSNSPRLPAPPDAPASQARDR<br>REMLLRARPLSRQTREWVAQGMPPTAEAGVPIRPQESAEAAAPQARAEERHTPEAD<br>AAASHVRTEGGRTPQALAGTSPRHTGAVPHANRIVQQLVDAGADLAGINTMIDNAM<br>RRHAIALPSRTVQSILIEHFPHLLAGELISGSELATAFRAALRREVRQQEASAPPR<br>TAARSSVRTPERSTVPPTSTESSSGSNQRTLLGRFAGLMTPNQRRPSSASNASASQ<br>RPVDRSPPRVNQVPTGANRVVMRNHGNNEADAALQGLAQQGVDMEDLRAALERHIL<br>HRRPIPMDIAYALQGVGIAPSIDTGESLMENPLMNLSVALHRALGPRPARAQAPRP<br>AVPVAPATVSRRPDSARATRLQVIPAREDYENNVAYGVRLLSLNPGAGVRETVAAF<br>VNNRYERQAVVADIRAALNLSKQFNKLRTVSKADAASNKPGFKDLADHPDDATQCL<br>FGEELSLTSSVQQVIGLAGKATDMSESYSREANKDLVFMDMKKLAQFLAGKPEHPM<br>TRETLNAENIAKYAFRIVP |
| SdbA | SEQ ID NO.: 19 | MHKKYNYYSLEKEKKTFWQHILDILKAPFRLPGWVVSFFLARNITHVALNPNNIPQ<br>QRLIHLTKTSNRPEDDIVVINFKKRPPHKWENDTLIKIANTIAALPFVTPRLRTRL<br>HYDNENDINHVNKLLAEIDALVQGKSKQKYCKGRAFDWSKIHLKGLEFLDPKMRGY<br>VYEQLHEKYGYVSYTTKRKPNIEFFTLKTPDGSELDSVQVTGEDEEKKPMGERKFI<br>ITCIARDQNFINWIKDLNYTAKNLGATAISFNYRGVDYSRGLVWTENNLVDDILAQ<br>VQRLISLGADPKNICLDGMCIGGAVATIAAAKLHEKGMKVKLNNERSFTSLSSLVF<br>GFIVPELQTANWWSPLTYGRFLLAGVVYALLTPLIWLAGWPVDVTKAWNRIPAQDK<br>MYSVVRDKDNGLYDGVIHDHFCSIASLVDSQINSILYKLSTDQPLTEEEKQILCDD<br>QFSHHFKPSQSVLKNPKYKGPHFISRQDLVAELGHREEYTNHDYFLDRLREKFQLD<br>RATRPVALAEDGEKDIDGISSQLSNNKERPLIIASSGGTGHISATHGIINDLQSKT<br>DNVVITQHHAELYKNKPFSITSVLIRIGVWFTSLPILEDILKGVMRFIGYPVLPSS<br>SIFWDQMSKIQQSETKKENGIETGRTRPYVDMLLDIYPEGYEYTAFNNATHLTSSI<br>EDIQTMISFKGHVEEDNRNIVYQNILQRLMHAAKQNTPYTRLISTQALSLGAICDA<br>VKYYNTVFLPVYNAERGTSYQPIAIDQYMTDLPSLGCIHFMNNLEELTSEQRQLME<br>IHAVNMSEPFKEAHFGKEQGFKAVHNIDPRNNPMIRNAFKDPSLTKYLDKTQSFDL<br>HFNVYKKEKQNALPVLNGKEKITIKPHAKIASIMIGSLAANASADYAKYLLNQGYE<br>HIFLFGGLNDSIAARIDQIINSYPAPTRDEIRKKIILLGNQSDVEMAPIMTRSNCV<br>VIRGGGLSVMEQMAMPIMDDKIVLLHHEDNEEGPLTSGLSWEDGNSDKLIEYLSEK<br>GAYAKKTSPGLCSGHLHEAEKSFEKKYHGQLKSTETKKKVDLTIPQQETYSLKKEW<br>DRKTGYTESGHILSHQHRFENTIPEVREPFCSKEDLHHNELSSQSLVSVSAG |
| SidG | SEQ ID NO.: 20 | MSRSKDEVLEANDSLFGITVQTWGTNDRPSNGMMNFADQQFFGGDVGHASINMKLP<br>VTDKTKQWIEKYCYSQTYDQFKKVKGNEDKTYEEYLKTAKRLIPVELKTQVTRKAQ<br>YDSNGNLVTTHEKAYEQIYFDIDWSWWPGRLQNTEDDMVWEREGKHFEYDEKWKEY<br>LQPEQRVHRGKLGSRKMDYAPTSIIHQRDIPTSELEKITRDHKIHTIEEKLNVVKL<br>LQSKIDEMPHTKMSPSMELMFKNLGINVEKLLDETKDNGVDPTNLEAMREYLTNRL<br>TERKLELETELSEAKKEVDSTQVKNKVEDVYYDFEYKLNQVRKKMEEVNSQLEKMD<br>SLLHKLEGNTSGPIPYTAEIDELMSVLPFLKEELELENGTLSPKSIENLIDHIDEL<br>KNELASKQEKKNERNLNLIKKYEELCEQYKDDEEGLEEALWEEGIDVEEVNSAKKD<br>ISKPAPEIQKLTDLQEQLRNHKESGVKLSSELEETLNSSVKMWKTKIDSPCQVISE<br>SSVKALVSKINSTRPELVKEKEQLPEQEESLSKEAKKAQEELIKIQEFSQFYSENS<br>SAYMVIGLPPHHQVSLPLAVNGKRGLHPEAMLKKMHELVAGPEKKEENLHTNNCSL<br>TSIEVLSAGAQHDPLLHSIMGTRALGFFGTPQQVLENAKLTSKTINEGKKSNIFTP<br>LVTASPLDRALGYAMSIYMDPEASKAKQNAGLALGVLVGLAKTPGIIIGSLLNPKQ<br>GFNDILNTLNLVYSRNSTGLKVGLTLMALPAMIVLAPLAAIQKGVEVIAETIAKPF<br>KLIANLFKQKPESTDEITVSVGSKKVAEKEGSYSNTALAGLVNSKIKSKIDENTIT<br>VEFQKSPQKMIEEFESQLKENPGKVVVLSEKAHNAVLKFVSKSDDEALKQKFYDCC<br>NQSVARSQKFAPKTRDEIDELVEEVTSTDKTELTTSPRQEPSMSSTIDEEENIDSE<br>HQIETGTESTMRI |
| VpdA | SEQ ID NO.: 21 | MKTKQEVSQQDKLKDSKSSTPLQTKETWFISDALNITFDPYDFSISVTEQAPMPYR<br>IVESGGGSRILAHIGALDELTRHGLKFTEFSGSSAGAMVAAFAYLGYNCSEIKQII<br>SWFNEDKLLDSPLIFNFNNIKQIFNKGGLSSAKLMRQAANYVILKKVMDIISDEKF<br>KTRFAKFQNFLEENIYRCPENITFQTLARIKEICPECELGEKLFITGTNLSTQKHE<br>VFSIDTTPSMALADAIIISANLPIAFERICYQGNVYSDGGISNNLPAHCFSEKGHK<br>TTFLKHKDDVDFSVLALQFDNGLEENALYSQNPIPKWSWLSNTFYSLITGHPNVTE<br>NWYEDLQILRRHAHQSILIKTPTIALTNLTISQDTKKALVESGRTAAKTYLELHEF<br>YTDDYGNIRHNECLHEKFQKPEELLDYCVLHSHFELLKKIKQAISCSQYLEKGYKH<br>YLCELCDNLLPPQLKCPNEGSGTEQPEIKLEKDTIICEKNNNSGLTFSMTFFGVPS |

TABLE 1-continued

| | | |
|---|---|---|
| | | PLVKTLNQDSPELKIKLFTGLYPILIQNWQNLCPVSGISGILNSIRMSFVEISSTDTCIKTLIDKLNEIEIGHFLIFVFKAALKNYDKHDFILLLKNLKHLHHSIELIRNKPFHSDDRFYGQWSFEGHDPKRILEFIKSDDISGLMTILEDKKALPNNKPN |
| Lpg0969 | SEQ ID NO.: 22 | MVSLEHIQKLISECRKLGKDGLDNGTNGLIPELEIDVVPPSAFLGVGNNPAIFVNSKTYKLMRTTHEKWVENKTIVEKSYLLSQPAIKIIGAIVHETGHAFNVAAKIPNTEANACIFEIEVLMRLFQVKSPLLLGCTELDMQSYFKSRLTDYNKCVKDCQCLAEMVEFITHQFKLDEVSISEKENQIPLLSISNKWPGLFAKKQIAPDMDKLLTSPVTITPEVKILFYQLVKEHFHSPETEIKLDI |
| Lpg1978 | SEQ ID NO.: 23 | MYKIYSYLGWRIDMKTENLPQAGQEAQIDKKIHFIWVGHIMPQKNIQVVSEWAEKNPGYETIIWVDKKIAPAKELDLFILDMKSKGITVKDINEEGVCRDSIRHELDQESPNYGMVSDMLRLNILAAEGGIYLDSDILCSAPFPDEIYAPFGFLLSPWSQGANNTLCNDIILCSKGNQIIQQLADAIEQSYIARDSFEFTHEYASMKETKGERIAKTLGVTGPGFLFHQLKKMGILNDKSEMEAIHWELQDQRYLIDGSVKEPDYFYVPQNNTNDASWVPSIKRPGIENMSFQERLENAVQLIAFDIQKTGLFNLDHYANELKVKQNSWCIAAETSPELKPDSYLLIRPRDKTGEWTLYYVDEDKKLNPVTLPVIKGAIKLSEVSDPLRKFHTLLSQVSDPVNPTAHELKQIGRALIELKPRQDEWHCKNKWSGAEEIAQELWQRITSNETLRAQIKQCFTQFESLKPRVAELGLTRASGAGTEVEAHESTVKEQEIISQNTVGEEGTKEKNSVQLASENSSDEKIKTAHDLIDEIIQDVIQLDGKLGLLGGNTRQLEDGRVINIPNGAAMIFDDYKKYKQGELTAESALESMIKIAKLSNQLNRHTFFNQRQPETGQFYKKVAAIDLQTTIAAEYDNNHGLRI |
| YopE | SEQ ID NO.: 24 | MKISSFISTSLPLPTSVSGSSSVGEMSGRSVSQQTSDQYANNLAGRTESPQGSSLASRIIERLSSVAHSVIGFIQRMFSEGSHKPVVTPAPTPAQMPSPTSFSDSIKQLAAETLPKYMQQLNSLDAEMLQKNHDQFATGSGPLRGSITQCQGLMQFCGGELQAEASAILNTPVCGIPFSQWGTIGGAASAYVASGVDLTQAANEIKGLAQQMQKLLSLM |
| SptP | SEQ ID NO.: 25 | MLKYEERKLNNLTLSSFSKVGVSNDARLYIAKENTDKAYVAPEKFSSKVLTWLGKMPLFKNTEVVQKHTENIRVQDQKILQTFLHALTEKYGETAVNDALLMSRINMNKPLTQRLAVQITECVKAADEGFINLIKSKDNVGVRNAALVIKGGDTKVAEKNNDVGAESKQPLLDIALKGLKRTLPQLEQMDGNSLRENFQEMASGNGPLRSLMTNLQNLNKIPEAKQLNDYVTTLTNIQVGVARFSQWGTCGGEVERWVDKASTHELTQAVKKIHVIAKELKNVTAELEKIEAGAPMPQTMSGPTLGLARFAVSSIPINQQTQVKLSDGMPVPVNTLTFDGKPVALAGSYPKNTPDALEAHMKMLLEKECSCLVVLTSEDQMQAKQLPPYFRGSYTFGEVHTNSQKVSSASQGEAIDQYNMQLSCGEKRYTIPVLHVKNWPDHQPLPSTDQLEYLADRVKNSNQNGAPGRSSSDKHLPMIHCLGGVGRTGTMAAALVLKDNPHSNLEQVRADFRDSRNNRMLEDASQFVQLKAMQAQLLMTTAS |
| SopE2 | SEQ ID NO.: 26 | MTNITLSTQHYRIHRSDVEPVKEKTTEKDIFAKSITAVRNSFISLSTSLSDRFSLHQQTDIPTTHFHRGNASEGRAVLTSKTVKDFMLQKLNSLDIKGNASKDPAYARQTCEAILSAVYSNNKDQCCKLLISKGVSITPFLKEIGEAAQNAGLPGEIKNGVFTPGGAGANPFVVPLIASASIKYPHMFINHNQQVSFKAYAEKIVMKEVTPLFNKGTMPTPQQFQLTIENIANKYLQNAS |
| SopB/SigD | SEQ ID NO.: 27 | MQIQSFYHSASLKTQEAFKSLQKTLYNGMQILSGQGKAPAKAPDARPEIIVLREPGATWGNYLQHQKASNHSLHNLYNLQRDLLTVAATVLGKQDPVLTSMANQMELAKVKADRPATKQEEAAAKALKKNLIELIAARTQQQDGLPAKEAHRFAAVAFRDAQVKQLNNQPWQTIKNTLTHNGHHYTNTQLPAAEMKIGAKDIFPSAYEGKGVCSWDTKNIHHANNLWMSTVSVHEDGKDKTLFCGIRHGVLSPYHEKDPLLRHVGAENKAKEVLTAALFSKPELLNKALAGEAVSLKLVSVGLLTASNIFGKEGTMVEDQMRAWQSLTQPGKMIHLKIRNKDGDLQTVKIKPDVAAFNVGVNELALKLGFGLKASDSYNAEALHQLLGNDLRPEARPGGWVGEWLAQYPDNYEVVNTLARQIKDIWKKNNQHHKDGGEPYKLAQRLAMLAHEIDAVPAWNCKSGKDRTGMMDSEIKREIISLHQTHMLSAPGSLPDSGGQKIFQKVLLNSGNLEIQKQNTGGAGNKVMKNLSPEVLNLSYQKRVGDENIWQSVKGISSLITS |
| SipA | SEQ ID NO.: 28 | MVTSVRTQPPVIMPGMQTEIKTQATNLAANLSAVRESATTTLSGEIKGPQLEDFPALIKQASLDALFKCGKDAEALKEVFTNSNNVAGKKAIMEFAGLFRSALNATSDSPEAKTLLMKVGAEYTAQIIKDGLKEKSAFGPWLPETKKAEAKLENLEKQLLDIIKNNTGGELSKLSTNLVMQEVMPYIASCIEHNFGCTLDPLTRSNLTHLVDKAAAKAVEALDMCHQKLTQEQGTSVGREARHLEMQTLIPLLLRNVFAQIPADKLPDPKIPEPAAGPVPDGGKKAEPTGININININIDSSNHSVDNSKHINNSRSHVDNSQRHIDNSNHDNSRKTIDNSRTFIDNSQRNGESHHSTNSSNVSHSHSRVDSTTHQTETAHSASTGAIDHGIAGKIDVTAHATAEAVTNASSESKDGKVVTSEKGTTGETTSFDEVDGVTSKSIIGKPVQATVHGVDDNKQQSQTAEIVNVKPLASQLAGVENVKTDTLQSDTTVITGNKAGTTDNDNSQTDKTGPFSGLKFKQNSFLSTVPSVTNMHSMHFDARETFLGVIRKALEPDTSTPFPVRRAFDGLRAEILPNDTIKSAALKAQCSDIDKHPELKAKMETLKEVITHHPQKEKLAEIALQFAREAGLTRLKGETDYVLSNVLDGLIGDGSWRAGPAYESYLNKPGVDRVITTVDGLHMQR |
| YpkA | SEQ ID NO.: 29 | MKSVKIMGTMPPSISLAKAHERISQHWQNPVGELNIGGKRYRIIDNQVLRLNPHSGFSLFREGVGKIFSGKMFNFSIARNLTDTLHAAQKTTSQELRSDIPNALSNLFGAKPQTELPLGWKGEPLSGAPDLEGMRVAETDKFAEGESHISIIETKDKQRLVAKIERSIAEGHLFAELEAYKHIYKTAGKHPNLANVHGMAVVPYGNRKEEALLMDEVDGWRCSDTLRTLADSWKQGKINSEAYWGTIKFIAHRLLDVTNHLAKAGVVHNDIKPGNVVFDRASGEPVVIDLGLHSRSGEQPKGFTESFKAPELGVGNLGASEKSDVFLVVSTLLHCIEGFEKNPEIKPNQGLRFITSEPAHVMDENGYPIHRPGIAGVETAYTRFITDILGVSADSRPDSNEARLHEFLSDGTIDEESAKQILKDTLTGEMSPLSTDVRRITPKKLRELSDLLRTHLSSAATKQLDMGGVLSDLDTMLVALDKAEREGGVDKDQLKSFNSLILKT |

TABLE 1-continued

| | | |
|---|---|---|
| | | YRVIEDYVKGREGDTKNSSTEVSPYHRSNFMLSIVEPSLQRIQKHLDQTHSFSDIG<br>SLVRAHKHLETLLEVLVTLSQQGQPVSSETYGFLNRLAEAKITLSQQLNTLQQQQE<br>SAKAQLSILINRSGSWADVARQSLQRFDSTRPVVKFGTEQYTAIHRQMMAAHAAIT<br>LQEVSEFTDDMRNFTVDSIPLLIQLGRSSLMDEHLVEQREKLRELTTIAERLNRLE<br>REWM |
| YopM | SEQ ID NO.: 30 | MFINPRNVSNTFLQEPLRHSSNLTEMPVEAENVKSKTEYYNAWSEWERNAPPGNGE<br>QREMAVSRLRDCLDRQAHELELNNLGLSSLPELPPHLESLVASCNSLTELPELPQS<br>LKSLQVENNNLKALPDLPPSLKKLHVRENDLTDLPELPQSLESLRVDNNNLKALSD<br>LPPSLEYLTASSNKLEELPELQNLPFLAAIYADNNLLETLPDLPPSLKKLHVREND<br>LTDLPELPQSLESLQVDNNNLKALSDLPPSLEYLTASSNKLEELPELQNLPFLAAI<br>YADNNLLETLPDLPPHLEILVASYNSLTELPELPQSLKSLRVDNNNLKALSDLPPS<br>LEYLTASSNKLEELPELQNLPFLAAIYADNNLLETLPDLPPSLKKLHVRENDLTDL<br>PELPQSLTFLDVSDNNISGLSELPPNLYYLDASSNEIRSLCDLPPSLVDLNVKSNQ<br>LSELPALPPHLERLIASFNYLAEVPELPQNLKQLHVEQNALREFPDIPESLEELEM<br>DSERVVDPYEFAHETTDKLEDDVFE |
| Amatoxin | SEQ ID NO.: 31 | MSDINATRLPIWGIGCNPCVGDDVTTLLTRGEALC |
| Phallacidin | SEQ ID NO.: 32 | MSDINATRLPAWLVDCPCVGDDVNRLLTRGESLC |
| Killer toxin KP1 | SEQ ID NO.: 33 | MIKPERSILTILIGILCLLAYVLANGEPHDGDNEWSSYCSDQGFRRSDDGLVTTPD<br>VGQESIGKNSINGSELVDYLQCLKVRLNGQKQVVSNDGWLLLLVQEPSVNVTQKAM<br>SECNYNVSSGHKAGSYIQVTNTPADYKVISRRGSYEGDQLPEDVKPYFGVQKTSDY<br>RPISKRINPNLTLRQLAYNFAALNMCSLWCNSCISRSCPYYIAELTVHVNNIHHGT<br>VWLHHFCRNASPQGGNLYSTLTISHKDTAYYVGTGWWKVRSTAATTNDVAGDWYPA<br>SWNQYWCGPHY |
| Killer toxin KP6 | SEQ ID NO.: 34 | MLIFSVLMYLGLLLAGASALPNGLSPRNNAFCAGFGLSCKWECWCTAHGTGNELRY<br>ATAAGCGDHLSKSYYDARAGHCLFSDDLRNQFYSHCSSLNNNMSCRSLSKRTIQDS<br>ATDTVDLGAELHRDDPPPTASDIGKRGKRPRPVMCQCVDTTNGGVRLDAVTRAACS<br>IDSFIDGYYTEKDGFCRAKYSWDLFTSGQFYQACLRYSHAGTNCQPDPQYE |
| Killer Toxin K1 | SEQ ID NO.: 35 | MTKPTQVLVRSVSILFFITLLHLVVALNDVAGPAETAPVSLLPREAPWYDKIWEVK<br>DWLLQRATDGNWGKSITWGSFVASDAGVVIFGINVCKNCVGERKDDISTDCGKQTL<br>ALLVSIFVAVTSGHHLIWGGNRPVSQSDPNGATVARRDISTVADGDIPLDFSALND<br>ILNEHGISILPANASQYVKRSDTAEHTTSFVVTNNYTSLHTDLIHHGNGTYTTFTT<br>PHIPAVAKRYVYPMCEHGIKASYCMALNDAMVSANGNLYGLAEKLFSEDEGQWETN<br>YYKLYWSTGQWIMSMKFIEESIDNANNDFEGCDTGH |
| Killer Toxin K28 (KHR) | SEQ ID NO.: 36 | MGHLAILFSIIAVLNIATAVASSDSIYLKGHRVGQDIDSLYRVYDNGTMYPVTFNE<br>WLNDLTGMNDLATNNATILKRDSSDVSCVTETCQYVDYHVDDEGVITIDISTYRIP<br>VEWDSGSAGNASYGVSKRDTKYETFCKKKICGINVSGFCNAYDFAVHAFDEGGSVY<br>NPVSGITDRIKEATKRDKTECLGYELDHVRIDPAVDWSISISTWKQGSANCDTQAS<br>ADSLKCAAQKALESEHNHQKTAFCIHLDNGGSFNLDIRLISELSFSKYNPWALPCP<br>KYKGSNSWQVVSDCFQ |
| Killer Toxin K28 (KHS) | SEQ ID NO.: 37 | MPRFAIIFALLIAYSLFLSTLFTGSIPDRANTVTSNAPCQVVIWDWIRTRRICNCC<br>SRLCYSLLGRSNLSRTAKRGVCTIAGAVLATAAVIVAAVLVGKSSGSATKRGLTKT<br>ISVLNHTIPFTDHILNGQTLSNGTGSNFVTIGFSGYAVHATIKRASTTDIISWVIP<br>ESMEPTLARVASYVSSSSINLAAVPDTGGNASALSFQNAVQEFATSWVSMTYDQSY<br>GDLRNVANDEGGEEILILMRKRSYRISFQVIETGSTALLLRTRRVVSQLITMTYLV<br>TVQARVGIQIGDIFQHYGGIDNYVMTSISVLRTLEDKAFHENKLLIVREPPNKSNQ<br>DANQSYRLRPFSANDLIQNLKSVDIGFLAFCSFFDKYAHYPEIIMMKITIFISKGN<br>LWSIIYVIQARYVRKRVMKVRGQMPGGLLTNMESLLNIVSTPNLNISEFHIQTHSM<br>SQSKPMYFQKQCYSSQNNIIYIYNSIHITCGAVYVIVHDVRTPSVFVLIELRNCKP<br>LKNSWCETTKTSPRDTKIKKNEYNETVCRRAGALLDGRVRTIRFLMMRTHWSRVKG<br>VSCNTANRLSRFCNHVVSYYPSQNATIHLLPTSLRAESLEQQYTTRPLSSSNNRFC<br>CLKSIFINNCKKACESPSLVSCNLQQTAELLMVYYLYICEACYVSRNHDLLSKQCM<br>STVRAVYVARMRLPKERSTFPCMPRLCWLVNGVVVV |
| Anthrax lethal factor endopeptidase | SEQ ID NO.: 38 | MHVKEKEKNKDENKRKDEERNKTQEEHLKEIMKHIVKIEVKGEEAVKKEAAEKLLE<br>KVPSDVLEMYKAIGGKIYIVDGDITKHISLEALSEDKKKIKDIYGKDALLHEHYVY<br>AKEGYEPVLVIQSSEDYVENTEKALNVYYEIGKILSRDILSKINQPYQKFLDVLNT<br>IKNASDSDGQDLLFTNQLKEHPTDFSVEFLEQNSNEVQEVFAKAFAYYIEPQHRDV<br>LQLYAPEAFNYMDKFNEQEINLSLEELKDQRMLSRYEKWEKIKQHYQHWSDSLSEE<br>GRGLLKKLQIPIEPKKDDIIHSLSQEEKELLKRIQIDSSDELSTEEKEFLKKLQID<br>IRDSLSEEEKELLNRIQVDSSNPLSEKEKEFLKKLKLDIQPYDINQRLQDTGGLID<br>SPSINLDVRKQYKRDIQNIDALLHQSIGSTLYNKIYLYENMNINNLTATLGADLVD<br>STDNTKINRGIFNEFKKNFKYSISSNYMIVDINERPALDNERLKWRIQLSPDTRAG<br>YLENGKLILQRNIGLEIKDVQIIKQSEKEYIRIDAKVVPKSKIDTKIQEAQLNINQ<br>EWNKALGLPKYTKLITFNVHNRYASNIVESAYLILNEWKNNIQSDLIKKVTNYLVD<br>GNGRFVFTDITLPNIAEQYTHQDEIYEQVHSKGLYVPESRSILLHGPSKGVELRND<br>SEGFIHEFGHAVDDYAGYLLDKNQSDLVTNSKKFIDIFKEEGSNLTSYGRTNEAEF<br>FAEAFRLMHSTDHAERLKVQKNAPKTFQFINDQIKFIINS |

TABLE 1-continued

| | | |
|---|---|---|
| Shiga Toxin | SEQ ID NO.: 39 | MKCILLKWVLCLLLGFSSVSYSREFTIDFSTQQSYVSSLNSIRTEISTPLEHISQG TTSVSVINHTPPGSYFAVDIRGLDVYQARFDHLRLIIEQNNLYVAGFVNTATNTFY RFSDFAHISVPGVTTVSMTTDSSYTTLQRVAALERSGMQISRHSLVSSYLALMEFS GNTMTRDASRAVLRFVIVTAEALRFRQIQREFRQALSETAPVYTMTPGDVDLTLNW GRISNVLPEYRGEDGVRVGRISFNNISAILGTVAVILNCHHQGARSVRAVNEESQP ECQITGDRPVIKINNTLWESNTAAAFLNRKSQSLYTTGE |
| Saporin Toxin | SEQ ID NO.: 40 | MKSWIMLVVTWLIILQTTVTAVIIYELNLQGTTKAQYSTFLKQLRDDIKDPNLHYG GTNLPVIKRPVGPPKFLRVNLKASTGTVSLAVQRSNLYVAAYLAKNNNKQFRAYYF KGFQITTNQLNNLFPEATGVSNQQELGYGESYPQIQNAAGVTRQQAGLGIKKLAES MTKVNGVARVEKDEALFLLIVVQMVGEAARFKYIENLVLNNFDTAKEVEPVPDRVI ILENNWGLLSRAAKTANNGVFQTPLVLTSYAVPGVEWRVTTVAEVEIGIFLNVDNN GLPSIIYNNIISGAFGDTY |
| Ricin Toxin | SEQ ID NO.: 41 | MYAVATWLCFGSTSGWSFTLEDNNIFPKQYPIINFTTAGATVQSYTNFIRAVRGRL TTGADVRHDIPVLPNRVGLPINQRFILVELSNHAELSVTLALDVTNAYVVGYRAGN SAYFFHPDNQEDAEAITHLFTDVQNRYTFAFGGNYDRLEQLAGNLRENIELGNGPL EEAISALYYYSTGGTQLPTLARSFIICIQMISEAARFQYIEGEMRTRIRYNRRSAP DPSVITLENSWGRLSTAIQESNQGAFASPIQLQRRNGSKFSVYDVSILIPIIALMV YRCAPPPSSQFSLLIRPVVPNFNADVCMDPEPIVRIVGRNGLCVDVRDGRFHNGNA IQLWPCKSNTDANQLWTLKRDNTIRSNGKCLTTYGYSPGVYVMIYDCNTAATDATR WQIWDNGTIINPRSSLVLAATSGNSGTTLTVQTNIYAVSQGWLPTNNTQPFVTTIV GLYGLCLQANSGQVWIEDCSSEKAEQQWALYADGSIRPQQNRDNCLTSDSNIRETV VKILSCGPASSGQRWMFKNDGTILNLYSGLVLDVRRSDPSLKQIILYPLHGDPNQI WLPLF |

In some embodiments, the death agent is an overexpressed product of genetic element selected from DNA or RNA. In some embodiments, the genetic element is a Growth Inhibitory (GIN) sequence such as GIN11.

In some embodiments, the death agent is a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, or any combination thereof. In some embodiments, the ribosomally encoded death agent is Cholera toxin, SpvB toxin, CARDS toxin, SpyA Toxin, HopU1, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, or any combination thereof.

Along with one or more positive selection markers, a plasmid (such as PLASMID 2) can also include one or more negative selection markers under control of a different DNA binding sequence to enable binary selection. The plasmid (e.g., PLASMID 2) can encode for one or more of negative selection markers in Table 1 driven by a promoter which depends on the DBD present in the PPI integration plasmid—DNA Binding Sequence (DBS), for example, the LexAop sequence (DBS) which can become bound by LexA (DBD). In some embodiments, to ensure repression of the 'death agents,' the plasmid (e.g., PLASMID 2) can include a silencing construct such as a TetR'-Tup11 fusion driven by a strong promoter (such as ADH1) to bind the DBD and silence transcription in the presence of doxycycline. The plasmid (e.g., PLASMID 2) can comprise bacterial selection and propagation markers (i.e. ori and AmpR), and yeast replication and selection markers (i.e. LEU2 and CEN or 2 um) as well.

Figure 7:
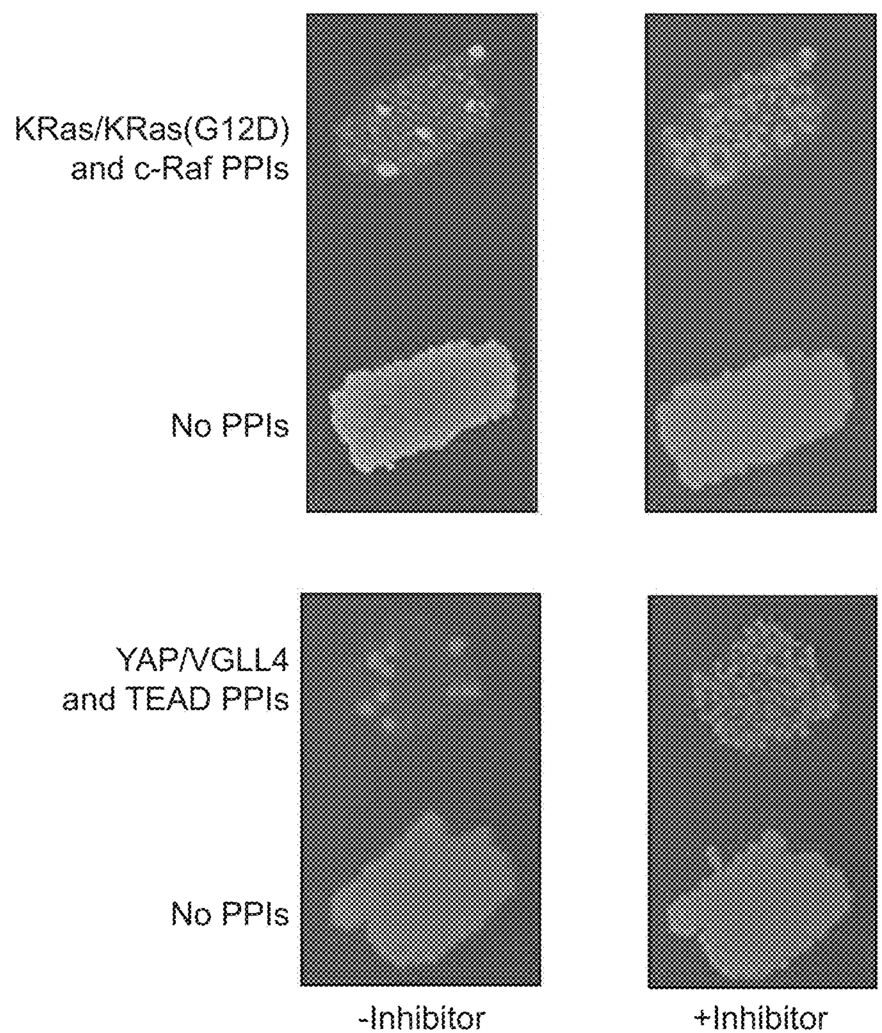
FIG. 7 illustrates two platforms to identify a compound that specifically disrupts a protein-protein interaction in cell culture by selecting for cytotoxic reporter.

FIG. 7 shows two platforms to identify a disrupting compound in cell culture using both a negative and a positive selection marker. In the first platform, KRas and KRas(G12D) fused to DBDs and c-Raf fused to AD were expressed in yeast cells. In the absence of inhibitors, the KRas(G12D) and c-Raf maintain an interaction to drive expression of a cytotoxic reporter, resulting in a low amount of cell growth/survival. A nutritional reporter was controlled by KRas and c-Raf interaction. The cells were patched onto selective media for a nutritional marker with or without inhibitor and visualized after 4 days of growth at 30° C. In cell populations with KRas(G12D) and c-Raf interaction, only those with the inhibitor showed enhanced cell viability, illustrating the specificity of the inhibitor for the KRas (G12D) and c-Raf interaction.

In the second platform, VGLL4 and YAP fused to DBDs and TEAD fused to AD were expressed in cells. In the absence of inhibitors, the YAP and TEAD maintain an interaction to drive expression of cytotoxic reporter. A nutritional reporter was controlled by VGLL4 and TEAD interaction. The cells were patched onto selective media for a nutritional marker with or without inhibitor and visualized after 4 days of growth at 30° C. In cell populations with YAP and TEAD interaction, only those with the inhibitor showed enhanced cell viability, illustrating the specificity of the disruptor to YAP and TEAD interaction.

In some embodiments, the host cell can further comprises more than one sequence for expressing a positive control reporter that is activated by a promoter DNA sequence specific for a DNA binding moiety. In some embodiments, the host cell further comprises more than one sequence for expressing a death agent that is activated by a promoter DNA sequence specific for a DNA binding moiety.

Figure 4A:
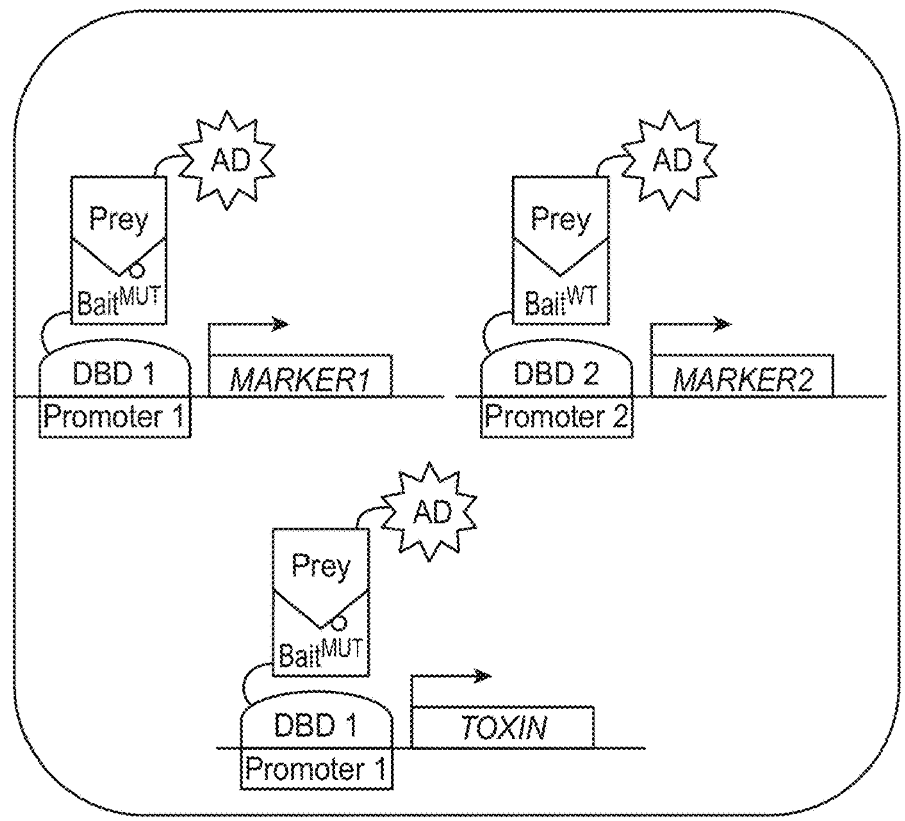
FIGS. 4A and 4B show an embodiment of a platform to identify a compound that specifically disrupts a protein-protein interaction, where the platform includes two positive selection markers and a negative selection markers. In these figures, the compound may interact with the prey to disrupt the prey-bait interaction.
Figure 4B:
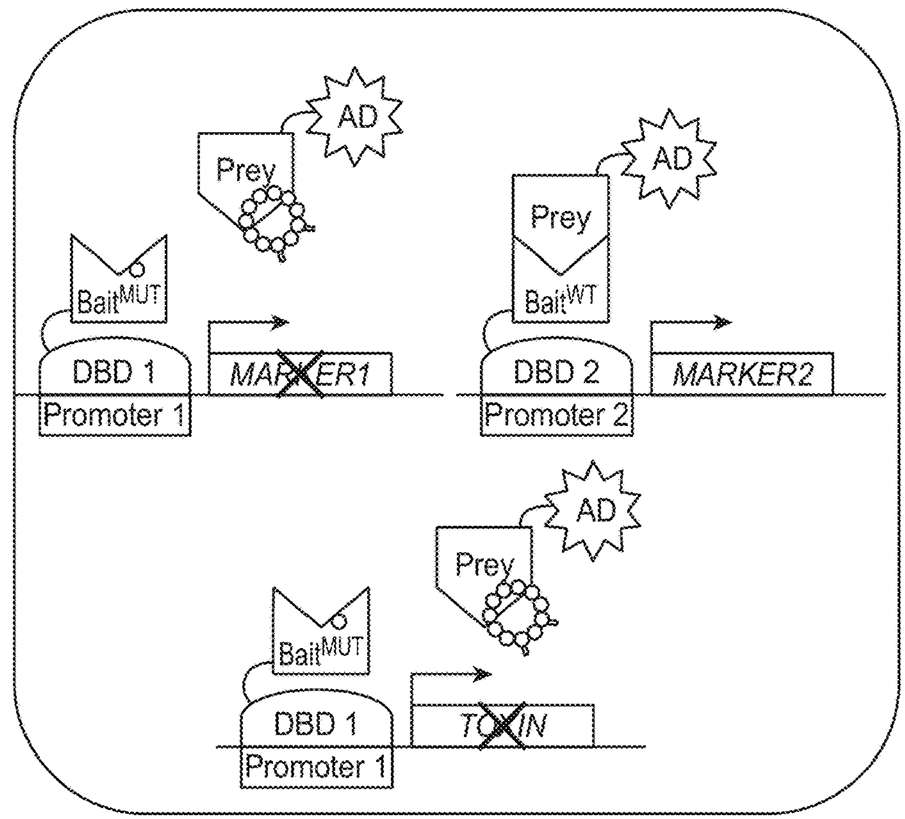

FIGS. 4A and 4B illustrate a platform with more than one positive selection markers and a negative selection marker for identifying a compound that disrupts a protein-protein interaction within a complex in a specific manner. The multiple selection markers can reduce false positive rate due to mutations that leads to avoidance of selection. DBD1 and DBD2 are promoter specific DNA-binding domains. AD refers to an activation domain. Prey, BaitWT, and BaitMut refer to three proteins, wherein BaitWT and BaitMut each interacts with Prey. Broken arrows indicate active expression of the reporter. Markers 1 and 2 refer to positive selection markers, toxins refers to death agent. The ring comprising smaller circular items illustrates a potential inhibitor (e.g., a randomly produced peptide). Two scenarios are shown; FIG. 4A illustrates a case where a peptide is unable to disrupt the pairwise interaction of interest, and death agent is expressed, leading to cell death. FIG. 4B illustrates a case where a peptide is able to disrupt the Prey and BaitMut interaction by acting on the Prey without disrupting the BaitWT and Prey interaction. Peptide disruption activity is assayed by survival, and specificity is assayed by growth on the expressed positive selection reporter, marker 2.

Figure 5A:
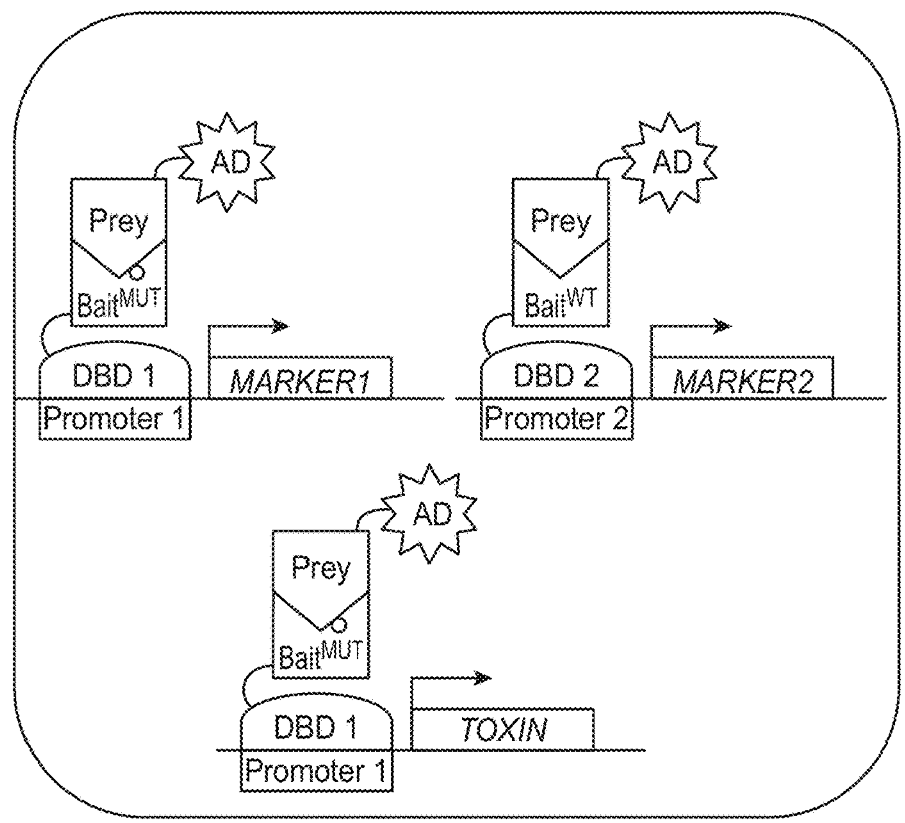
FIGS. 5A and 5B show an embodiment of a platform to identify a compound that specifically disrupts a protein-protein interaction in a system with two positive selections and a negative selection. In contrast with FIGS. 4A and 4B, in these figures, the compound may act on the bait (rather than the prey) to disrupt the prey-bait interaction.
Figure 5B:
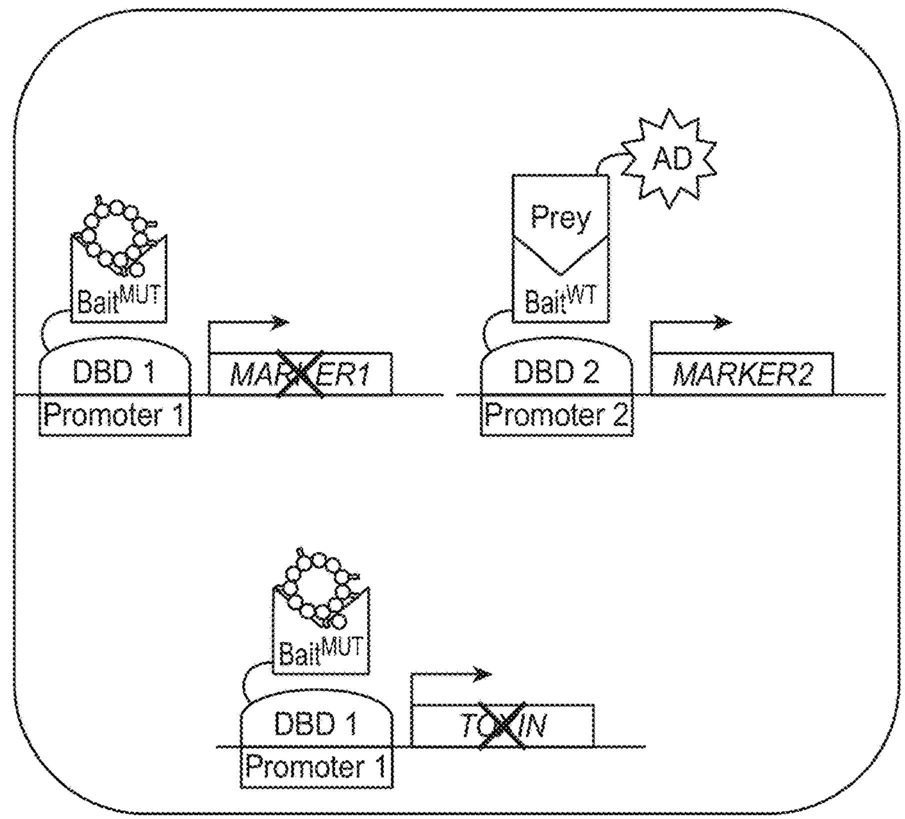

FIGS. 5A and 5B show a platform that is analogous to the platform of FIGS. 4A and 4B, where the inhibitor binds to the bait instead of the prey. More specifically, the platform of FIGS. 5A and 5B has more than one positive selection marker and one negative selection marker for identifying a compound that disrupts a protein-protein interaction within a complex in a specific manner. The multiple selection markers can reduce false positive rate due to mutations that leads to avoidance of selection. DBD1 and DBD2 are promoter specific DNA-binding domains. AD refers to an activation domain. Prey, BaitWT, and BaitMut refer to three proteins, wherein BaitWT and BaitMut each interacts with Prey. Broken arrows indicate active expression of the reporter. Markers 1 and 2 refers to positive selection markers, toxins refers to death agent. The ring comprising smaller circular items illustrates a randomly produced peptide. Two scenarios are shown; FIG. 5A illustrates a case where a peptide is unable to disrupt the pairwise interaction of interest, and death agent is expressed, leading to cell death. FIG. 5B illustrates a case where a peptide is able to disrupt the Prey and BaitMut interaction by acting on the BaitMut without disrupting the BaitWT and Prey interaction, and peptide disruption activity is assayed by survival and specificity is assayed by growth on the expressed positive selection reporter, marker 2.

A plasmid (e.g., PLASMID 3) can be used to confirm expression of the reporters and the successful construction of the strains. PLASMID 3 can include a direct fusion between the AD and one or multiple DBDs. The plasmid (e.g., PLASMID 3) can further include bacterial selection and propagation markers (i.e. ori and AmpR), and yeast replication and selection markers (i.e. TRP1 and CEN or 2 um).

FIG. 10 illustrates a confirmation plasmid. The depicted plasmid show the integration of two bait-prey fusion proteins, each with its own DBD. Protein tags may be included to enable detection of the proteins. The plasmid may also include propagation and selection markers for growth in hosts.

Disclosed herein, in certain embodiments, is a library of plasmid vectors, each plasmid vector comprising a DNA sequence encoding a different peptide sequence operably linked to a first switchable promoter; a DNA sequence encoding a death agent under control of a second switchable promoter; and a DNA sequence encoding a positive selection reporter under control of a third switchable promoter.

Addition or Expression of Modulators

A molecule from a library that can selectively disrupt or facilitate PPI of interest can be screened by via use of positive and/or negative selection markers in a host cell.

In some embodiments, the molecule is small molecule. In some embodiments, the small molecule is peptidomimetic. The host cell can be made to become permeabilized to small molecules, for example by deletion of drug efflux pumps, such as PDR5, ERG6, or 12geneΔ0HSR (*Chinen,* 2011), to enable a small molecule screening approach. The host cell can additionally carry mutations to enable more efficient transformation with vectors and/or more efficient uptake small molecules.

In other embodiments, the molecule is peptide or protein. In some embodiments, the peptide or protein is derived from naturally occurring protein product. In another embodiment, the peptide or protein is synthesized protein product. In other embodiments, the peptide or protein is a product of recombinant genes.

In some embodiments, the molecule is introduced to the host cell exogenously. In other embodiments, the molecule is the expression product of test DNA inserted into the host cell, wherein the test DNA comprises of DNA sequences that encodes a polypeptide. Libraries can be formed by delivery of a plurality of test DNA molecules into host cells. In some embodiments, the peptide sequences of the polypeptides in the library are random. In some embodiments, the different peptide sequences are pre-enriched for binding to a target.

To screen for peptides that selectively disrupt or facilitate a PPI of interest, peptides from a randomized peptide library can be applied to the host cell. PLASMID 2 can be further used to express a randomized peptide library (such as a randomized NNK 60-mer sequences). PLASMID 2 can include a restriction site for integration of a randomized peptide library driven by a strong promoter (such as the ADH1 promoter) or an inducible promoter (such as the GAL1 promoter).

In some embodiments, the randomized peptide library is about 60-mer. In some embodiments, the randomized peptide library is from about 5-mer to 20-mer. In some embodiments, the randomized peptide library is less than 15-mer.

The library can also initiate with a fixed sequence of, for example, Methionine-Valine-Asparagine (MVN) for N-terminal stabilization and/or another combination of high-half-life N-end residues (see, for e.g., Varshavsky. Proc. Natl. Acad. Sci. USA. 93:12142-12149 (1996)) to maximize the half-life of the peptide, and terminate with the 3'UTR of a short protein (such as sORF1). The peptide can also be tagged with a protein tag such as Myc. In some embodiments, N-terminal residues of the peptide comprise Met, Gly, Ala, Ser, Thr, Val, or Pro or any combination thereof to minimize proteolysis.

The plurality of different short peptide sequences can be randomly generated by any method (e.g. NNK or NNN nucleotide randomization). The plurality of different short peptide sequences can also be preselected, either by previous experiments selecting for binding to a target, or from existing data sets in the scientific literature that have reported rationally-designed peptide libraries.

In some embodiments, the library comprises polypeptides about 60 amino acids or fewer in length. In another embodiment, the library comprises polypeptides about 30 or fewer amino acids in length. In another embodiment, the library comprises polypeptides about 20 or fewer amino acids in length.

Modification of Disrupting or Facilitating Peptides

The peptide that disrupts or facilitates PPI can also be a product of post-translational modification. The post-translational modification can include any one or combination of cleavage, cyclization, bi-cyclization, methylation, halogenation, glycosylation, acylation, phosphorylation, and acetylation. In some embodiments, the methylation comprises reacting with an N-methyltransferase. In some embodiments, the post-translational modification is done by naturally occurring enzymes. In some embodiments, the post-translational modification is done by synthetic enzymes. In some embodiments, the synthetic enzymes are chimeric.

The peptide can be ribosomally synthesized and post-translationally modified peptide (RiPP) whereby the core peptide is flanked by prepropeptide sequence comprising a leader peptide and recognition sequences which signal for the recruitment of maturation, cleavage, and/or modifying enzymes such as excision or cyclization enzymes including, for example, lanthipeptides maturation enzymes from *Lactococcus lactis* (LanB, LanC, LanM, LanP) patellamide biosynthesis factors from cyanobacteria (PatD, PatG), butelase 1 from *Clitoria ternatea*, and POPB from *Galerina marginata, Lentinula edodes, Omphalotacae olearis, Dendrothele bispora*, or *Amanita bisporigera*, or other species. In some embodiments, the cyclization or bicyclization enzymes are synthetic chimeras.

Figure 11:
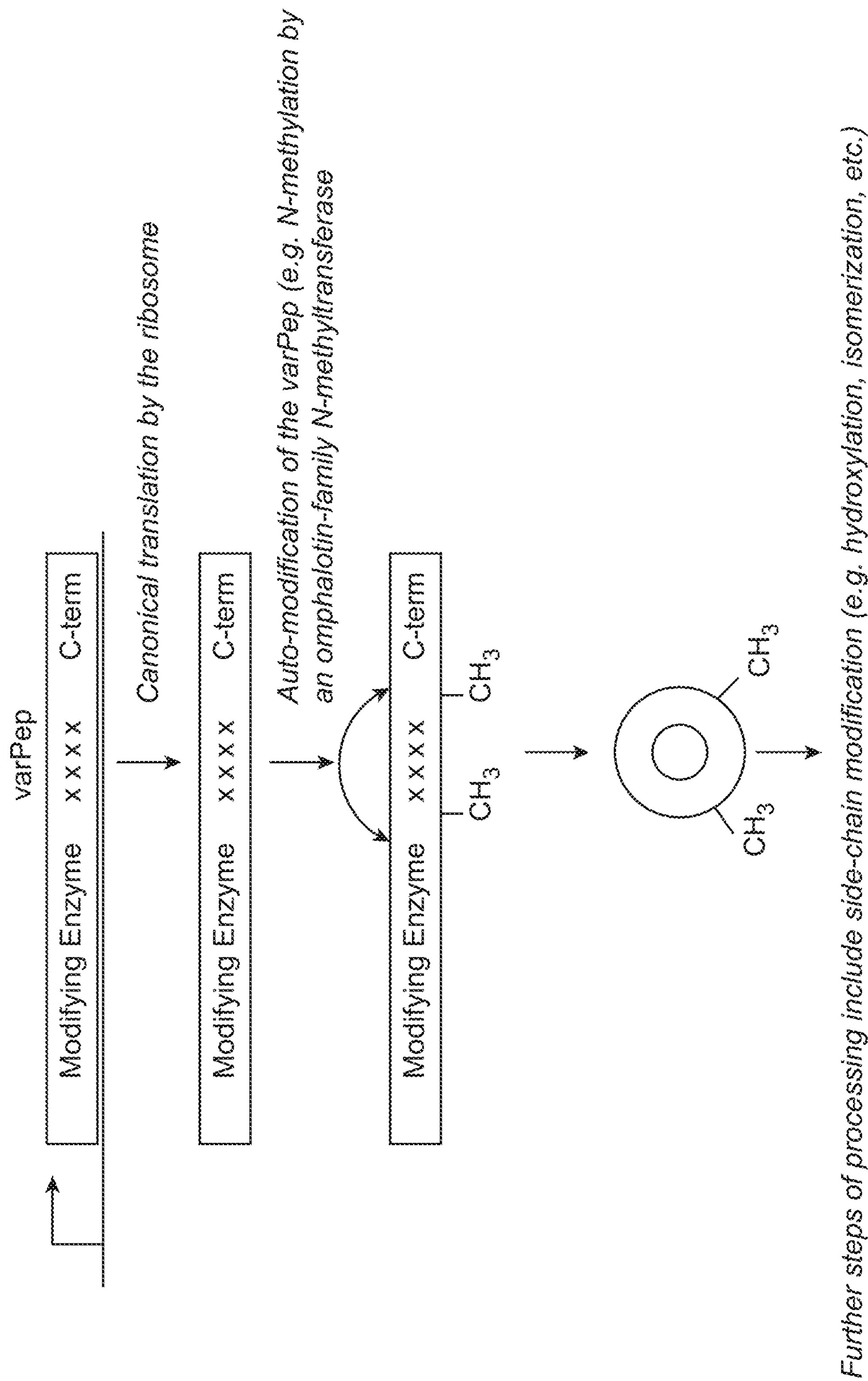
FIG. 11 illustrates a cyclization process of families of RiPP scaffolds that lead to the generation of N-to-C cyclized, backbone N-methylated macrocycles by the action of (1) prolyl oligopeptidases belonging to the PopB family and (2) N-methyltransferases belonging to the omphalotin methyltransferase family. The variable peptide library region is embedded within the primary sequence of the modifying enzyme. N- and C-term sequences refer to consensus binding and processing recognition elements. The N-terminus comprises the enzymatic N-methyltransferase domain, a linker region, and the processing enzymes binding sites.

In one example, as illustrated in FIG. 11, the variable peptide library region is embedded within the primary sequence of a modifying enzyme (e.g., the homolog of the omphalotin N-methyltransferase enzyme from *Dendrothele bispora, Marasmius fiardii, Lentinula edodes, Fomitiporia mediterranea, Omphalotus olearius* or other) and contains random residues, some of which may be post-translationally decorated by additional modifications like hydroxylation, halogenation, glycosylation, acylation, phosphorylation, methylation, acetylation. This diversified variable region is excised and modified to form N-to-C cyclized, optionally backbone N-methylated macrocycles by the action of a prolyl endopeptidase belonging to the PopB family and N-methyltransferases belonging to the omphalotin methyltransferase family. An exemplary list of prolyl endopeptidases is shown in Table 2. An exemplary list of N-methyltransferases is shown in Table 3.

TABLE 2

| Amino acid sequences of prolyl endopeptidase type cyclizing enzymes | | |
|---|---|---|
| *Galerina marginata* CBS 339.88 | SEQ ID NO.: 42 KDR68475.1 hypothetical protein GALMADRAFT_78538 | MSSVTWAPGNYPSTRRSDHVDTYQSASKGEVPVPDPYQWLEESTDEVDKW<br>TTAQADLAQSYLDQNADIQKLAEKFRASRNYAKFSAPTLLDDGHWYWFYN<br>RGLQSQSVLYRSKEPALPDFSKGDDNVGDVFFDPNVLAADGSAGMVLCKF<br>SDGKFFAYAVSHLGGDYSTIYVRSTSSPLSQASVAQGVDGRLSDEVKWF<br>KFSTIIWTKDSKGFLYQRYPARERHEGTRSDRNAMMCYHKVGTTQEEDII<br>VYQDNEHPEWIYGADTSEDGKYLYLYQFKDTSKKNLLWVAELDEDGVKSG<br>IHWRKVVNEYAADYNIITNHGSLVYIKTNLNAPQYKVITIDLSKDEPEIR<br>DFIPEEKDAKLAQVNCANEEYFVAIYKRNVKDEIYLYSKAGVQLTRLAPD<br>FVGAASIANRQKQTHFFLTLSGFNTPGTIARYDFTAPETQRFSILRTTKV<br>NELDPDDFESTQVWYESKDGTKIPMFIVRHKSTKFDGTAAAIQYGYGGFA<br>TSADPFFSPIILTFLQTYGAIFAVPSIRGGGEFGEEWHKGGRRETKVNTF<br>DDFIAAAQFLVKNKYAAPGKVAINGASNGGLLVMGSIVRAPEGTFGAAVP<br>EGGVADLLKFHKFTGGQAWISEYGNPSIPEEFDYIYPLSPVHNVRTDKVM<br>PATLITVNIGDGRVVPMHSFKFIATLQHNVPQNPHPLLIKIDKSWLGHGM<br>GKPTDKNVKDAADKWGFIARALGLELKTVE |
| *Amanita bisporigera* | SEQ ID NO.: 43 ADN19205.1 prolyl oligopeptidase | MPPTPWAPHSYPPTRRSDHVDVYQSASRGEVPVPDPYQWLEENSNEVDEW<br>TTAQTAFTQGYLDKNADRQKLEEKFRASKDYVKFSAPTLLDSGHWYWFYN<br>SGVQSQAVLYRSKKPVLPDFQRGTRKVGEVYFDPNVLSADGTAIMGTCRF<br>SPSGEYFAYAVSHLGVDYFTIYVRPTSSSLSQAPEAEGGDGRLSDGVKWC<br>KFTTITWTKDSKGFLYQRYPARESLVAKDRDKDAMVCYHRVGTTQLEDII<br>VQQDKENPDWTYGTDASEDGKYIYLVVYKDASKQNLLWVAEFDKDGVKPE<br>IPWRKVINEFGADYHVITNHGSLIYVKTNVNAPQYKVVTIDLSTGEPEIR<br>DFIPEQKDAKLTQVKCVNKGYFVAIYKRNVKDEIYLYSKAGDQLSRLASD<br>FIGVASITNREKQPHSFLTFSGFNTPGTISRYDFTAPDTQRLSILRTTKL<br>NGLNADDFESTQVWYKSKDGTKVPMFIVRHKSTKFDGTAPAIQNGYGGFA<br>ITADPFFSPIMLTFMQTYGAILAVPNIRGGGEFGGEWHKAGRRETKGNTF<br>DDFIAAAQFLVKNKYAAPGKVAITGASNGGFLVCGSVVRAPEGTFGAAVS<br>EGGVADLLKFNKFTGGMAWTSEYGNPFIKEDFDFVQALSPVHNVPKDRVL<br>PATLLMTNAGDDRVVPMHSLKFVANLQYNVPQNPHPLLIRVDKSWLGHGF<br>GKTTDKHTKDAADKWSFVAQSLGLEWKTVD |
| *Hypsizygus marmoreus*] | SEQ ID NO.: 44 KYQ30898.1 Prolyl endopeptidase | MAISPTPWTPNTYPPTRRSSHVDIYKSATRGEVRVADPYQWLEENTEETD<br>KWTTAQEEFTRSYLDKNTDRQRLEDAFRTSTDYAKFSSPTLYEDGRWYWF<br>YNSGLQPQPLIYRSKGKTLPDFSQDDNVVGEVFFDPNLLSDDGTAALSIY<br>DFSDCGKYFAYGISFSGSDFSTIYVRSTESPLAKKNSGSTDDDRLSDEIK<br>HVKFSAVTWTKDSKGFFYQRYPAHENAKEGIETGGDVDAMIYYHVIGTSQ<br>SEDILVHSDKSNPEWMWSIDITEDGKYLILYTMKDSSRKNLMWIAELSKN<br>EIGPNIQWNKIIDVFDAEYHLITNDGPILYVKTNADAPQYKLVTMDISGD<br>KDISRDLIPEDKNANLVQVDCVNRDTFAVIYKRNVKDEIYLYSKTGIQLS<br>RLASDFVGAASISSREKQPHFFVTMTGFSTPGTVARYDFGAPEEQRWSIY<br>RSVKVNGLNPDDFESKQVWYESKDGTKIPMFIVRHKATKFDGTAPAIQYG<br>YGGFSISINPFFSPTILTFLQTYGAVLAVPNIRGGAEFGEDWHKAGTREK<br>KGNVFDDFVAATQYLVKNKYAGEGKVAINGGSNGGLLVGACINRAPEGTF<br>GAAVAEVGVMDLLKFSKFTIGKAWTSDYGDPDDPKDFDFICPLSPLHNIP<br>TDRVLPPTMLLTADHDDRVVPMHSFKHAATLQYTLPHNPHPLVIRIDKKA<br>GHGAGKSTEKRIKESADKWGFVAQSLGLVWQEPA |
| *Conocybe apala* | SEQ ID NO.: 45 ACQ65797.1 prolyl oligopeptidase | MPPSTPNEYPPTRRSDDVLTYRSEKNGEVVVPDPYQWLEHNTEETDKWTT<br>AQAAFTRAHLDKNPKRNALEEAFTAANDYAKFSAPQLHDDGRWYWYYNTG<br>LQAQTCLWRTRDDTIPDFSKQLDEDVGEIFFDPNALSKDGTAALSTYRFS<br>RDGKYFAYAIAQSGSDFNTIYVRPTDSPLTKRDESGRDPSRLADEVKFVK<br>FSGITWAPNSEGFFYQRYPHIDGATLEEGGIATRRDLHAMVYYHRVGTPQ<br>SEDILIHRDPANPEWMFGVNVTDNGEYIELYISKDSSRKNMLWVANFAMN<br>KIGEQFQWRKVINDFAAEYDVITNHGPVYYFRTDDGAPKHKILSINIDTN<br>ERKLLVPESEDAALFSTVCVNKNYMALIYKRNVKDEVHLYTLEGKPVRRL |

TABLE 2-continued

| Amino acid sequences of prolyl endopeptidase type cyclizing enzymes | | |
|---|---|---|
| | | AEDFVGACTISGKEKQPWFFVTMSGFTSPSTVGRYNFQIPEEENRWSIFR AAKIKNLNPNDFEASQVWYKSKDGTNVPMFIVRHKSTQFDGTAPALQYGY GGFSISIDPFFSASILTFLKVYGAILVVPSIRGGNEFGEEWHRGGMKQNK VNCFDDFIAATNHLVEHKYAAPGKVAINGGSNGGLLVAACINRAPEGTFG AAIAEVGVHDMLKFHKFTIGKAWTSDYGNPDDPHDFDYIYPISPVHNVPT DKILPPTLLLTADHDDRVVPMHTFKLAATLQHTLPHNPHPLLLRVDKKAG HGAGKPLQLKIREQADKWGFVAQSFQLVWRDGV |
| *Amanita bisporigera* | SEQ ID NO.: 46 GenBank HQ225841.1 POPB | MPPTPWAPHSYPPTRRSDHVDVYQSASRGEVPVPDPYQWLEENSNEVDEW TTAQTAFTQGYLDKNADRQKLEEKFRASKDYVKFSAPTLLDSGHWYWFYN SGVQSQAVLYRSKKPVLPDFQRGTRKVGEVYFDPNVLSADGTAIMGTCRF SPSGEYFAYAVSHLGVDYFTIYVRPTSSSLSQAPEAEGGDGRLSDGVKWC KFTTITWTKDSKGFLYQRYPARESLVAKDRDKDAMVCYHRVGTTQLEDII VQQDKENPDWTYGTDASEDGKYIYLVVYKDASKQNLLWVAEFDKDGVKPE IPWRKVINEFGADYHVITNHGSLIYVKTNVNAPQYKVVTIDLSTGEPEIR DFIPEQKDAKLTQVKCVNKGYFVAIYKRNVKDEIYLYSKAGDQLSRLASD FIGVASITNREKQPHSFLTFSGFNTPGTISRYDFTAPDTQRLSILRTTKL NGLNADDFESTQVWYKSKDGTKVPMFIVRHKSTKFDGTAPAIQNGYGGFA ITADPFFSPIMLTFMQTYGAILAVPNIRGGGEFGGEWHKAGRRETKGNTF DDFIAAAQFLVKNKYAAPGKVAITGASNGGFLVCGSVVRAPEGTFGAAVS EGGVADLLKFNKFTGGMAWTSEYGNPFIKEDFDFVQALSPVHNVPKDRVL PATLLMTNAGDDRVVPMHSLKFVANLQYNVPQNPHPLLIRVDKSWLGHGF GKTTDKHTKDAADKWSFVAQSLGLEWKTVD |
| *Lentinula edodes* | SEQ ID NO.: 47 GenBank GAW09065.1 The DOE Joint Genome Institute (JGI) 011197; LENED_011197) | MFSATQESPTMSVPQWDPYPPVSRDETSAITYQSKLCGSVTVRDPYSALE VPFDDSEETKAFVHAQRKFARTYLDEIPDRETWLQTLKESWNYRRFTVPK RESDGYTYFEYNDGLQSQMSLRRVKVSEEDTILTESGPGGELFFDPNLLS LDGNAALTGSMMSPCGKYWAYGVSEHGSDWMTTYVRKTSSPHMPSQEKGK DPGRMDDVIRYSRFFIVYWSSDSKGFFYSRYPPEDDEGKGNTPAQNCMVY YHRLGEKQEKDTLVYEDPEHPFWLWALQLSPSGRYALLTASRDASHTQLA KIADIGTSDIQNGIQWLTIHDQWQARFVIIGDDDSTIYFMTNLEAKNYLV ATLDIRHSEAGVKTLVAENPDALLISASILSTDKLVLVYLHNARHEIHVH DLNTGKPIRQIFDNLIGQFSLSGRRDDNDMFVFHSGFTSPGTIYRFRLNE DSNKGTLFRAVQVPGLNLSDFTTESVFYPSKDGTPIHMFITRLKDTPVDG TAPVYIYGYGGFALAMLPTFSVSTLLFCKIYRAMYVVPNIRGGSEFGESW HREGMLDKKQNVFDDFNAATKWLVANKYANKYNVAIRGGSNGGVLTTACA NQAPELYRCVITIGGIIDMLRFPKFTFGALWRSEYGDPEDPEDFDFIYKY SPYHNIPSGDVVLPAMLFFTAAYDDRVSPLHSFKHVAALQYNFPNGPNPV LMRIDLNTGHFAGKSTQKMLEETADEYRCDLLCCNLQL |
| *Omphalotacae olearis* | SEQ ID NO.: 48 The DOE Joint Genome Institute (JGI) 2090; OMPOL1_2090 | MSFPGWGPYPPVERDETSAITYSSKLHGSVTVRDPYSQLEVPFEDSEETK AFVHSQRKFARTYLDENPDREAWLETLKKSWNYRRFSALKPESDGHYYFE YNDGLQSQLSLYRVRMGEEDTVLTESGPGGELFFNPNLLSLDGNAALTGF VMSPCGNYWAYGVSEHGSDWMSIYVRKTSSPHLPSQERGKDPGRMNDKIR HVRFFIVSWTSDSKGFFYSRYPPEDDEGKGNAPAMNCMVYYHRIGEDQES DVLVHEDPEHPFWISSVQLTPSGRYILFAASRDASHTQLVKIADLHENDI GTNMKWKNLHDPWEARFTIVGDEGSKIYFMTNLKAKNYKVATFDANHPDE GLTTLIAEDPNAFLVSASIHAQDKLLLVYLRNASHEIHIRDLTTGKPLGR IFEDLLGQFMVSGRRQDNDIFVLFSSFLSPGTVYRYTFGEEKGHSSLFRA ISIPGLNLDDFMTESVFYPSKDGTSVHMFITRPKDVLLDGTSPVLQYGYG GFSLAMLPTFSLSTLLFCKIYRAIYAIPNIRGGSEYGESWHREGMLDKKQ NVFDDFNAATEWLIANKYASKDRIAIRGGSNGGVLTTACANQAPGLYRCV ITIEGIIDMLRFPKFTFGASWRSEYGDPEDPEDFDFIFKYSPYHNIPPPG DTIMPAMLFFTAAYDDRVSPLHTFKHVAALQHNFPKGPNPCLMRIDLNSG HFAGKSTQEMLEETADEYRLKVQ |

TABLE 3

| Amino acid sequences of N-methyltransferases | | |
|---|---|---|
| *Lentinula edodes* | SEQ ID NO.: 49 GenBank GAW09067.1 The DOE Joint Genome Institute (JGI) 011194; LENED_011194) | METPTLNKSGSLTIVGTGIESIGQMTLQTLSYIEAADKVFYCVIDPATEAF ILTKNKDCVDLYQYYDNGKSRMDTYTQMSEVMLREVRKGLDVVGVFYGHPG VFVNPSLRALAIAKSEGFKARMLPGVSAEDCLYADLCIDPSNPGCLTYEAS DFLIRERPTNIYSHFILFQVGCVGIADFNFTGFENSKFGILVDRLEKEYGA EHPVVHYIAAMLPHEDPVTDQWTIGQLREPEFYKRVGGVSTFYIPPKERKE INVDIIRELKFLPEGKVPDTRTQIYPPNQWEPEVPTVPAYGSNEHAAIAQL DTHTPPEQYQPLATSKAMTDVMTKLALDPKALAEYKADHRAFAQSVPDLTA NERTALEIGDSWAFRCAMKEMPISLLDNAKQSMEEASEQGFPWIIVVGVVG VVGSVVSSA |

TABLE 3-continued

| Amino acid sequences of N-methyltransferases | | |
|---|---|---|
| *Omphalotacae olearis* | SEQ ID NO.: 50 The DOE Joint Genome Institute (JGI) 2087; OMPOL1_2087 | METSTQTKAGSLTIVGTGIESIGQMTLQALSYIEAAAKVFYCVIDPATEAF<br>ILTKNKNCVDLYQYYDNGKSRLNTYTQMSELMVREVRKGLDVVGVFYGHPG<br>VFVNPSHRALAIAKSEGYRARMLPGVSAEDCLFADLCIDPSNPGCLTYEAS<br>DFLIRDRPVSIHSHLVLFQVGCVGIADFNFTGFDNNKFGVLVDRLEQEYGA<br>EHPVVHYIAAMMPHQDPVTDKYTVAQLREPEIAKRVGGVSTFYIPPKARKA<br>SNLDIIRRLELLPAGQVPDKKARIYPANQWEPDVPEVEPYRPSDQAAIAQL<br>ADHAPPEQYQPLATSKAMSDVMTKLALDPKALADYKADHRAFAQSVPDLTP<br>QERAALELGDSWAIRCAMKNMPSSLLDAARESGEEASQNGFPWVIVVGVIG<br>VIGSVMSTE |
| *Dendrothele bispora* | SEQ ID NO.: 51 The DOE Joint Genome Institute (JGI) 765759 | MESSTQTKPGSLIVVGTGIESIGQMTLQALSYIEAASKVFYCVIDPATEAF<br>ILTKNKNCVDLYQYYDNGKSRMDTYTQMAELMLKEVRNGLDVVGVFYGHPG<br>VFVNPSHRALAIARSEGYQARMLPGVSAEDCLFADLCIDPSNPGCLTYEAS<br>DELIRERPVNVHSHLILFQVGCVGIADFNFSGFDNSKFTILVDRLEQEYGP<br>DHTVVHYIAAMMPHQDPVTDKFTIGQLREPEIAKRVGGVSTFYIPPKARKD<br>INTDIIRLLEFLPAGKVPDKHTQIYPPNQWEPDVPTLPPYGQNEQAAITRL<br>EAHAPPEEYQPLATSKAMTDVMTKLALDPKALAEYKADHRAFAQSVPDLTP<br>QERAALELGDSWAIRCAMKNMPSSLLEAASQSVEEASMNGFPWVIVTGIVG<br>VIGSVVSSA |
| *Rhizopogon vinicolor* | SEQ ID NO.: 52 GenBank AM-OR11-026; OAX31299.1 | MTTDTKRGTLTIAGSGIASIAHITLETLSYIKESDKLFYLVCDPVTEAFIQ<br>DNATGDFFDLSVFYDKNKSRYDSYIQMCEIMLRAVRAGHSVLGIFYGHPGV<br>FVSPSHRAIAVAREEGYKARMLPGVSAEDYMFADLEFDPSQSTCNTYEATE<br>LLLRDRPLDPAIQNIIWQVGSVGVVDMEFEKSKFHLLVDRLEQDFGPDHKV<br>VHYIGAVLPQSTTTMDIFTISDLRKENVAKQFGTISTLYIPPRDEGPVSSS<br>MTQAFDFKAGAMVYSPVKWAGPKLNIVSALSPYERDVISQIDTHVAPEGYK<br>ILHTSAAMNKFMTDLSLKPKFLEEYKLYPEAVVESAEGLSNLEKFGLKFGS<br>DGAVYILMKATESDIASGRQLTEDEIAKAHKSVGFPTVLVILPTVIVVLIG<br>RE |
| *Rhizopogon vinicolor* | SEQ ID NO.: 53 GenBank AM-OR11-026; OAX32862.1 | MSTKRGTLTIAGSGIASVGHITLGTLSYIKESDKIFYLVCDPVTEAFIYDN<br>STADCFDLSVFYDKTKGRYDSYIQMCEVMLKAVRAGHDVLGVFYGHPGVFV<br>SPSHRAIAVARQEGYKAKMLPGISAEDYMFADLEFDPSVSGCKTCEATEIL<br>LRDKPLDPTIQNIIWQVGSVGVVDMEFSKSKFQLLVDRLEKDFGPDHKVVH<br>YIGAVLPQSTTTMDTFTIADLRKEDVAKQFGTISTLYIPPRDEGHVNLSMA<br>KVFGGPGASVKLNDSIKWAGPKLNIVSANDPHERDVIAQVDTHVAPEGHKK<br>LRVSAAMKKFMTDLALKPKFLEEYKLDPVAVVESAEGLSNLERFGLKFARS<br>GPADALMKATESDIASGRQLTEEEIAQGTGPVGLQTALALLVLLGLGVAIV<br>TRPDD |

Figure 12:
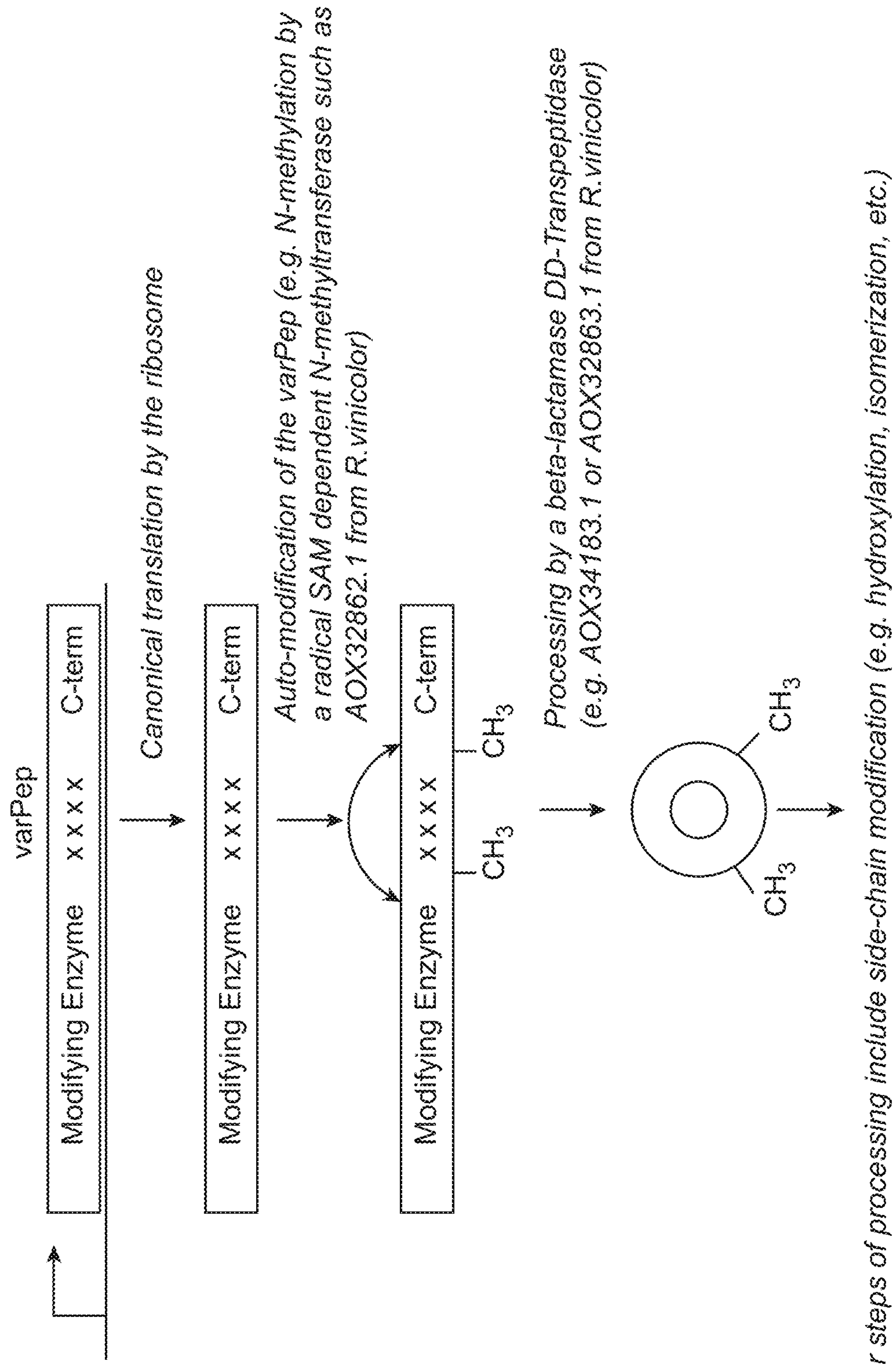
FIG. 12 illustrates a cyclization process of different families of RiPP scaffolds that lead to the generation of N-to-C cyclized, backbone N-methylated macrocycles by the action of a beta-lactamase (alanyl-alanine transpeptidase) and an N-methyltransferase. The variable peptide library region is embedded within the primary sequence of the modifying enzyme. N- and C-term sequences refer to consensus binding and processing recognition elements. The N-terminus comprises the enzymatic N-methyltransferase domain, a linker region, and the processing enzymes binding sites.

In other embodiments, the cyclization comprises reacting with beta-lactamase (FIG. 12). As shown in FIG. 12, a variable region is excised and end-to-end cyclized by the actions of an N-methyltransferase and a beta-lactamase family member. Table 4 shows an exemplary list of lactamase and amino acid sequences of the processed cyclic peptides. In some embodiments, some of the sidechains of the randomized residues are subsequently isomerized from the L- to D-configuration or decorated with additional modifications like hydroxylation, halogenation, glycosylation, acylation, phosphorylation, methylation, and acetylation.

TABLE 4

| Amino acid sequences of the N-methyltransferase and beta-lactamase processed cyclic peptides | | |
|---|---|---|
| *Rhizophogun vinicolor* | SEQ ID NO.: 54 GenBank OAX32863.1 hypothetical protein beta-lactamase (transpeptidase) | MAKVFGLVLGFLSQTFTYPSQVWFSPVGANNGQVITPELSNSIQETLDVWN<br>ITGLSVAIIPKSGEPEYHSWGDRTEDGESVTQDTLFHMASVSKAFCVSALG<br>ILMDDFEHGRNVTPLPPALTEFNWHTSIQDLLPGEWQLMDEWASRKANMKD<br>ILSHVSGLPRHDFAFGPYESPKEAVSRLRYLRPAFELREQWSYNNQMFMVA<br>GHIVETYSGKTYTSFVEDRIFTPLGMSSSTESPAKAAKTGKFTQGWTSSGR<br>LLPELFPEDMVMLMAGAGGVISSAVDMSKWVALWLNKGVYDNVTVIPSSVY<br>GNASQSYAVSISTPVDSEHSIQGYGLGWFQNSYLGHNVVYHSGSIPGLSML<br>VSFLPDDDVGFVVFANGGDKAAPVMNISNSIIDAALHLRSGPAPPIMPEKK<br>AVTSPSEDIVNLELPLEEFSGTYTDPGYGTFTFCSPSSSSSYCQQVMTDFT<br>AVDSVHPSAPSPLQLLAAWPRMGSSHIRAVHQSGNKFLLLCTALFPEGYGR<br>DSTPFETAEIGTPGATAEFVVEDGKVVGEGLEGLVDQVTERERTQTTVKDR<br>AEVWFDKV |

TABLE 4-continued

| Amino acid sequences of the N-methyltransferase and beta-lactamase processed cyclic peptides | | |
|---|---|---|
| *Rhizophogun* vinicolor | SEQ ID NO.: 55 GenBank OAX34183.1 hypothetical protein beta-lactamase (transpeptidase) | MIMAKVFGLVLGFLSQTFTYPSQIRLSPVGVNNGQVITPELSNSIQETLDV<br>WNITGLSVAIIPKSGEPEYHSWGDRTEDGESVTQDTLFHMASVSKAFCVSA<br>LGILMDDFEHGRNVTPLPPALTEFNWHTSIQDLLPGEWQLMDEWASRKANV<br>KDILSHVSGLPSHHFAFGPYESPKEVVSRLRYLRPAFELREQWSYNNQMFT<br>VAGHIVETYSGKTYTSFVEDRIFTPLGMFSSTFSPAKAVKTGKFTQGWTSS<br>GRLLPEFFQEDMIMPMAGPGGVISSAVDMSKWVALWLNKGVHDNVTIIPSS<br>VYGNASQSYAVSISTPVDSEHSILGYGLGWFRNSYLGHDVVYHSGSIPGLS<br>TLVSFLPDDDVGFVVFANGDNKAAPVMNISNRIIDAALHLRSGPAPPIMPE<br>KKAVTSPSEDIVNLELPLEEFSGTYTDPGYGTFTFCSPSSSSPYCQQVIAN<br>FTTVDSVRPSAPSSLQLLAAWPRVGSSHIRTVHQSGNKFMLLPTALFPEGY<br>GRDSTPFETAEIGTRGAPVEFVVEDGRVVGFGLFGLVGQVTERERTQTTVK<br>DRAGVWFDKV |
| *Rhizophogun vinicolor* | SEQ ID NO.: 56 GenBank OAX32862.1 hypothetical N-methyltransferase | MSTKRGTLTIAGSGIASVGHITLGTLSYIKESDKIFYLVCDPVTEAFIYDN<br>STADCFDLSVFYDKTKGRYDSYIQMCEVMLKAVRAGHDVLGVFYGHPGVFV<br>SPSHRAIAVARQEGYKAKMLPGISAEDYMFADLEFDPSVSGCKTCEATEIL<br>LRDKPLDPTIQNIIWQVGSVGVVDMEFSKSKFQLLVDRLEKDFGPDHKVVH<br>YIGAVLPQSTTTMDTFTIADLRKEDVAKQFGTISTLYIPPRDEGHVNLSMA<br>KVFGGPGASVKLNDSIKWAGPKLNIVSANDPHERDVIAQVDTHVAPEGHKK<br>LRVSAAMKKFMTDLALKPKFLEEYKLDPVAVVESAEGLSNLERFGLKFARS<br>GPADALMKATESDIASGRQLTEEEIAQGTGPVGLQTALALLVLLGLGVAIV<br>TRPDD |
| *Rhizophogun vinicolor* | SEQ ID NO.: 57 GenBank OAX34185.1 hypothetical protein FAD/NAD(P)-dependent oxidoreductase, D-amino acid dehydrogenase | MTSDNLQPEVISANWLKSLEAASSTGDTASFVSHFLPDGWFRDMLCFTWNF<br>RTLSGQEKIHGFISEVVDGQSRLSYSHLHDFKLDDHSVNAPSPFKLPGPPD<br>IEGVQGAFTFSITKPAAYGRGFFRLTQDVHGNWKALTLFTNMQDLVGHEES<br>SADEYDPHEKANPTVVIVIKVGGGQSGLICAARLGKLGIRALVIDKNARVG<br>DIWRQRYAEALPSFAVLSRQETQVPEPYAAYSQISKLLPYPSNFPKYLPKG<br>KLANFLESYAINQELCIWLSSTVSPSPVYDSFSARWTVEVEHENRKVILHP<br>KHLVLATGHGRPRIPTWNGMDDFQGTLYHSDFHRDAEKFRGKCVVVIGAGN<br>ASGDICEDFVAQGAAEVTIVQRSATCVVSSATADAFVFKLPFSDKTPIEEL<br>DFRHNSMPLAFVLQLMKSGGTQHMKAHDKEHHEGLRKAGFNLTWEPSPGSG<br>EVGLLGFVFERAGSGTMIDTGFGKLIVEGTVKVKQGQNISHFDKEGITFKD<br>GSKLPADVIVAATGNELTMDAIRAVLGDTIAEQLPPKVWGLDAEGELNQMY<br>RPSGHPGLWFAVGSLGMTRFCSKHLGLQILAQEVGIA |

Figure 15:
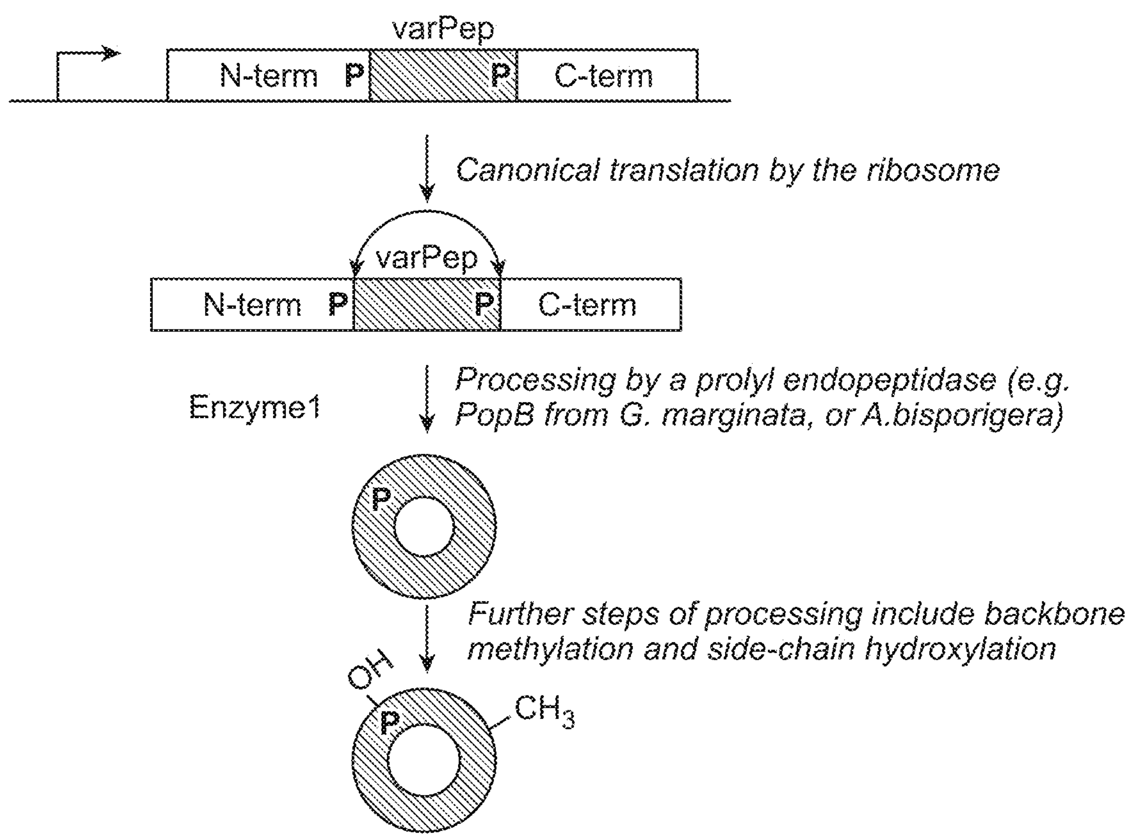
FIG. 15 illustrates a cyclization process for members of the MSDIN family of RiPPs that leads to the generation of N-to-C cyclized macrocycles by the action of prolyl oligopeptidases belonging to the PopB family.
Figure 16:
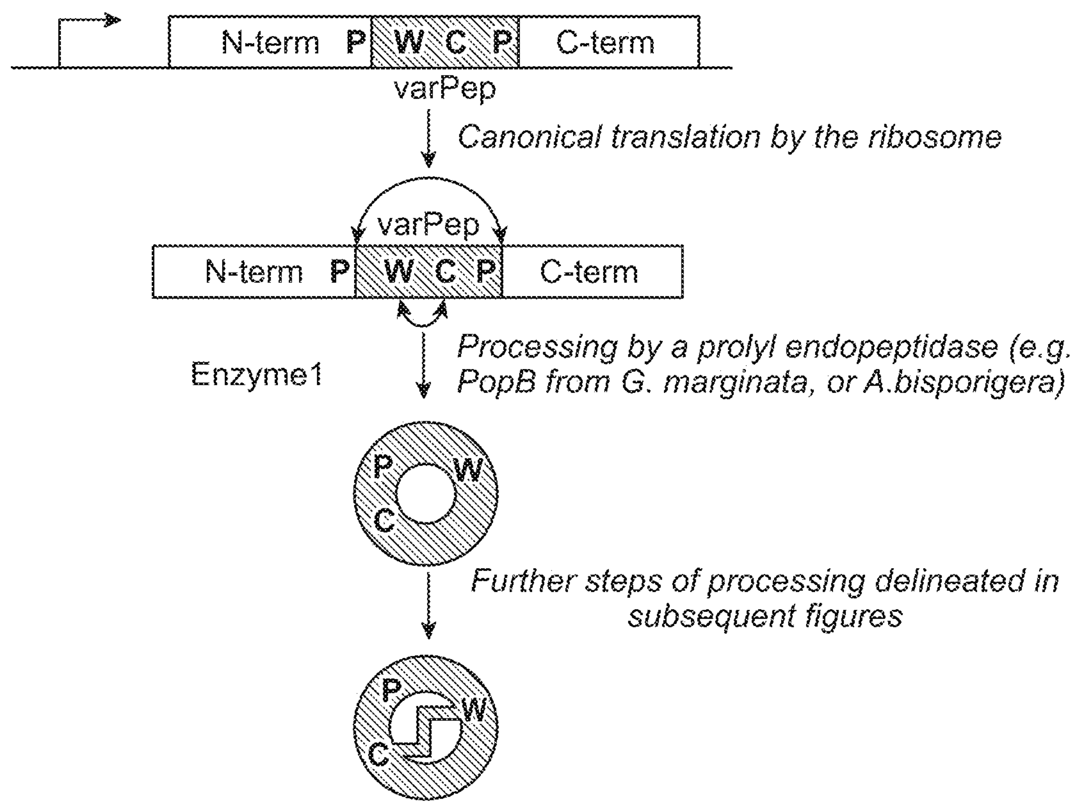
FIG. 16 illustrates a bicyclization process for members of the MSDIN family of RiPPs that leads to the generation of N-to-C cyclized macrocycles and bicyclic macrocycles internally bridged via a tryptathionine bridge.
Figure 17:
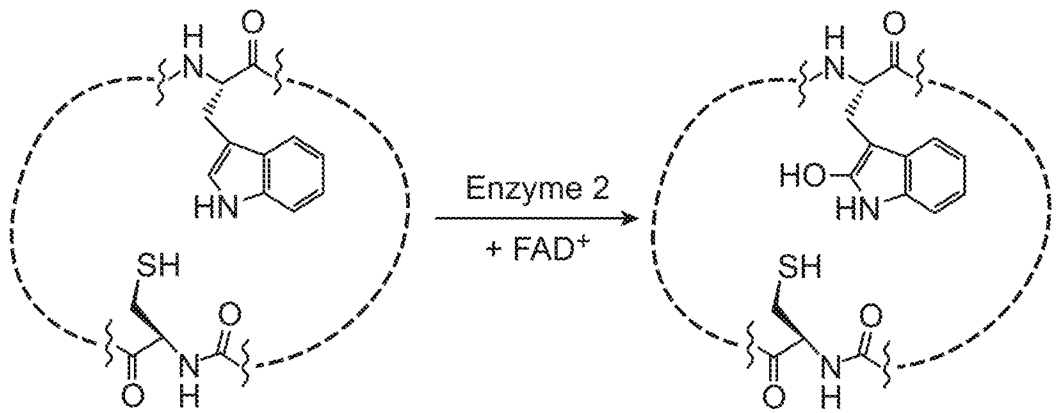
FIG. 17 illustrates biochemical steps to create a tryptathionine bridge of a bicyclic ring.
Figure 17:
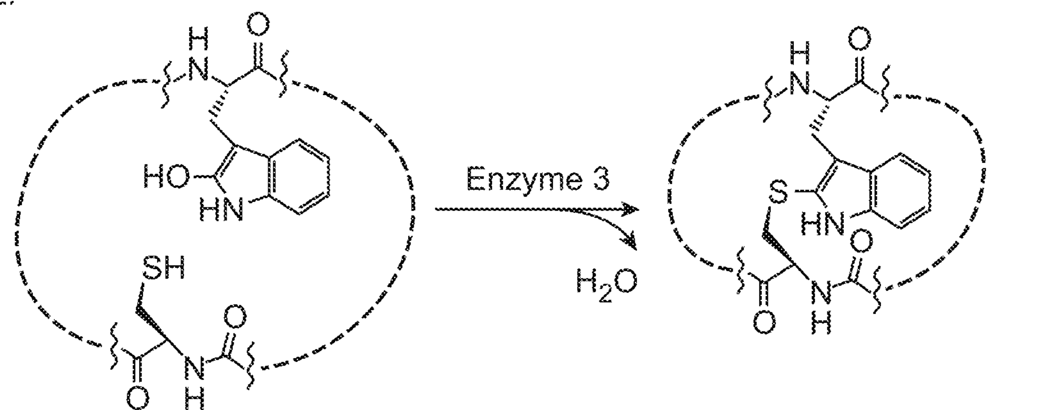
Figure 17:
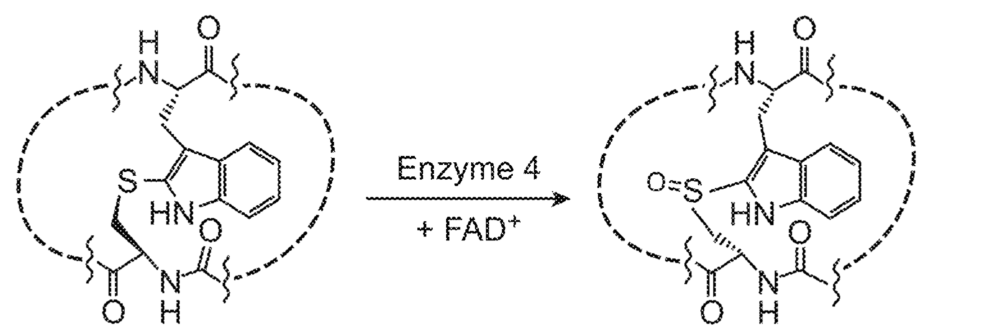
Figure 17:
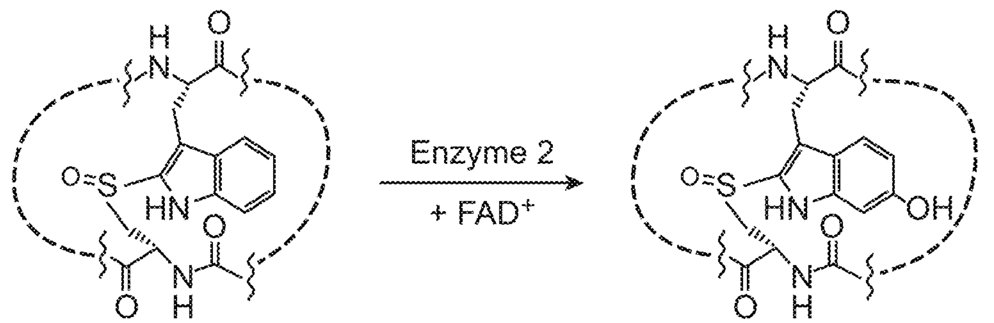

In some embodiments, the cyclization comprises reacting with a prolyl endopeptidase, an N-methyltransferase, and a hydroxylase (FIG. 15). In some embodiments, the bicyclization comprises further modification of the indicated anchored residues on the cyclized peptide, forming an internal tryptathionine bridge (FIG. 16). FIG. 17 illustrates a biochemical steps to create the tryptathionine bridge with hydroxylase and dehydratase. Step 1 involves hydroxylation of the 2-position of the indole ring of the tryptophan residue by a hydroxylase belonging to the cytochrome P450 family of oxygenases (FIG. 17). An example of such hydroxylase is shown in TABLE 5.

TABLE 5

| Amino acid sequences of a hydroxylase | | |
|---|---|---|
| *Galerina marginata* CBS 339.88 | SEQ ID NO.: 58 KDR84981.1 hypothetical protein GALMADRAFT_260690 | MGKMAYHTVLDDIALYLLGSAALVIFYRSFFYPYFLSGRRLAPGPTKGELS<br>KELKQFNNEINVHFLRHMVKEYGPIFRLVGAPMIPGPGLVVCTPTAQQRIL<br>VSNSINYGQPRLAFFRWVTGGLFTLPEREHRGMRKILDPVFSFRNLISTTG<br>VYYNTVQSLITIFRSKIDGENGAKDGDVILVYEWLARLAIDNVSEAILGFK<br>LDTLHDPNNELITTLDELSRIPTAAFELLVRVPGFLRLVTFDSVRHSTLWQ<br>RRVPGRLGVFFTFMRCLSTIRKNALAIKATILQEDSANRDLNVISVLQHMQ<br>SSDETANADIAGNIIMLWMSGRATIATRISWLLWLLAKDQQCQQQLRDEIA<br>PLFSRDPRPDYRSLDKLQWLDSVIMESIRLFLFGPNIRVALNDDYIDGVFV<br>PKGTVVVIPLDLFTRGDIWGEDPDQFKPARWLDSTKRYKISPPFLSFLTGP<br>HRCIAKGMAIMQTKIVIASLIANFEFKPAYEGQHVEGNPSIIGHGMPLHVK<br>PIRPS |

Step 2 involves the formation of a tryptathionine bridge between the 2'-hydroxyl position on tryptophan and the thiol group from the cysteine residue. This condensation reaction is catalyzed by a novel family of dehydratases. Examples of the dehydratases are shown in TABLE 6.

TABLE 6

| Amino acid sequences of dehydratases | | |
|---|---|---|
| Galerina *marginata* CBS 339.88 | SEQ ID NO.: 59 KDR80488.1 hypothetical protein GALMADRAFT_136963 | MPYVPDPKYFEHREQSSGATLYY**C**LV**C**RDGRERQPHHIKT**H**EASQA**H**RTAL<br>SVFDSQAESSSQQTHGNPTQPGYFDPVIDDAVRALLVSGSGDPHQPLYPAG<br>HPNVYGEPNFTDSRRRTSPVTGIDWDQFEAQEDTHAVPSAQDQLRADICQA<br>TLDWLNDDISDDDEREPSEVDSVDSDAESDREPIPDDQPRKRARTNRDNPI<br>SEDWYPWQDKITCTLDILMHLPRSVFSRKQLDLFLWLLRVNNVDDVPTGKS<br>MKMLNKILQGMCGIETIAYEGKLGHNYHVNNIAQILAQELCNPKVGPHIYF<br>YPEDSGDNLAEARQAARWLHELRPEETTPMIHLPSGDYYIYEPAMLSNRSF<br>CIPFRWFTRNGKFHARAWSLETGVVDNTLGWIVHKENEVEISEDDLLKDFT<br>RFSSDCEAYNVPHPSRILGVSCADSGNLLPWNHTNPVLGNRWRQLAKGHRT<br>LCLPLWMYCDDTSGNTSKKWNEHNSFLFTLAGLPREHTAKEYNIHFLCTSN<br>LAPPLEMMDGVVSQIEAAQQNGIWAWDCVRKEPVLIFPTILALLGDNPMHS<br>EFACHIGLRGKFFCRTCWVKGSDAQDDANIVTPGLHETPENSPAPSPAPSP<br>APSPAPSPAPSPALSMAPQSQPPTPSEPSMQVPAPPSTAAPTKARGKKKET<br>MSAMLNRITAFIKPGRLRNKSETQKTLQNFKEQAQTIGAKTKLKTARTETG<br>IKDTVQEFFFEKLFSSYKNKRGPQAKQEALDQAVNQLPSDITSPVWRLKGL<br>DPHQDTPVEILHVVLLGFIKYFWRDLVQNQINDDQKQTLIQRLNSFDVTGL<br>GITQLGGETLVNYAGSLTGRDFRAVAQVAPFVIYDMVPADVFDAWLALSKL<br>VPLVWQPYIENVAQYLTTLEHEIHVFLLRTARWTTGWFNKSKFHIILHLPS<br>HIRRFGPAILFATEAFESFNAVIRAKSVHSNRQAPSRDIALAFAQGNRIRH<br>LLSGGHFLSADTHMVVDPDQPQLGQYERLARGRWRSVGPGPGHLVSAEPIL<br>PSYLGIPPQSTTSSAGLCKRTKTPPQTFLQTLTGLKLPNVSRPGARELWQT<br>CSEVYLLNDDKCLIGHHVIVQRQSEQASFVSPPFIARIGEILQKVGSANHA<br>HDKPDGILVQTLKSSEVADKFQMPRLVPQNEWSFVPLADILCTVNAQHDCD<br>RNGCTASGFRYVYQERIQTNDQRPVVEHVNQPEDFILNTAQMRDALHLQKF<br>RIRSRSLDEQTIIHESVARTINQRKAQDNSSSGTGGAGVSGRGRGRGRGRG<br>GGVEGPSTSRGRGGGIEGRGASSSSGNGRGRGRGARSAQSVPF |
| *Galerina marginata* CBS 339.88 | SEQ ID NO.: 60 KDR74877.1 hypothetical protein GALMADRAFT_99137 | MPRKKPAPECFETDEASKMIR**C**LI**C**KENDTVQQGTWIK**H**GSASQ**H**IETNAH<br>KLAVARREQLLQVQQEEERRLQEIYGGNTIPLSGNAQLYPTYPRANMYGNQ<br>DAVDTDMDNQNSPPQAYMLCDADIPDLGIKPIERPDPSQERERLRQQVEQL<br>LLQAEHEDEFGSPDDPDDLTSTNIAQAFADLDLEEMLDEEEVEDYFNQVSP<br>EHDYYPYPNKTTMLLDILDNLPRLRMSSNQLRLILWLLKQTGVSNVPSFSG<br>FRNMQTHLRNMCGTTPKQHVSSLGNIFYSNNIGESVMRDFANPEVAKHLHL<br>YPEETEGPISEVWQAERWKEFAPSELTPMFSQGHRQFFIDEVAQLQDGQYV<br>IPRNWVMRKGKLTSDCHIVTVNPVRFSKLHGSLVLVLKQCFQSGWTLLSET<br>QIFHADDFQFNYFDVVSRIRGPISWSEGTEVPAMPNNLRELAGDDDLVVIM<br>VPLWCDDVSGNKSKQYNKHINVYMANSNIPGRLLQQEYFVRFVSTSPNATS<br>PEQFSALKDQINETQKKPIQCYNAHTNKKTRAILRVPGLPADNPQQSEESC<br>HMGGNANCKCRKCHVGGPHEKKESNEGYHEHYLTGIKRSAEETRLELEKQI<br>KLAMYGVEKPINETQTNTGTKDKVAQHWIDILLAKSRELKSANPSRSVEEI<br>AQELQTWFDEQPGDKINPLLSIAGLDPTQDTPVEILHTILLGIVKYAWHHL<br>HSNWTEAEQNLFTVRLQSTDIDGLSVPPIRVAYMMQYRNGLIGKHFKTLMQ<br>TLPFHVHGTVSDAQFKLVKAIGELGSVLWVHEIGDMEKYLSDLEILIGNVL<br>DAFAEIDPSTAMYARFIYEPMPVPSKIIVKLKLHMLPHLIEDIKRFGPAIR<br>NSTEVFECFNAIFRLCSILSNHQAASRDIALKFASMDRLKHMLSGGYWLSE<br>VEEGKFEWIRAGENVRNILQSEPTIQRHLGWAPSAKFQSGRKRTPPTSWEN<br>TKASQFMDSEETAAIGFPNPRLLSWRKGVTTTAQSGDRCSTGSWVVARNHK<br>VCYILASHYCSIAKNDQGESCIGRIHEIIGPDEKSASSTGIITLECFQLGK<br>EHHPDFGLPTLQRPQADLPKYILKAWQDPLFIFSAHHDCHTASCQATALQP<br>QLQERQLTSRMNKLIAHNDSDHFIINLYGLHNAILLREFLPRELTAPQPLH<br>QDRKAFHYEVAAKLRVQQAEKRAKTNARRKATRAANKAKQVERQKQNPDHE<br>QESEQEMDERPNSENGSDIELGGDDDIEVETRRKRRRN |
| *Hypsizygus marmoreus* | SEQ ID NO.: 61 KYQ37095.1 hypothetical protein Hypma_08924 | MGRRAEELPAYVELSEDGTLVR**C**NL**C**LMHNRLDYSKEWIQRKGWRS**H**KGSG<br>I**H**DRSEAKQRVLDDAAMDLQEPASAEVEVVTFNDILIINAPKTPTGNMQSE<br>EQAMWDHFDAGSFTLEAGEDPNHSSQRLYQDLARKADAYGAWDGTEALPEY<br>RDLDDVSQFLDEDEEEDLLSEILRGLGLEEEHEDSSDRNPAEELNSPWYPY<br>GSKLMFLLDTIDNLPRLRISGAMMRVFLWLLREVGVRQVPSFDKLRKIQRK<br>LREGSGVPTVHWMSPKGNAYSFNDPAVIVANDWASPITRPHLRRYPVIPKD<br>GVITEVYHAEKWHREINRHFLTPMYDDGFRHYFIDELAQLKDGRYAVPVRW<br>LEDVDGRIVADAWRVELEDDNRATIIDTATVRIHSQELALNFEEIIESNLM<br>PEWSDTTTEAGHPSRMPNPDRALAEGDPIYTSFIDIFGDDVSGNRSKSWNK<br>HWNMYISHRNLPRKLLHQQYHTHFVSTSTFASIPEQFVGVKEAIESTHSKP<br>VKVRDADTGKQIRLKIYCNCGPGDNPSQSETSGHIGGNGNYPCRKCHTGGT<br>QKSKETDEGFYKMFTAGEARSSKETLAEVKSQVEAACTGVAKTVADAQSDT<br>GVKDAYTQYWIDAIIEKARAMQKENPGMPTTTIQATLIKWVYDHEEAIYNS<br>FLTLDGFDASRDTPVEILHTILLGIVKYLWHRSHTSWNAAQKKIYSTRLQG<br>TNTQGLSIHHIRANYIMQYANSLIGRQLKTLAQVNVFHVYDLVDPLRFLFT<br>KATGELCALLWFTEIRDLEEYLSDVDIAAANVLDIAAVIDPSKIVSKIKYH<br>LLSHLREDIIRFGPLVGVATEVFECFNAVERYCSILSNHLAPSRDIAYKLA<br>AQETMKHFLSGGWWHVKDSVDLQGNPKWVQPGPSVRTFMASNPVLHTLCGW<br>TRNNDSTPGTVKSEPRKRGPDKQTLLPLVRLAWLETQGSRALNNTSPNNET<br>QWQRCKYVIAETQDQCNVGSWVFARSPLLENIPIPGRIVEILQDTSASPSA |

TABLE 6-continued

| Amino acid sequences of dehydratases | | |
|---|---|---|
| | | FVVIDVFQVSATRDEVEGMPVLLRRFNECCLHVIPASSVIFDFNAQHDCRY<br>AKCEATGEQPLIQERVPSGVTENFVVHKAIDRYLINIHALHNAHLIRATLP<br>RDLTAPIPYAPNREAHHSAIAAELRSAQDTKRAKTAAKTAANAAAKKAEAA<br>LKDTTSGPAAKRRRVDDEGSGEEDNRDVDMVSV |
| *Galerina marginata* CBS 339.88 | SEQ ID NO.: 62<br>KDR73903.1<br>hypothetical protein<br>GALMADRAFT_141673 | MAKGRKLNNPLPDFIEISNDGLQVR**C**TL**C**LAARQHNGSGWIKRGSVSN**H**LK<br>SDN**H**TNSLEAHEMKKSAEKAEGRSVQEEIAMEEGMDFVILSSKIQPEITAP<br>ARAPRRSNEEQEMWDRYTLGGEVFDAGVDHTLVEAEERKRLEREATDFDLW<br>HGADFLPEEDPNDGELLLDELEQDDILSELLRNAHLNAPDAADVLTEEPRA<br>AADPRICDAWSPYESKMMFLLDTLDNLPRLRISNSLMNVFLWILREGGARD<br>VPSLYHLRQVQTTLRKSTGVPTTQHKSPKGNVYSMNDPRTLVAMDWANPVI<br>CDHIRRYPVIPRNGVISEVYHAQKWRKDVDPHTLSPMYDAGNCHYYIDEVA<br>RLKNGTFIIPVRWLEDEDRNVCADAYVVQFDDQFIASVVDGETIIVQASDL<br>QNNFLDLKDMGLLPTWGNQTIESGHPARMPNPDRALAEGDPLYTSWIDVFG<br>DDVSGNRSKNWNKHWNIYISHRNLPRKLLQQEFHTHFVSTSPVASVTEQFH<br>GIKQVIELTHKSPVKVRHGTSGAQIRFKINVNCGPGDNPAQSEVCGHIGVN<br>GNKLCRKCHTGGTHEVKESDEGFNSLFEPGDARSAQEIVADVESQVQLACL<br>GIAQHVQNQQTKNGIKDAYTQYWIDYLINRARTLRKEQPRRTTADIQSELL<br>VWVQEHKDEIYNPFLKLDGFDAAVDTPVEILHTILLGIVKYLWHGSHTSWT<br>AIQKQTYSVRLQSTDTSGLSIHAIRANYIMQYANSLIGRQFKTIAQVNVFH<br>VYDLVDTTQFLLTKAVGELTALLWIPEIANMEEYLLDVEAAAANVLDLFAL<br>IDPSKMTNKLKLHLLVHLKADILRFGPLVGVATETFECFNAIFRFCSIYSN<br>HLAPSRDIAFQLASQEVLKYRLTGGWWPASDGEWKRPGPSVRNFIHDHPTL<br>QALLGWTKEEKLVNGSFRLEPLKRDASQKIESRKHLPWLQTQGAKAVNSSE<br>DNDSKWTACRFAVANSGDKCSVGSWVFATSPFNSNQSVTGRIVEVLAESEG<br>KRAVVVLDIFEVCSTRHKIFGMPMLARRHEEPVYAVIASTNIEFLYNVQHD<br>CPLAKCTASGKQPLIQERVESGLFKTYIEHKPIEREVINTHAFHNAHRLRA<br>VLQRSLVVPIPLYPPEIRKTKHAEFAHNLQATQKVKLEARAAQKAKEIITP<br>ADKTDSTIPKKRTRSEMETETDDTAIATQADVFFNAQGCP |

Step 3 describes S-oxygenation of the tryptathionine thiol by a flavin-monoxygenase enzyme that converts it to a sulfinyl form. Examples of such monoxygenase are shown in TABLE 7. Step 4 describes potential future modification steps such as hydroxylation of side chains on the peptide such as the hydroxylation of position 6 on the indole ring of the tryptathionine-forming tryptophan residue by a P450 family monoxygenase.

TABLE 7

| Amino acid sequences of monoxygenases | | |
|---|---|---|
| *Galerina marginata* CBS 339.88 | SEQ ID NO.: 63<br>KDR68385.1<br>hypothetical protein<br>GALMADRAFT_104945 | MVQIKRLLLGFLSSPSQTPLESNHGPVPSKSIAVVGAGSAGLAMLRTLVEL<br>EAFSRNNWEVVLYEERESVGGIWLPDNNDVFPPEIPKTPLYPLLRTNTPVP<br>SMTYPGFPFPPSTPLYPRHDHVEAYHLRYARRHNLLDFIKFDTMVEKAFWN<br>GTPEEGYWNLTLSSKEGRMRYKTEDHLVVATGNNHIPHIPVWKGQEDWLAS<br>PANHSRKIIHSVYYRGPEAFSNQTVLIVGNGGSGRDAATQILGYASQTFMS<br>IRRSYGPVDDGVIVKPDISHFTEAGVVEVDGTILDPDVILLGTGYEMQKPL<br>LSEGGELSFDPTAKDNSSVRGILVTNGHYIFPLHRHIFSLSPRYPPNALAF<br>IGLLSFIASCPSDIAQSLFAAHAILDPSILPPRHLLLEELASYEDKARRQG<br>LDPYLKGPIMLNNTSNDYQDELVEYLKQKNAIPDDGKKFVEEWRREILAYH<br>YLQRGWSRIEKLGMGPAWTEGVKTEAQWFDLMTRVNEWQKNWETENGIAFR<br>VDLDLTG |

Figure 13:
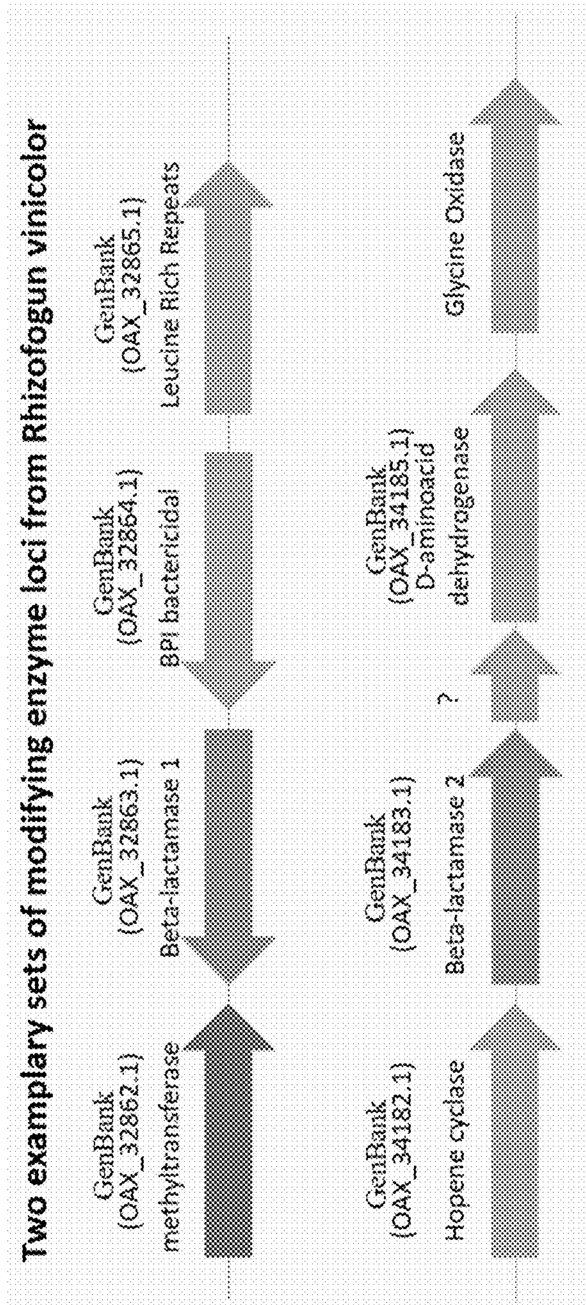
FIG. 13 shows a gene organization within two sets exemplary loci from *Rhizopogon vinicolor* that encode for modifying enzymes that could be used in the schematic depicted in FIG. 12.

A gene organization within two exemplary loci in *Rhizopogon vinicolor* that encode for methyltransferase, beta-lactamase, hopene cyclase, beta-lactamase 2, dehydrogenase, and glycine oxidase is shown in FIG. 13.

Figure 14:
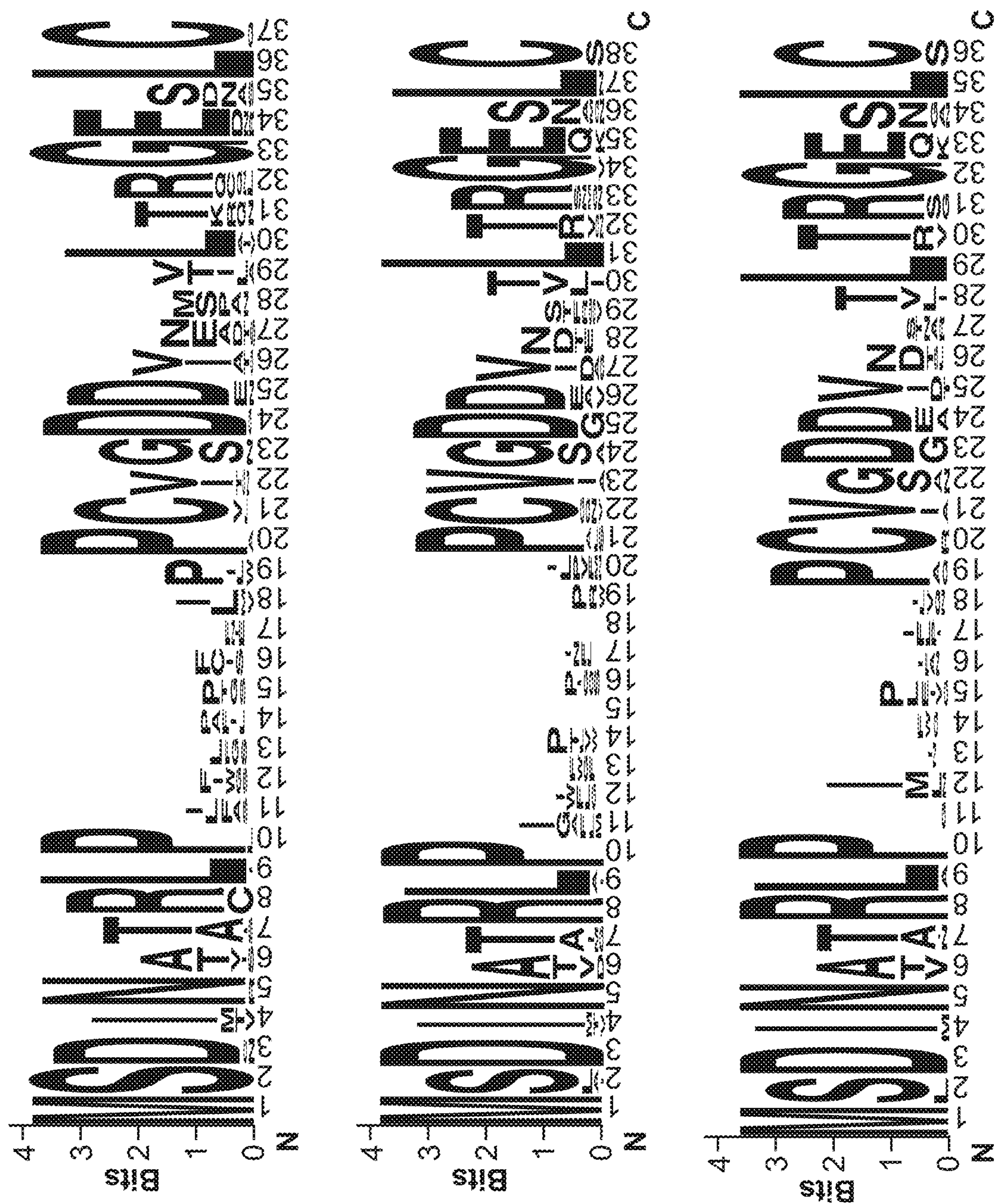
FIG. 14 shows WebLogo alignments of a large variety of MSDIN family genes (toxin preproprotein sequences) identified in the genomes of *Amanita bisporigera* and *Amanita phalloides*. See Pulman, Jane A., et al. "Expansion and Diversification of the MSDIN Family of Cyclic Peptide Genes in the Poisonous Agarics *Amanita Phalloides* and A. *Bisporigera." BMC Genomics*, vol. 17, no. 1, 15 Dec. 2016, p. 1038., doi: 10.1186/s12864-016-3378-7.

The sequence which flanks the encoded random peptide library can be, for example, as shown in FIG. 14, by using N-term and C-term flanks from the MSDIN family genes (toxin preproprotein sequences) identified in the genomes of *Amanita bisporigera* and *Amanita phalloides*. The low consensus central regions indicate areas where a random peptide library could be inserted to facilitate post-translational processing into a cyclic peptide. See Pulman, Jane A., et al. "Expansion and Diversification of the MSDIN Family of Cyclic Peptide Genes in the Poisonous Agarics *Amanita Phalloides* and A. *Bisporigera." BMC Genomics*, vol. 17, no. 1, 15 Dec. 2016, p. 1038., doi: 10.1186/s12864-016-3378-7.

The enzymes can additionally be targeted to a specific cellular compartment to increase peptide synthesis efficiency and increase yield for peptide production purposes.

Disclosed herein, in certain embodiments, is a method of detecting interaction between a first test protein and a second test protein in a host cell, comprising: expressing in the host cell a first fusion protein comprising the first test protein and a second fusion protein comprising the second test protein; delivering a first molecule to the host cell; modifying the first molecule while in the host cell via a modifying enzyme; and allowing the first molecule to modulate the interaction between the first test protein and the second test protein, wherein the first molecule is a product of an encoded DNA sequence, wherein the first molecule comprises a randomized polypeptide library and one or more modifying enzymes, wherein the one or more modifying enzymes modify the randomized polypeptide library.

Host Cells

In some embodiments, the host cell is a eukaryote or a prokaryote. In some embodiments, the host cell is from animal, plant, a fungus, or bacteria. In some embodiments, the fungus is *Aspergillus, S. cerevisiae*, or *Pichia pastoris*. In some embodiments, the host cell is a haploid yeast cell. In other embodiments, the host cell is a diploid yeast cell. In some embodiments, the diploid yeast cell is produced by mating a first host cell comprising DNA sequences encoding the first chimeric gene, the second chimeric gene, and the third chimeric gene, to a second host cell comprising DNA sequences encoding the death agent, positive selection reporter, and the mRNA comprising a nucleotide sequence encoding a polypeptide. In some embodiments, the plant is *Nicotiana tabacum* or *Physcomitrella patens*. In some embodiments, the host cell is a sf9 (*Spodoptera frugiperda*) insect cell.

Disclosed herein, in certain embodiments, is a host cell configured to express a first fusion protein comprising a DNA-binding moiety; a second fusion protein comprising a gene activating moiety; a third fusion protein comprising a different DNA-binding moiety; a death agent, wherein the expression of the death agent is under control of a promoter DNA sequence specific for one of the DNA-binding moiety; a positive selection reporter, wherein the expression of the positive reporter is under control of a promoter DNA sequence specific for the other DNA-binding moiety; and a polypeptide of 60 or fewer amino acids, wherein the polypeptide modulates an interaction between the first test protein and the second test protein; wherein the host cell optionally has a mutant background enabling uptake of small molecules; and wherein the host cell optionally has a mutant background enabling increased transformation efficiency.

Disclosed herein, in certain embodiments, is a host cell comprising a plasmid vector which comprises the components of PLASMID 1, or any combination of the components of PLASMID 1; or the plasmid vector, wherein a DNA sequence encoding a first polypeptide is inserted in frame with Gal4-DBD, a second polypeptide is inserted in frame with LexA-DBD, and wherein a DNA sequence encoding a third polypeptide is inserted in frame with VP64-AD.

Disclosed herein, in certain embodiments, is a kit comprising PLASMID 1, PLASMID 2, and PLASMID 3; and transfectable host cells compatible with PLASMIDS 1-3, or any combination thereof. In some embodiments, the provided host cells are already transfected with PLASMID 1 or 2. In some embodiments, the kit includes selectable agents for use with host cells transfected with PLASMIDS 1-3. In some embodiments a library of variants of PLASMID 1 are provided, wherein more than a single pair of Y2H interactors are represented. Such a library can be used to, for example, screen for protein-protein interactions that are inhibited by a defined agent. In some embodiments a library of variants of PLASMID 2 are provided, wherein a plurality of different short test polypeptide sequences for screening are represented. The plurality of different short peptide sequences can be randomly generated by any method (e.g. NNK or NNN nucleotide randomization). The plurality of different short peptide sequences can also be preselected, either by previous experiments selecting for binding to a target, or from existing data sets in the scientific literature that have reported rationally-designed peptide libraries.

The host cell can additionally be made to be permeable to small molecules, for example by deletion of drug efflux pumps, such as PDR5, ERG6, or 12geneΔ0HSR (*Chinen,* 2011), to enable a small molecule screening approach.

The host cell can additionally carry mutations to enable more efficient transformation with vectors and/or more efficient uptake small molecules.

PLASMIDS 1, 2, and 3 can be used in various permutations. In some embodiments, integration of PLASMID 1 into the genome of the host cell (as confirmed using PLASMID 3) is followed by transformation of a library of PLASMID 2 with randomly encoded peptides using, for example, NNK or NNN codons.

In some embodiments, to perform a screen to identify a peptide that can disrupt a PPI, the host cell is propagated in selection media to ensure the presence of PLASMID 1 and a proper PPI (e.g. on media lacking the positive selection marker for yeast, or in media containing antibiotic for human or bacterial cells). This host cell is then be transformed with PLASMID 2, and immediately transferred to selection media to ensure all components are present (i.e. on media lacking both plasmid selection markers for yeast, or antibiotics for bacterial or mammalian cells), and are inducing expression of any inducible component (e.g. with Gal, doxycycline, etc).

In other embodiments, the plasmids are used as a 'plug and play platform' utilizing the yeast mating type system, where the 2 or more plasmids (or the genetic elements therein) are introduced into the same cell by cell fusion or cell fusion followed by meiosis instead of transfection. This cell fusion involves two different yeast host cells bearing different genetic elements. In this embodiment, yeast host cell 1 is one of MATa or MATalpha and includes an integration of PLASMID 1. In this embodiment, yeast host cell 1 strain can be propagated on positive selection media to ensure a proper PPI is present. In this embodiment, the yeast host cell 2 can be the opposite mating type. This strain carries (or has integrated) the randomized peptide library and 'death agent' (e.g. cytotoxic reporter) plasmid (PLASMID 2). Yeast host cell 2 can be generated via large batch high efficiency transformation protocols which ensure a highly diversified library variation within the cell culture. Aliquots of this library batch can then be frozen to maintain consistency. In this embodiment, the strains are mated in batch to result in a diploid strain that carries all the markers, the PPI, positive selection, 'death agents' and peptide. This batch culture then can be propagated on solid medium that enables selection of all the system components (i.e. media lacking both positive selection markers), and inducing expression of any inducible component (i.e. with Gal).

Surviving colonies from limiting dilution experiments performed on host cells bearing both the Y2/3H and library/cytotoxic constructs (either introduced to the cell by transfection or mating) can constitute colonies with a specific PPI that has been disrupted by a peptide and no longer triggers the death cascade triggered by the encoded 'death agents' (e.g. cytotoxic reporters) while maintaining a differential PPI driving a positive selection marker. The peptide sequence can be obtained by DNA sequencing the peptide-encoding region of PLASMID 2 in each surviving colony.

To ensure that survival is due to inhibition of the PPI rather than stochastic chance or faulty gene expression, an inducible promoter can be used to inactivate the production of either the PPI or the peptide and confirm specificity. In some embodiments, cell survival is observed only on media with galactose wherein all the components are expressed; and no survival is observed on media without galactose when expression of the peptide is lost.

The plasmids can also be isolated and re-transformed into a fresh host cell to confirm specificity. Biochemical fractionation of the viable host cells which contain the PPI, peptide, positive selection and 'death agent' followed by pull-down experiments can confirm an interaction between the peptide sequence and either PPI partner using the encoded tags (e.g. Myc-tag, HA-tag, His-tag). This is also helpful to perform SAR to determine the binding interface.

The peptides to be used in screening assay can be derived from a complex library that involves post-translational modifying enzymes. The modified peptides can be analyzed by methods such as mass spectrometry, in addition being sequenced to ID the primary sequence. The peptides can also be tested for inherent membrane permeability by reapplying them onto the host cells exogenously (from a lysate) and observing for reporter inactivation or activation.

Once enough surviving host cell colonies are sequenced, highly conserved sequence patterns can emerge and can be readily identified using a multiple-sequence alignment. Any such pattern can be used to 'anchor' residues within the library peptide insert sequence and permute the variable residues to generate diversity and achieve tighter binding. In some embodiments, this can also be done using an algorithm developed for pattern recognition and library design. Upon convergence, the disrupting peptide pattern, as identified through sequencing, can be used to define a peptide disruptor sequence. Convergence is defined by the lack of retrieval of any new sequences in the last iteration relative to the penultimate one.

EXAMPLES

Example 1: Method for Identifying a Disruptor of a Protein-Protein Interaction This is an example of a system that uses two variants of one protein, fused to different DBDs to identify inhibitors against a specific PPI. The PPI integration plasmid (PLASMID 1; FIG. 8) is used to integrate into *Saccharomyces cerevisiae* three proteins that constitute the binary PPIs of interest. The plasmid encodes for the fusion of an AD (VP16) with c-Raf, a DBD (LexA) with KRas(G12D), and a DBD (Gal4BD) with KRas, driven by a strong promoter and terminator ADH1. Fusion proteins VP16-c-Raf, LexA-KRas(G12D), and Gal4BD-KRas are tagged with MYC, FLAG, and HA, respectively. The plasmid further includes bacterial selection and propagation markers (ori and AmpR), and yeast replication and selection markers (TRP1 and CEN). The plasmid also has sites for integration into the genome at a specified locus.

*Saccharomyces cerevisiae* is co-transformed with the selection and library plasmid (PLASMID 2; FIG. 9) for the expression of a randomized peptide library (NNK 20-mer sequences). The plasmid is driven by a strong promoter, ADH1. The initiation sequence of the selection and library plasmid is a fixed sequence of methionine-valine-asparagine (MVN) to maximize the half-life of the peptide, and terminated with an untranslated region (UTR) of a short protein (sORF1). The selection and library plasmid also comprises a sequence that encodes a His-tag. The translated protein has the N-terminus of methionine to minimize proteolysis.

The selection and library plasmid additionally comprises a LexAop sequence, which induces 'death agents' (cytotoxic reporter expression) when bound by a functional transcriptional factor that is formed by LexA-KRas(G12D) fusion protein and VP64-c-Raf fusion protein, unless interrupted by a disrupter peptide. The selection and library plasmid also contains a positive selection marker, ADE2 which is under control of Gal4BD-KRas. The plasmid further includes bacterial selection and propagation markers (ori and AmpR), and yeast replication and selection markers (TRP1 and CEN).

To confirm expression of the reporters and the successful construction of the strains, *Saccharomyces cerevisiae* is transformed with a confirmation plasmid (PLASMID 3; FIG. 10). The confirmation plasmid includes a direct fusion between the AD fusion protein (VP64-c-Raf) and DBD fusion proteins (LexA-KRas(G12D) or Gal4BD-KRas). The confirmation plasmid includes yeast replication and selection markers (TRP1 and CEN). The confirmation plasmid is used to confirm integration of LexAop promoter before the ADE2 gene. Transformation with the confirmation plasmid allows for the activation of ADE2 only if the promoter is properly integrated. Also, confirmation of death agents is enabled by inducible expression of the confirmation fusion construct.

The screen is performed by mating the strains in a batch to result in a diploid strain, which carries all the markers, the PPIs, the positive selection, the death agents, and the peptide. This batch culture is then propagated on solid medium, which enables selection of all the system components (media lacking two nutritional components) and induces expression of any inducible component with Gal.

Surviving colonies constitute colonies with a specific PPI(KRas-c-Raf) that have been disrupted by a peptide and no longer trigger the death cascade induced by the encoded death agents and maintain positive selection of the remaining PPI.

The peptide sequence that disrupts the death agent-driving PPI is obtained by DNA sequencing the peptide-encoding region of the selection and library plasmid in each surviving colony.

To confirm specificity, the inducible marker is used to inactivate the production of the PPI and confirm specificity. The plasmid is then isolated and re-transformed into a fresh parental strain to confirm specificity.

Biochemical fractionation of the viable strain that contained the PPI, peptide, selection marker, and death agent, followed by pull-down experiments is done to confirm an interaction between the peptide sequence and either PPI partner using the encoded tags.

An alternative example can be made by switching LexA with TetR. In another alternative example, fusion proteins in the PPI integration plasmid and the randomized peptide library in selection and library plasmid are driven by an inducible promoter, GAL1, instead of ADH1 used alternatively in another example. In yet another example, the N-terminus of the peptide translated from the selection and library plasmid can alternatively be glycine, alanine, serine, threonine, valine, or proline. In other examples, the genetic reporter in the confirmation plasmid is HIS3 or URA3, in place of ADE2. Either mating types of *Saccharomyces cerevisiae* haploid state can be used as background strain in alternative examples. In other examples, background strains also express the enzymes for the cyclization and methylation of peptides like lanthipeptides maturation enzymes from *Lactococcus lactis* (LanB, LanC, LanM, LanP), patellamide biosynthesis factors from cyanobacteria (PatD, PatG), butelase 1 from Clitoria ternatea, and GmPOPB from *Galerina marginata* or other species.

Example 2: Method for Identifying Protein-Protein Interaction Disruptor

This is an example of system that uses two different proteins, fused to different DBDs to identify inhibitors against a specific PPI. The PPI integration plasmid (PLASMID 1; FIG. 8) is used to integrate into *Saccharomyces cerevisiae* three proteins that constitute the binary PPIs of interest. The plasmid encode for the fusion of an AD (VP64) with TEAD, a DBD (LexA) with YAP, and a DBD (Gal4BD) with VGLL4, each associated with ADH1 promoter. Three protein fusion sequences are tagged with either FLAG, MYC or HA. The plasmid further includes yeast replication and selection markers (TRP1 and CEN). The plasmid also has sites for integration into the genome at a specified locus.

The *Saccharomyces cerevisiae* is co-transformed with the selection and library plasmid (PLASMID 2; FIG. 9) for the expression of a randomized peptide library (NNK 20-mer sequences). The selection plasmid is driven by a strong promoter, ADH1. The selection and library plasmid also comprises a sequence that encodes a His-tag.

The selection and library plasmid additionally comprises a LexAop sequence, which induces 'death agent' (cytotoxic reporter expression) when bound by a functional transcriptional factor that is formed by LexA-YAP fusion protein and VP64-TEAD fusion protein, unless interrupted by a disrupter peptide. The selection and library plasmid also contains a positive selection marker, ADE2 which is under control of Gal4BD-VGLL4 and VP64-TEAD. The plasmid further includes yeast replication and selection markers (TRP1 and CEN).

To confirm expression of the reporters and the successful construction of the strains, *Saccharomyces cerevisiae* is transformed with a confirmation plasmid (PLASMID 3; FIG. 10). The confirmation plasmid includes a direct fusion between the AD fusion protein (VP64-TEAD) and DBD fusion proteins (LexA-YAP or Gal4BD-VGLL4). The confirmation plasmid includes yeast replication and selection markers (TRP1 and CEN). The confirmation plasmid is used to confirm integration of LexAop promoter before the ADE2 gene. Transformation with the confirmation plasmid allows for the activation of ADE2 only if the promoter is properly integrated. Also, confirmation of death agents is enabled by inducible expression of the confirmation fusion construct.

The screen is performed by propagating the parental strain on selection media to ensure the presence of the PPI Integration plasmid, and that a proper PPI has occurred, which is confirmed via use of the confirmation plasmid. The strain is cultured on media lacking nutrient markers against positive selection markers to ensure selection of colonies where the desired interaction occurred. The strain is then transformed with the selection and library plasmid, and is immediately plated on selection media to ensure all components are present (on media lacking the two nutritional markers) and is induced expression of any inducible component (with Gal).

Surviving colonies constitute colonies with a specific PPI(YAP-TEAD) that has been disrupted by a peptide and no longer triggers the death cascade induced by the encoded death agents and maintain positive selection of the remaining PPI.

The peptide sequence that disrupts the death agent-driving PPI is obtained by DNA sequencing the peptide-encoding region of the selection and library plasmid in each surviving colony.

To confirm specificity, the inducible marker is used to inactivate the production of the PPI and confirm specificity. The plasmid is then isolated and re-transformed into a fresh parental strain to confirm specificity.

Biochemical fractionation of the viable strain that contained the PPI, peptide, selection marker, and death agent is followed by pull-down experiments to confirm an interaction between the peptide sequence and either PPI partner using the encoded tags.

An alternative example can be made by switching LexA with TetR. In another alternative example, fusion proteins in the PPI integration plasmid and the randomized peptide library in selection and library plasmid are driven by an inducible promoter, GAL1, instead of ADH1 used alternatively in another example. In yet another example, the N-terminus of the peptide translated from the selection and library plasmid can alternatively be glycine, alanine, serine, threonine, valine, or proline. In other examples, the genetic reporter in the confirmation plasmid is HIS3 or URA3, in place of ADE2. Either mating types of *Saccharomyces cerevisiae* haploid state can be used as background strain in alternative examples. In other examples, background strains also express the enzymes for the cyclization and methylation of peptides like lanthipeptides maturation enzymes from *Lactococcus lactis* (LanB, LanC, LanM, LanP), patellamide biosynthesis factors from cyanobacteria (PatD, PatG), butelase 1 from Clitoria ternatea, and GmPOPB from *Galerina marginata* or other species.

Example 3: Method for Identifying Protein-Protein Interaction Facilitator

This is an example of system that uses two variants of one protein, fused to different DBDs to identify facilitator for a specific PPI. The PPI integration plasmid (PLASMID 1; FIG. 8) is used to integrate into *Saccharomyces cerevisiae* three proteins that constitute the binary PPIs of interest. The plasmid encodes for the fusion of an AD (VP64) with Mdm2, a DBDs (LexA) with KRas, and a DBD (Gal4BD) with KRas(G12D). DBD-KRas, each driven by ADH1 promoter. Three protein fusion sequences are tagged with either FLAG, MYC or HA. The plasmid further includes yeast replication and selection markers (TRP1 and CEN). The plasmid also has sites for integration into the genome at a specified locus.

The *Saccharomyces cerevisiae* is co-transformed with the selection and library plasmid (PLASMID 2; FIG. 9) for the expression of a randomized peptide library, NNK 20-mer sequences. The selection plasmid is driven by a strong promoter, ADH1. The selection and library plasmid also comprises a sequence that encodes a HIS tag.

The selection and library plasmid additionally comprises a LexAop sequence, which induces 'death agents' (cytotoxic reporter expression) when bound by a functional transcriptional factor that is formed by LexA-KRas fusion protein and VP64-Mdm2 fusion protein, when mediated by a facilitator peptide. The selection and library plasmid also contains a positive selection marker, ADE2 which is under control of Gal4BD-KRas(G12D) fusion protein and VP64-Mdm2 fusion protein and leading to expression of the positive selection marker when the fusion proteins are mediated by a facilitator. The plasmid further includes yeast replication and selection markers (TRP1 and CEN).

To confirm expression of the reporters and the successful construction of the strains, *Saccharomyces cerevisiae* is transformed with confirmation plasmid (PLASMID 3; FIG. 10). The confirmation plasmid includes a direct fusion between the AD fusion protein (VP64-Mdm2) and DBD fusion proteins (LexA-KRas or Gal4BD-KRas(G12D)). The confirmation plasmid includes yeast replication and selection markers (TRP1 and CEN). The confirmation plasmid is used to confirm integration of LexAop promoter before the ADE2 gene. Transformation with the confirmation plasmid allows for the activation of ADE2 only if the promoter is properly integrated. Also, confirmation of death agents is enabled by inducible expression of the confirmation fusion construct.

The screen is performed by mating the strains in a batch to result in a diploid strain, which carries all the markers, the PPIs, the positive selection, the death agents, and the peptide. This batch culture is then propagated on solid medium, which enable selection of all the system components (media lacking two nutritional components) and induce expression of any inducible component with Gal.

Surviving colonies constitute colonies with a specific PPI(KRas(G12D)-Mdm2) that has been facilitated by a peptide and do not have nonspecific PPI(KRas-Mdm2) that can trigger the death cascade induced by the encoded death agents and maintain positive selection of the remaining PPI.

The peptide sequence that is able to facilitate a specific PPI is obtained by DNA sequencing the peptide-encoding region of the selection and library plasmid in each surviving colony.

To confirm specificity, the inducible marker is used to inactivate the production of the PPI and confirm specificity. The plasmid is then isolated and re-transformed into a fresh parental strain to confirm specificity.

Biochemical fractionation of the viable strain that contained the PPI, peptide, selection marker, and death agent is followed by pull-down experiments to confirm an interaction between the peptide sequence and either PPI partner using the encoded tags.

An alternative example can be made by switching LexA with TetR. In another alternative example, fusion proteins in the PPI integration plasmid and the randomized peptide library in selection and library plasmid are driven by an inducible promoter, GAL1, instead of ADH1 used alternatively in another example. In yet another example, the N-terminus of the peptide translated from the selection and library plasmid can alternatively be glycine, alanine, serine, threonine, valine, or proline. In other examples, the genetic reporter in the confirmation plasmid is HIS3 or URA3, in place of ADE2. Either mating types of *Saccharomyces cerevisiae* haploid state can be used as background strain in alternative examples. In other examples, background strains also express the enzymes for the cyclization and methylation of peptides like lanthipeptides maturation enzymes from *Lactococcus lactis* (LanB, LanC, LanM, LanP), patellamide biosynthesis factors from cyanobacteria (PatD, PatG), butelase 1 from Clitoria ternatea, and GmPOPB from *Galerina marginata* or other species.

Example 4: Reversible Induction of a Nutritional Reporter by Protein-Protein Interaction This is an example of two platforms that either used two variants or two different proteins, fused to different DBDs to identify inhibitor by nutrient based selection. In the first platform, KRas and KRas(G12D) fused to DBDs and c-Raf fused to AD were expressed in *Saccharomyces cerevisiae* cells using an integration plasmid (FIG. 6). In the absence of any inhibitors, the DBD fusion protein and AD fusion protein pairs maintained their interaction to drive expression of Nutritional reporters 1 and 2. A 5-fold dilution series starting at $10^4$ cells were spotted onto selective media with or without inhibitor and visualized after 2 days of growth at 30° C. The results showed that the cells grown on media that selected for Nutritional reporter 2 had poor survival rate when added the inhibitor, illustrating the specificity of the inhibitor for KRas(G12D) and c-Raf interaction.

In the second platform, VGLL4 or YAP fused to DBD and TEAD fused to AD were expressed in *Saccharomyces cerevisiae* cells with an integration plasmid (FIG. 6). In the absence of any inhibitors, the DBD fusion protein and AD fusion protein pairs maintained their interaction to drive expression of Nutritional reporters 1 and 2. A 5-fold dilution series starting at $10^4$ cells were spotted onto selective media with or without inhibitor and visualized after 2 days of growth at 30 C. The results showed that the cells grown on media that selected for Nutritional reporter 2 had particularly poor survival rate when added the inhibitor, illustrating the specificity of the inhibitor for YAP and TEAD.

Example 5: Reversible Induction of a Cytotoxic Reporter by Protein-Protein Interaction This is an example of two platforms that used either two variants or two different proteins, fused to different DBDs to identify inhibitor by toxicity based selection. In the first platform, KRas and KRas(G12D) fused to DBDs and c-Raf fused to AD were expressed in *Saccharomyces cerevisiae* cells with an integration plasmid. In the absence of inhibitors, the KRas(G12D) and c-Raf maintained an interaction to drive expression of cytotoxic reporter. A nutritional reporter was controlled by KRas and c-Raf interaction. The cells were patched onto selective media for a nutritional marker with or without inhibitor and visualized after 4 days of growth at 30° C. In cell populations with KRas(G12D) and c-Raf interaction, only those with the inhibitor showed enhanced cell viability, illustrating the specificity of the inhibitor to KRas(G12D) and c-Raf interaction. In the second platform, VGLL4 or YAP fused to DBD and TEAD fused to AD were expressed in *Saccharomyces cerevisiae* cells with an integration plasmid. In the absence of inhibitors, the YAP and TEAD maintained their interaction to drive expression of cytotoxic reporter. A nutritional reporter was controlled by VGLL4 and TEAD interaction. The cells were patched onto selective media for a nutritional marker with or without inhibitor and visualized after 4 days of growth at 30 C. In cell populations with YAP and TEAD interaction, only those with the inhibitor showed enhanced cell viability, illustrating the specificity of the inhibitor to YAP and TEAD interaction.

Example 6: Cyclization of Peptides

This is an example of a system that induces cyclization of randomized peptides in a complex to achieve enhanced cell permeability and peptide stability. The *Saccharomyces cerevisiae* is transformed with the selection and library plasmid (PLASMID 2; FIG. 9) for the expression of a randomized peptide library, NNK 60-mer sequences. The selection plasmid is driven by a strong promoter, ADH1. The initiation sequence of the selection and library plasmid is a fixed sequence that encodes Methionine Valine Asparagine (MVN) at N-terminus of peptide to maximize the half-life of the peptide, and terminate with sequence that encodes the UTR of a short protein (sORF1). The peptide is also tagged with a HIS tag.

The variable peptide library region of the selection and library plasmid is embedded within primary sequence of modifying enzyme, a homolog of N-methyltransferase from *Rhizophogun vinicolor* and contains randomized residues. The diversified variable region is excised and end-to-end cyclized by the action of a beta-lactamase DD-transpeptidase from *R. vinicolor*. Some of the side chains of the randomized residues are subsequently post-translationally isomerized from L- to D-configuration and hydroxylated.

Example 7: Cyclization of Peptides

This is an example of a system that induces cyclization of randomized peptides in a complex to achieve enhanced cell permeability and peptide stability. The *Saccharomyces cerevisiae* is transformed with the selection and library plasmid (PLASMID 2; FIG. 9) for the expression of a randomized peptide library, NNK 60-mer sequences. The selection plasmid is driven by a strong promoter, ADH1. The initiation sequence of the selection and library plasmid is a fixed sequence that encodes Methionine Valine Asparagine (MVN) at N-terminus of peptide to maximize the half-life of the peptide, and terminate with sequence that encodes the UTR of a short protein (sORF1). The peptide is also tagged with a HIS tag.

The variable peptide library region of the selection and library plasmid is embedded within primary sequence of modifying enzyme, a homolog of prolyl endopeptidases belonging to the PopB family and contains randomized residues. A post-translational processing of the variable peptide by the co-expressed prolyl endopeptidases leads to the generation of N-to-C cyclized macrocycles.

Example 8: Bicyclization of Peptides

This is an example of a system that induces cyclization of randomized peptides in a complex to achieve enhanced cell permeability and peptide stability. The *Saccharomyces cerevisiae* is transformed with the selection and library plasmid (PLASMID 2; FIG. 9) for the expression of a randomized peptide library, NNK 60-mer sequences. The selection plasmid is driven by a strong promoter, ADH1. The initiation sequence of the selection and library plasmid is a fixed sequence that encodes Methionine Valine Asparagine (MVN) at N-terminus of peptide to maximize the half-life of the peptide, and terminated with sequence that encodes the UTR of a short protein (sORF1). The peptide is also tagged with a HIS tag.

The variable peptide library region of the selection and library plasmid is embedded within primary sequence of modifying enzyme, a homolog of prolyl endopeptidases belonging to the PopB family and contains randomized residues. A post-translational processing of the variable peptide by the co-expressed prolyl endopeptidases leads to the generation of N-to-C cyclized macrocycles.

The macrocycles is then hydroxylated at the 2-position of the indole ring of the tryptophan residue by a hydroxylase belonging to the Cytochrome P450 family of oxygenases. A condensation reaction is followed catalyzed by dehydratase to form a tryptathionine bridge between the 2'-hydroxyl position on tryptophan and the thiol group from the cysteine residue. A flavin-monoxygenase enzyme converts the intermediate product to a sulfinyl form by S-oxygenation of the tryptathionine thiol. Some of the side chains of the peptide are subsequently hydroxylated at position 6 on the indole ring of the tryptathionine-forming tryptophan residue by a P450 family monoxygenase. The resulting bicyclized macrocycles comprises a tryptathionine bridge.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A method of screening for a molecule that disrupts an interaction between a first test protein and a second test protein in a host cell, while not disrupting an interaction between a third test protein and a second test protein in the host cell, the method comprising:

expressing in the host cell a first fusion protein comprising the first test protein and a first DNA-binding moiety;

expressing in the host cell a second fusion protein comprising the second test protein and a gene activating moiety;

expressing in the host cell a third fusion protein comprising a third test protein and a second DNA-binding moiety, wherein the second DNA-binding moiety is different from the first DNA-binding moiety; and delivering a molecule to the host cell to test for disruption of the interaction of the first test protein and the second test protein without disrupting the interaction between the third test protein and the second protein;

wherein a plurality of death agent genes are disposed within the host cell, each operably linked to a promoter DNA sequence specific for the first DNA-binding moiety, wherein a positive selection reporter is disposed within the host cell and operably linked to a promoter DNA sequence specific for the second DNA binding moiety, wherein, when the molecule does not disrupt the interaction between the first test protein and the second test protein and does not disrupt the interaction between the second test protein and the third test protein, an interaction between the first test protein and the second test protein causes the gene activating moiety to activate expression of the death agent genes, while an interaction between the second test protein and the third test protein causes the gene activating moiety to activate expression of the positive selection reporter;

wherein, when the molecule disrupts the interaction between the first test protein and the second test protein but not the third test protein and the second test protein, (1) an interaction between the second test protein and the third test protein causes the gene activating moiety to activate expression of the positive selection reporter; and (2) disruption of the interaction between the first test protein and the second test moiety does not activate expression of the death agents, and wherein the host cell is an animal cell.

2. The method of claim 1, wherein the host cell comprises an integrated DNA encoding the first fusion protein, an integrated DNA encoding the second fusion protein, an integrated DNA encoding the third fusion protein, a plasmid DNA encoding death agents produced by the death agent genes, and a plasmid DNA encoding the positive selection reporter.

3. The method of claim 1, wherein the first test protein is a Ras variant, the second test protein is a Raf kinase, and the third test protein is Ras.

4. The method of claim 1, wherein the first DNA-binding moiety, the second DNA-binding moiety, or both, is a LexA, cI, Gli-1, YY1, Glucocorticoid receptor, TetR, or Ume6 DNA binding moiety.

5. The method of claim 1, wherein the gene activating moiety is a VP16, GAL4, NF-κB, B42, BP64, VP64, or p65 gene activating moiety.

6. The method of claim 1, wherein death agent(s) encoded by the death agent genes are selected from the group consisting of: a ribosomally encoded xenobiotic agent, a ribosomally encoded poison, a ribosomally encoded endogenous or exogenous gene that results in severe growth defects upon mild overexpression, a ribosomally encoded recombinase that excises an essential gene for viability, a limiting factor involved in the synthesis of a toxic secondary metabolite, and any combination thereof.

7. The method of claim 1, wherein death agent(s) encoded by the death agent genes are selected from the group consisting of: Cholera toxin, SpvB toxin, CARDS toxin, SpyA Toxin, HopU1, Chelt toxin, Certhrax toxin, EFV toxin, ExoT, CdtB, Diphtheria toxin, ExoU/VipB, HopPtoE, HopPtoF, HopPtoG, VopF, YopJ, AvrPtoB, SdbA, SidG, VpdA, Lpg0969, Lpg1978, YopE, SptP, SopE2, SopB/SigD, SipA, YpkA, YopM, Amatoxin, Phallacidin, Killer toxin KP1, Killer toxin KP6, Killer Toxin K1, Killer Toxin K28 (KHR), Killer Toxin K28 (KHS), Anthrax lethal factor endopeptidase, Shiga Toxin, Saporin Toxin, Ricin Toxin, and any combination thereof.

8. The method of claim 1, wherein the molecule is a small molecule.

9. The method of claim 8, wherein the small molecule is a peptidomimetic.

10. The method of claim 1, wherein the molecule is a peptide or a protein.

11. The method of claim 10, wherein the peptide or the protein is a naturally occurring protein product, is a synthesized protein product, or is produced by expression of a recombinant gene.

12. The method of claim 10, wherein the peptide or protein is expressed from a library comprising test DNA molecules comprising DNA sequences that encode polypeptides, and wherein the peptide or the protein is expressed from the test DNA molecules.

13. The method of claim 12, wherein the polypeptides are 60 or fewer amino acids in length.

14. The method of claim 12, wherein the polypeptides are processed into cyclic or bicyclic peptides in the host cell.

15. The method of claim 1, wherein the first test protein is YAP or TAZ, the second test protein is TEAD, and the third test protein is VGLL4.

16. The method of claim 1, wherein the animal cell is a mammalian cell.

* * * * *

SEQUENCE LISTING

```
Sequence total quantity: 63
SEQ ID NO: 1            moltype = AA  length = 258
FEATURE                 Location/Qualifiers
source                  1..258
                        mol_type = protein
                        organism = Vibrio cholerae
SEQUENCE: 1
MVKIIFVFFI FLSSFSYAND DKLYRADSRP PDEIKQSGGL MPRGQSEYFD RGTQMNINLY  60
DHARGTQTGF VRHDDGYVST SISLRSAHLV GQTILSGHST YYIYVIATAP NMFNVNDVLG  120
AYSPHPDEQE VSALGGIPYS QIYGWYRVHF GVLDEQLHRN RGYRDRYYSN LDIAPAADGY  180
GLAGFPPEHR AWREEPWIHH APPGCGNAPR SSMSNTCDEK TQSLGVKFLD EYQSKVKRQI  240
FSGYQSDIDT HNRIKDEL                                                258

SEQ ID NO: 2            moltype = AA  length = 593
FEATURE                 Location/Qualifiers
source                  1..593
                        mol_type = protein
                        organism = Salmonella enterica
SEQUENCE: 2
MLILNGFSSA TLALITPPFL PKGGKALSQS GPDGLASITL PLPISAERGF APALALHYSS  60
GGGNGPFGVG WSCATMSIAR RTSHGVPQYN DSDEFLGPDG EVLVQTLSTG DAPNPVTCFA  120
YGDVSFPQSY TVTRYQPRTE SSFYRLEYWV GNSNGDDFWL LHDSNGILHL LGKTAAARLS  180
DPQAASHTAQ WLVEESVTPA GEHIYYSYLA ENGDNVDLNG NEAGRDRSAM RYLSKVQYGN  240
ATPAADLYLW TSATPAVQWL FTLVFDYGER GVDPQVPPAF TAQNSWLARQ DPFSLYNYGF  300
EIRLHRLCRQ VLMFHHFPDE LGEADTLVSR LLLEYDENPI LTQLCAARTL AYEGDGYRRA  360
PVNNMMPPPP PPPPPMMGGN SSRPKSKWAI VEESKQIQAL RYYSAQGYSV INKYLRGDDY  420
PETQAKETLL SRDYLSTNEP SDEEFKNAMS VYINDIAEGL SSLPETDHRV VYRGLKLDKP  480
ALSDVLKEYT TIGNIIIDKA FMSTSPDKAW INDTILNIYL EKGHKGRILG DVAHFKGEAE  540
MLFPPNTKLK IESIVNCGSQ DFASQLSKLR LSDDATADTN RIKRIINMRV LNS         593

SEQ ID NO: 3            moltype = AA  length = 601
FEATURE                 Location/Qualifiers
source                  1..601
```

```
                        mol_type = protein
                        organism = Mycoplasma pneumoniae
SEQUENCE: 3
MSENLYFQGH MPNPVRFVYR VDLRSPEEIF EHGFSTLGDV RNFFEHILST NFGRSYFIST  60
SETPTAAIRF FGSWLREYVP EHPRRAYLYE IRADQHFYNA RATGENLLDL MRQRQVVFDS  120
GDREMAQMGI RALRTSFAYQ REWFTDGPIA AANVRSAWLV DAVPVEPGHA HHPAGRVVET  180
TRINEPEMHN PHYQELQTQA NDQPWLPTPG IATPVHLSIP QAASVADVSE GTSASLSFAC  240
PDWSPPSSNG ENPLDKCIAE KIDNYNLQSL PQYASSVKEL EDTPVYLRGI KTQKTFMLQA  300
DPQNNNVFLV EVNPKQKSSF PQTIFFWDVY QRICLKDLTG AQISLSLTAF TTQYAGQLKV  360
HLSVSAVNAV NQKWKMTPQD IAITQFRVSS ELLGQTENGL FWNTKSGGSQ HDLYVCPLKN  420
PPSDLEELQI IVDECTTHAQ FVTMRAASTF FVDVQLGWYW RGYYYTPQLS GWSYQMKTPD  480
GQIFYDLKTS KIFFVQDNQN VFFLHNKLNK QTGYSWDWVE WLKHDMNEDK DENFKWYFSR  540
DDLTIPSVEG LNFRHIRCYA DNQQLKVIIS GSRWGGWYST YDKVESNVED KILVKDGFDR  600
F                                                                 601

SEQ ID NO: 4            moltype = AA  length = 250
FEATURE                 Location/Qualifiers
source                  1..250
                        mol_type = protein
                        organism = Streptococcus pyogenes
SEQUENCE: 4
MLKKRYQLAM ILLLSCFSLV WQTEGLVELF VCEHYERAVC EGTPAYFTFS DQKGAETLIK  60
KRWGKGLVYP RAEQEAMAAY TCQQAGPINT SLDKAKGKLS QLTPELRDQV AQLDAATHRL  120
VIPWNIVVYR YVYETFLRDI GVSHADLTSY YRNHQFNPHI LCKIKLGTRY TKHSFMSTTA  180
LKNGAMTHRP VEVRICVKKG AKAAFVEPYS AVPSEVELLF PRGCQLEVVG AYVSQDHKKL  240
HIEAYFKGSL                                                        250

SEQ ID NO: 5            moltype = AA  length = 264
FEATURE                 Location/Qualifiers
source                  1..264
                        mol_type = protein
                        organism = Pseudomonas syringae
SEQUENCE: 5
MNINRQLPVS GSERLLTPDV GVSRQACSER HYSTGQDRHD FYRFAARLHV DAQCFGLSID  60
DLMDKFSDKH FRAEHPEYRD VYPEECSAIY MHTAQDYSSH LVRGEIGTPL YREVNNYLRL  120
QHENSGREAE IDNHDEKLSP HIKMLSSALN RLMDVAAFRG TVYRGIRGDL DTIARLYHLF  180
DTGGRYVEPA FMSTTRIKDS AQVFEPGTPN NIAFQISLKR GADISGSSQA PSEEEIMLPM  240
MSEFVIEHAS ALSEGKHLFV LSQI                                        264

SEQ ID NO: 6            moltype = AA  length = 601
FEATURE                 Location/Qualifiers
source                  1..601
                        mol_type = protein
                        organism = Vibrio cholerae
SEQUENCE: 6
MKTIISLIFI MFPLFVSAHN GNFYRADSRS PNEIKDLGGL YPRGYYDFFE RGTPMSISLY  60
DHARGAPSGN TRYDDGFVST TTDIDSAHEI GQNILSGYTE YYIYLIAPAP NLLDVNAVLG  120
RYSPHPQENE YSALGGIPWT QVIGWYVVNN GVLDRNIHRN RQFRADLFNN LSPALPSESY  180
QFAGFEPEHP AWRQEPWINF APPGCGRNVR LTKHINQQDC SNSQEELVYK KLQDLRTQFK  240
VDKKLKLVNK TSSNNIIFPN HDFIREWVDL DGNGDLSYCG FTVDSDGSRK RIVCAHNNGN  300
FTYSSINISL SDYGWPKGQR FIDANGDGLV DYCRVQYVWT HLYCSLSLPG QYFSLDKDAG  360
YLDAGYNNSR AWAKVIGTNK YSFCRLTSNG YICTDIDSYS TAFKDDDQGW ADSRYWMDID  420
GNGGDDYCRL VYNWTHLRCN LQGKDGLWKR VESKYLDGGY PSLRFKIKMT SNKDNYCRIV  480
RNHRVMECAY VSDNGEFHNY SLNMPFSLYN KNDIQFIDID GDNRDDICRY NSAPNTMECY  540
LNQDKSFSQN KLVLYLSAKP ISSLGSGSSK IIRTFNSEKN SSAYCYNAGY GTLRCDEFVI  600
Y                                                                 601

SEQ ID NO: 7            moltype = AA  length = 476
FEATURE                 Location/Qualifiers
source                  1..476
                        mol_type = protein
                        organism = Bacillus cereus
SEQUENCE: 7
MKEIIRNLVR LDVRSDVDEN SKKTQELVEK LPHEVLELYK NVGGEIYITD KRLTQHEELS  60
DSSHKDMFIV SSEGKSFPLR EHFVFAKGGK EPSLIIHAED YASHLSSVEV YYELGKAIIR  120
DTFPLNQKEL GNPKFINAIN EVNQQKEGKG VNAKADEDGR DLLFGKELKK NLEHGQLVDL  180
DLISGNLSEF QHVFAKSFAL YYEPHYKEAL KSYAPALFNY MLELDQMRFK EISDDVKEKN  240
KNVLDFKWYT RKAESWGVQT FKNWKENLTI SEKDIITGYT GSKYDPINEY LRKYDGEIIP  300
NIGGDLDKKS KKALEKIENQ IKNLDAALQK SKITENLIVY RRVSELQFGK KYEDYNLRQN  360
GIINEEKVME LESNFKGQTF IQHNYMSTSL VQDPHQSYSN DRYPILLEIT IPEGVHGAYI  420
ADMSEYPGQY EMLINRGYTF KYDKFSIVKP TREEDKGKEY LKVNLSIYLG NLNREK      476

SEQ ID NO: 8            moltype = AA  length = 487
FEATURE                 Location/Qualifiers
REGION                  1..487
                        note = strain V583
source                  1..487
                        mol_type = protein
                        organism = Enterococcus faecalis
```

```
SEQUENCE: 8
MSQLNKWQKE LQALQKANYQ ETDNQLFNVY RQSLIDIKKR LKVYTENAES LSFSTRLEVE  60
RLFSVADEIN AILQLNSPKV EKTIKGYSAK QAEQGYYGLW YTLEQSQNIA LSMPLINHDY  120
IMNLVNAPVA GKRLSKRLYK YRDELAQNVT NNIITGLFEG KSYAEIARWI NEETEASYKQ  180
ALRIARTEAG RTQSVTTQKG YEEAKELGIN IKKKWLATID KHTRRTHQEL DGKEVDVDEE  240
FTIRGHSAKG PRMFGVASED VNCRCTTIEV VDGISPELRK DNESKEMSEF KSYDEWYADR  300
IRQNESKPKP NFTELDFFGQ SDLQDDSDKW VAGLKPEQVN AMKDYTSDAF AKMNKILRNE  360
KYNPREKPYL VNIIQNLDDA ISKFKLKHDI ITYRGVSANE YDAILNGNVF KEFKSTSINK  420
KVAEDFLNFT SANKDGRVVK FLIPKGTQGA YIGTNSSMKK ESEFLLNRNL KYTVEIVDNI  480
LEVTILG                                                          487

SEQ ID NO: 9            moltype = AA  length = 457
FEATURE                 Location/Qualifiers
source                  1..457
                        mol_type = protein
                        organism = Pseudomonas aeruginosa
SEQUENCE: 9
MHIQSSQQNP SFVAELSQAV AGRLGQVEAR QVATPREAQQ LAQRQEAPKG EGLLSRLGAA  60
LARPFVAIIE WLGKLLGSRA HAATQAPLSR QDAPPAASLS AAEIKQMMLQ KALPLTLGGL  120
GKASELATLT AERLAKDHTR LASGDGALRS LATALVGIRD GSLIEASRTQ AARLLEQSVG  180
GIALQQWGTA GGAASQHVLS ASPEQLREIA VQLHAVMDKV ALLRHAVESE VKGEPVDKAL  240
ADGLVEHFGL EAEQYLGEHP DGPYSDAEVM ALGLYTNGEY QHLNRSLRQG RELDAGQALI  300
DRGMSAAFEK SGPAEQVVKT FRGTQGRDAF EAVKEGQVGH DAGYLSTSRD PSVARSFAGL  360
GTITTLFGRS GIDVSEISIE GDEQEILYDK GTDMRVLLSA KDGQGVTRRV LEEATLGERS  420
GHSEGLLDAL DLATGTDRSG KPQEQDLRLR MRGLDLA                         457

SEQ ID NO: 10           moltype = AA  length = 265
FEATURE                 Location/Qualifiers
REGION                  1..265
                        note = Description of Unknown: CdtB toxin sequence
source                  1..265
                        mol_type = protein
                        organism = unidentified
SEQUENCE: 10
MKKIICLFLS FNLAFANLEN FNVGTWNLQG SSAATESKWS VSVRQLVSGA NPLDILMIQE  60
AGTLPRTATP TGRHVQQGGT PIDEYEWNLG TLSRPDRVFI YYSRVDVGAN RVNLAIVSRM  120
QAEEVIVLPP PTTVSRPIIG IRNGNDAFFN IHALANGGTD VGAIITAVDA HFANMPQVNW  180
MIAGDFNRDP STITSTVDRE LANRIRVVFP TSATQASGGT LDYAITGNSN RQQTYTPPLL  240
AAILMLASLR SHIVSDHFPV NFRKF                                      265

SEQ ID NO: 11           moltype = AA  length = 560
FEATURE                 Location/Qualifiers
source                  1..560
                        mol_type = protein
                        organism = Corynebacterium diphtheriae
SEQUENCE: 11
MSRKLFASIL IGALLGIGAP PSAHAGADDV VDSSKSFVME NFSSYHGTKP GYVDSIQKGI  60
QKPKSGTQGN YDDDWKGFYS TDNKYDAAGY SVDNENPLSG KAGGVVKVTY PGLTKVLALK  120
VDNAETIKKE LGLSLTEPLM EQVGTEEFIK RFGDGASRVV LSLPFAEGSS SVEYINNWEQ  180
AKALSVELEI NFETRGKRGQ DAMYEYMAQA CAGNRVRRSV GSSLSCINLD WDVIRDKTKT  240
KIESLKEHGP IKNKMSESPN KTVSEEKAKQ YLEEFHQTAL EHPELSELKT VTGTNPVFAG  300
ANYAAWAVNV AQVIDSETAD NLEKTTAALS ILPGIGSVMG IADGAVHHNT EEIVAQSIAL  360
SSLMVAQAIP LVGELVDIGF AAYNFVESII NLFQVVHNSY NRPAYSPGHK TQPFLHDGYA  420
VSWNTVEDSI IRTGFQGESG HDIKITAENT PLPIAGVLLP TIPGKLDVNK SKTHISVNGR  480
KIRMRCRAID GDVTFCRPKS PVYVGNGVHA NLHVAFHRSS SEKIHSNEIS SDSIGVLGYQ  540
KTVDHTKVNS KLSLFFEIKS                                            560

SEQ ID NO: 12           moltype = AA  length = 621
FEATURE                 Location/Qualifiers
REGION                  1..621
                        note = Description of Unknown: ExoU/VipB toxin sequence
source                  1..621
                        mol_type = protein
                        organism = unidentified
SEQUENCE: 12
MKLAEIMTKS RKLKRNLLEI SKTEAGQYSV SAPEHKGLVL SGGGAKGISY LGMIQALQER  60
GKIKNLTHVS GASAGAMTAS ILAVGMDIKD IKKLIEGLDI TKLLDNSGVG FRARGDRFRN  120
ILDVIYMMQM KKHLESVQQP IPPEQQMNYG ILKQKIALYE DKLSRAGIVI NNVDDIINLT  180
KSVKDLEKLD KALNSIPTEL KGAKGEQLEN PRLTLGDLGR LRELLPEENK HLIKNLSVVV  240
TNQTKHELER YSEDTTPQQS IAQVVQWSGA HPVLFVPGRN AKGEYIADGG ILDNMPEIEG  300
LDREEVLCVK AEAGTAFEDR VNKAKQSAME AISWFKARMD SLVEATIGGK WLHATSSVLN  360
REKVYYNIDN MIYINTGEVT TTNTSPTPEQ RARAVKNGYD QTMQLLDSHK QTFDHPLMAI  420
LYIGHDKLKD ALIDEKSEKE IFEASAHAQA ILHLQEQIVK EMNDGDYSSV QNYLDQIEDI  480
LTVDAKMDDI QKEKAFALCI KQVNFLSEGK LETYLNKVEA EAKAAAEPSW ATKILNLLWA  540
PIEWVVSLFK GPAQDFKVEV QPEPVKVSTS ENQETVSNQK DINPAVEYRK IIAEVRREHT  600
DPSPSLQEKE RVGLSTTFGG H                                          621

SEQ ID NO: 13           moltype = AA  length = 211
FEATURE                 Location/Qualifiers
```

-continued

```
source                 1..211
                       mol_type = protein
                       organism = Pseudomonas syringae
SEQUENCE: 13
MNRVSGSSSA TWQAVNDLVE QVSERTTLST TGYQTAMGRL NKPEKSDADA LMTMRRAQQY  60
TDSAKRTYIS ETLMNLADLQ QRKIYRTNSG NLRGAIEMTP TQLTDCVQKC REEGFSNCDI  120
QALEIGLHLR HKLGISDFTI YSNRKLSHNY VVIHPSNAFP KGAIVDSWTG QGVVELDFKT  180
RLKFKHREEN YAVNANMHEW IERYGQAHVI D                                211

SEQ ID NO: 14          moltype = AA  length = 204
FEATURE                Location/Qualifiers
source                 1..204
                       mol_type = protein
                       organism = Pseudomonas syringae
SEQUENCE: 14
MGNICGTSGS RHVYSPSHTQ RITSAPSTST HVGGDTLTSI HQLSHSQREQ FLNMHDPMRV  60
MGLDHDTELF RTTDSRYIKN DKLAGNPQSM ASILMHEELR PNRFASHTGA QPHEARAYVP  120
KRIKATDLGV PSLNVMTGSL ARDGIRAYDH MSDNQVSVKM RLGDFLERGG KVYADASSVA  180
DDGETSQALI VTLPKGQKVP VERV                                        204

SEQ ID NO: 15          moltype = AA  length = 493
FEATURE                Location/Qualifiers
source                 1..493
                       mol_type = protein
                       organism = Pseudomonas syringae
SEQUENCE: 15
MQIKNSHLYS ASRMVQNTFN ASPKMEVTNA IAKNNEPAAL SATQTAKTHE GDSKGQSSNN  60
SKLPFRAMRY AAYLAGSAYL YDKTANNFFL STTSLHDGKG GFTSDARLND AQDKARKRYQ  120
NNHSSTLENK NSLLSPLRLC GENQFLTMID YRAATKIYLS DLVDTEQAHT SILKNIMCLK  180
GELTNEEAIK KLNPEKTPKD YDLTNSEAYI SKNKYSLTGV KNEETGSTGY TSRSITKPFV  240
EKGLKHFIKA THGEKALTPK QCMETLDNLL RKSITLNSDS QFAAGQALLV FRQVYAGEDA  300
WGDAERVILK SHYNRGTVLQ DEADKIELSR PFSEQDLAKN MFKRNTSIAG PVLYHAYIYI  360
QEKIFKLPPD KIEDLKHKSM ADLKNLPLTH VKLSNSGVGF EDASGLGDSF TALNATSCVN  420
HARIMSGEPP LSKDDVVILI GCLNAVYDNS SGIRHSLREI ARGCFVGAGF TVQDGDDFYK  480
QICKNASKQF YNG                                                    493

SEQ ID NO: 16          moltype = AA  length = 530
FEATURE                Location/Qualifiers
source                 1..530
                       mol_type = protein
                       organism = Vibrio cholerae
SEQUENCE: 16
MFKISVSQQA NVMSTSDTAQ RSSLKISIKS ICNKSLSKKL HTLAEKCRRF SQELKEHTAS  60
KKQIVEQATT TVRESSLTKS DSELGSSRSL LTSDVLSSSS SHEDLTAVNL EDNDSVFVTI  120
ESSSELIVKQ DGSIPPAPPL PGNIPPAPPL PSAGNIPTAP GLPKQKATTE SVAQTSDNRS  180
KLMEEIRQGV KLRATPKSSS TEKSASDPHS KLMKELINHG AKLKKVSTSD IPVPPPLPAA  240
FASKPTDGRS ALLSEIAGFS KDRLRKAGSS ETLNVSQPTV AESSIPEAYD LLLSDEMFNL  300
SPKLSETELN TLADSLADYL FKAADIDWMQ VIAEQTKGST QATSLKSQLE QAPEYVKAFC  360
DEILKFPDCY KSADVASPES PKAGPSSVID VALKRLQAGR NRLFSTIDAK GTNELKKGEA  420
ILESAINAAR SVMTAEQKSA LLSSNVKSAT FKVFSELPCM EGFAEQNGKA AFNALRLAFY  480
SSIQSGDTAQ QDIARFMKEN LATGFSGYSY LGLTSRVAQL EAQLAALTTK             530

SEQ ID NO: 17          moltype = AA  length = 288
FEATURE                Location/Qualifiers
REGION                 1..288
                       note = Description of Unknown: YopJ toxin sequence
source                 1..288
                       mol_type = protein
                       organism = unidentified
SEQUENCE: 17
MIGPISQINI SGGLSEKETS SLISNEELKN IITQLETDIS DGSWFHKNYS RMDVEVMPAL  60
VIQANNKYPE MNLNLVTSPL DLSIEIKNVI ENGVRSSRFI INMGEGGIHF SVIDYKHING  120
KTSLILFEPA NFNSMGPAML AIRTKTAIER YQLPDCHFSM VEMDIQRSSS ECGIFSFALA  180
KKLYIERDSL LKIHEDNIKG ILSDGENPLP HDKLDPYLPV TFYKHTQGKK RLNEYLNTNP  240
QGVGTVVNKK NETIVNRFDN NKSIVDGKEL SVSVHKKRIA EYKTLLKV               288

SEQ ID NO: 18          moltype = AA  length = 579
FEATURE                Location/Qualifiers
source                 1..579
                       mol_type = protein
                       organism = Pseudomonas sp.
SEQUENCE: 18
MAGINGAGPS GAYFVGHTDP EPASGGAHGS SSGASSSNSP RLPAPPDAPA SQARDRREML  60
LRARPLSRQT REWVAQGMPP TAEAGVPIRP QESAEAAAPQ ARAEERHTPE ADAAASHVRT  120
EGGRTPQALA GTSPRHTGAV PHANRIVQQL VDAGADLAGI NTMIDNAMRR HAIALPSRTV  180
QSILIEHFPH LLAGELISGS ELATAFRAAL RREVRQQEAS APPRTAARSS VRTPERSTVP  240
PTSTESSSGS NQRTLLGRFA GLMTPNQRRP SSASNASASQ RPVDRSPPRV NQVPTGANRV  300
VMRNHGNNEA DAALQGLAQQ GVDMEDLRAA LERHILHRRP IPMDIAYALQ GVGIAPSIDT  360
GESLMENPLM NLSVALHRAL GPRPARAQAP RPAVPVAPAT VSRRPDSARA TRLQVIPARE  420
```

```
DYENNVAYGV RLLSLNPGAG VRETVAAFVN NRYERQAVVA DIRAALNLSK QFNKLRTVSK  480
ADAASNKPGF KDLADHPDDA TQCLFGEELS LTSSVQQVIG LAGKATDMSE SYSREANKDL  540
VFMDMKKLAQ FLAGKPEHPM TRETLNAENI AKYAFRIVP                         579

SEQ ID NO: 19          moltype = AA  length = 1116
FEATURE                Location/Qualifiers
REGION                 1..1116
                       note = Description of Unknown: SdbA toxin sequence
source                 1..1116
                       mol_type = protein
                       organism = unidentified
SEQUENCE: 19
MHKKYNYYSL EKEKKTFWQH ILDILKAPFR LPGWVVSFFL ARNITHVALN PNNIPQQRLI  60
HLTKTSNRPE DDIVVINFKK RPPHKWFNDT LIKIANTIAA LPFVTPRLRT RLHYDNENDI  120
NHVNKLLAEI DALVQGKSKQ KYCKGRAFDW SKIHLKGLEF LDPKMRGYVY EQLHEKYGYV  180
SYTTKRKPNI EFFTLKTPDG SELDSVQVTG EDEEKKPMGE RKFIITCIAR DQNFINWIKD  240
LNYTAKNLGA TAISFNYRGV DYSRGLVWTE NNLVDDILAQ VQRLISLGAD PKNICLDGMC  300
IGGAVATIAA AKLHEKGMKV KLNNERSFTS LSSLVFGFIV PELQTANWWS PLTYGRFLLA  360
GVVYALLTPL IWLAGWPVDV TKAWNRIPAQ DKMYSVVRDK DNGLYDGVIH DHFCSIASLV  420
DSQINSILYK LSTDQPLTEE EKQILCDDQF SHHFKPSQSV LKNPKYKGPH FISRQDLVAE  480
LGHREEYTNH DYFLDRLREK FQLDRATRPV ALAEDGEKDI DGISSQLSNN KERPLIIASS  540
GGTGHISATH GIINDLQSKT DNVVITQHHA ELYKNKPFSI TSVLIRIGVW FTSLPILEDI  600
LKGVMRFIGY PVLPSSSIFW DQMSKIQQSE TKKENGIETG RTRPYVDMLL DIYPEGYEYT  660
AFNNATHLTS SIEDIQTMIS FKGHVEEDNR NIVYQNILQR LMHAAKQNTP YTRLISTQAL  720
SLGAICDAVK YYNTVFLPVY NAERGTSYQP IAIDQYMTDL PSLGCIHFMN NLEELTSEQR  780
QLMEIHAVNM SEPFKEAHFG KEQGFKAVHN IDPRNNPMIR NAFKDPSLTK YLDKTQSFDL  840
HFNVYKKEKQ NALPVLNGKE KITIKPHAKI ASIMIGSLAA NASADYAKYL LNQGYEHIFL  900
FGGLNDSIAA RIDQIINSYP APTRDEIRKK IILLGNQSDV EMAPIMTRSN CVVIRGGGLS  960
VMEQMAMPIM DDKIVLLHHE DNEEGPLTSG LSWEDGNSDK LIEYLSEKGA YAKKTSPGLC  1020
SGHLHEAEKS FEKKYHGQLK STETKKKVDL TIPQQETYSL KKEWDRKTGY TESGHILSHQ  1080
HRFFNTIPEV REPFCSKEDL HHNELSSQSL VSVSAG                            1116

SEQ ID NO: 20          moltype = AA  length = 965
FEATURE                Location/Qualifiers
source                 1..965
                       mol_type = protein
                       organism = Legionella pneumophila
SEQUENCE: 20
MSRSKDEVLE ANDSLFGITV QTWGTNDRPS NGMMNFADQQ FFGGDVGHAS INMKLPVTDK  60
TKQWIEKYCY SQTYDQFKKV KGNEDKTYEE YLKTAKRLIP VELKTQVTRK AQYDSNGNLV  120
TTHEKAYEQI YFDIDWSWWP GRLQNTEDDM VWEREGKHFE YDEKWKEYLQ PEQRVHRGKL  180
GSRKMDYAPT SIIHQRDIPT SELEKITRDH KIHTIEEKLN VVKLLQSKID EMPHTKMSPS  240
MELMFKNLGI NVEKLLDETK DNGVDPTNLE AMREYLTNRL TERKLELETE LSEAKKEVDS  300
TQVKNKVEDV YYDFEYKLNQ VRKKMEEVNS QLEKMDSLLH KLEGNTSGPI PYTAEIDELM  360
SVLPFLKEEL ELENGTLSPK SIENLIDHID ELKNELASKQ EKKNERNLNL IKKYEELCEQ  420
YKDDEEGLEE ALWEEGIDVE EVNSAKKDIS KPAPEIQKLT DLQEQLRNHK ESGVKLSSEL  480
EETLNSSVKM WKTKIDSPCQ VISESSVKAL VSKINSTRPE LVKEKEQLPE QEESLSKEAK  540
KAQEELIKIQ EFSQFYSENS SAYMVIGLPP HHQVSLPLAV NGKRGLHPEA MLKKMHELVA  600
GPEKKEFNLH TNNCSLTSIE VLSAGAQHDP LLHSIMGTRA LGFFGTPQQV LENAKLTSKT  660
INEGKKSNIF TPLVTASPLD RALGYAMSIY MDPEASKAKQ NAGLALGVLV GLAKTPGIII  720
GSLLNPKQGF NDILNTLNLV YSRNSTGLKV GLTLMALPAM IVLAPLAAIQ KGVEVIAETI  780
AKPFKLIANL FKQKPESTDE ITVSVGSKKV AEKEGSYSNT ALAGLVNSKI KSKIDENTIT  840
VEFQKSPQKM IEEFESQLKE NPGKVVVLSE KAHNAVLKFV SKSDDEALKQ KFYDCCNQSV  900
ARSQKFAPKT RDEIDELVEE VTSTDKTELT TSPRQEPSMS STIDEEENID SEHQIETGTE  960
STMRI                                                              965

SEQ ID NO: 21          moltype = AA  length = 665
FEATURE                Location/Qualifiers
source                 1..665
                       mol_type = protein
                       organism = Legionella pneumophila
SEQUENCE: 21
MKTKQEVSQQ DKLKDSKSST PLQTKETWFI SDALNITFDP YDFSISVTEQ APMPYRIVFS  60
GGGSRILAHI GALDELTRHG LKFTEFSGSS AGAMVAAFAY LGYNCSEIKQ IISWFNEDKL  120
LDSPLIFNFN NIKQIFNKGG LSSAKLMRQA ANYVILKKVM DIISDEKFKT RFAKFQNFLE  180
ENIYRCPENI TFQTLARIKE ICPECELGEK LFITGTNLST QKHEVFSIDT TPSMALADAI  240
IISANLPIAF ERICYQGNVY SDGGISNNLP AHCFSEKGHK TTFLKHKDDV DFSVLALQFD  300
NGLEENALYS QNPIPKWSWL SNTFYSLITG HPNVTENWYE DLQILRRHAH QSILIKTPTI  360
ALTNLTISQD TKKALVESGR TAAKTYLELH EFYTDDYGNI RHNECLHEKF QKPEELLDYC  420
VLHSHFELLK KIKQAISCSQ YLEKGYKHYL CELCDNLLPP QLKCPNEGSG TEQPEIKLEK  480
DTIICEKNNN SGLTFSMTFF GVPSPLVKTL NQDSPELKIK LFTGLYPILI QNWQNLCPVS  540
GISGILNSIR MSFVEISSTD TCIKTLIDKL NEIEIGHFLI FVFKAALKNY DKHDFILLLK  600
NLKHLHHSIE LIRNKPFHSD DRFYGQWSFE GHDPKRILEF IKSDDISGLM TILEDKKALP  660
NNKPN                                                              665

SEQ ID NO: 22          moltype = AA  length = 246
FEATURE                Location/Qualifiers
source                 1..246
                       mol_type = protein
```

```
                        organism = Legionella pneumophila
SEQUENCE: 22
MVSLEHIQKL ISECRKLGKD GLDNGTNGLI PELEIDVVPP SAFLGVGNNP AIFVNSKTYK  60
LMRTTHEKWV ENKTIVFKSY LLSQPAIKII GAIVHETGHA FNVAAKIPNT EANACIFEIE  120
VLMRLFQVKS PLLLGCTELD MQSYFKSRLT DYNKCVKDCQ CLAEMVEFIT HQFKLDEVSI  180
SEKENQIPLL SISNKWPGLF AKKQIAPDMD KLLTSPVTIT PEVKILFYQL VKEHFHSPET  240
EIKLDI                                                           246

SEQ ID NO: 23           moltype = AA  length = 644
FEATURE                 Location/Qualifiers
source                  1..644
                        mol_type = protein
                        organism = Legionella pneumophila
SEQUENCE: 23
MYKIYSYLGW RIDMKTENLP QAGQEAQIDK KIHFIWVGHI MPQKNIQVVS EWAEKNPGYE  60
TIIWVDKKIA PAKELDLFIL DMKSKGITVK DINEEGVCRD SIRHELDQES PNYGMVSDML  120
RLNILAAEGG IYLDSDILCS APFPDEIYAP FGFLLSPWSQ GANNTLCNDI ILCSKGNQII  180
QQLADAIEQS YIARDSFEFT HEYASMKETK GERIAKTLGV TGPGFLFHQL KKMGILNDKS  240
EMEAIHWELQ DQRYLIDGSV KEPDYFYVPQ NNTNDASWVP SIKRPGIENM SFQERLENAV  300
QLIAFDIQKT GLFNLDHYAN ELKVKQNSWC IAAETSPELK PDSYLLIRPR DKTGEWTLYY  360
VDEDKKLNPV TLPVIKGAIK LSEVSDPLRK FHTLLSQVSD PVNPTAHELK QIGRALIELK  420
PRQDEWHCKN KWSGAEEIAQ ELWQRITSNE TLRAQIKQCF TQFESLKPRV AELGLTRASG  480
AGTEVEAHES TVKEQEIISQ NTVGEEGTKE KNSVQLASEN SSDEKIKTAH DLIDEIIQDV  540
IQLDGKLGLL GGNTRQLEDG RVINIPNGAA MIFDDYKKYK QGELTAESAL ESMIKIAKLS  600
NQLNRHTFFN QRQPETGQFY KKVAAIDLQT TIAAEYDNNH GLRI                 644

SEQ ID NO: 24           moltype = AA  length = 219
FEATURE                 Location/Qualifiers
source                  1..219
                        mol_type = protein
                        organism = Yersinia sp.
SEQUENCE: 24
MKISSFISTS LPLPTSVSGS SSVGEMSGRS VSQQTSDQYA NNLAGRTESP QGSSLASRII  60
ERLSSVAHSV IGFIQRMFSE GSHKPVVTPA PTPAQMPSPT SFSDSIKQLA AETLPKYMQQ  120
LNSLDAEMLQ KNHDQFATGS GPLRGSITQC QGLMQFCGGE LQAEASAILN TPVCGIPFSQ  180
WGTIGGAASA YVASGVDLTQ AANEIKGLAQ QMQKLLSLM                       219

SEQ ID NO: 25           moltype = AA  length = 543
FEATURE                 Location/Qualifiers
source                  1..543
                        mol_type = protein
                        organism = Salmonella sp.
SEQUENCE: 25
MLKYEERKLN NLTLSSFSKV GVSNDARLYI AKENTDKAYV APEKFSSKVL TWLGKMPLFK  60
NTEVVQKHTE NIRVQDQKIL QTFLHALTEK YGETAVNDAL LMSRINMNKP LTQRLAVQIT  120
ECVKAADEGF INLIKSKDNV GVRNAALVIK GGDTKVAEKN NDVGAESKQP LLDIALKGLK  180
RTLPQLEQMD GNSLRENFQE MASGNGPLRS LMTNLQNLNK IPEAKQLNDY VTTLTNIQVG  240
VARFSQWGTC GGEVERWVDK ASTHELTQAV KKIHVIAKEL KNVTAELEKI EAGAPMPQTM  300
SGPTLGLARF AVSSIPINQQ TQVKLSDGMP VPVNTLTFDG KPVALAGSYP KNTPDALEAH  360
MKMLLEKECS CLVVLTSEDQ MQAKQLPPYF RGSYTFGEVH TNSQKVSSAS QGEAIDQYNM  420
QLSCGEKRYT IPVLHVKNWP DHQPLPSTDQ LEYLADRVKN SNQNGAPGRS SSDKHLPMIH  480
CLGGVGRTGT MAAALVLKDN PHSNLEQVRA DFRDSRNNRM LEDASQFVQL KAMQAQLLMT  540
TAS                                                              543

SEQ ID NO: 26           moltype = AA  length = 240
FEATURE                 Location/Qualifiers
source                  1..240
                        mol_type = protein
                        organism = unidentified
                        note = Salmonella typhimurium
SEQUENCE: 26
MTNITLSTQH YRIHRSDVEP VKEKTTEKDI FAKSITAVRN SFISLSTSLS DRFSLHQQTD  60
IPTTHFHRGN ASEGRAVLTS KTVKDFMLQK LNSLDIKGNA SKDPAYARQT CEAILSAVYS  120
NNKDQCCKLL ISKGVSITPF LKEIGEAAQN AGLPGEIKNG VFTPGGAGAN PFVVPLIASA  180
SIKYPHMFIN HNQQVSFKAY AEKIVMKEVT PLFNKGTMPT PQQFQLTIEN IANKYLQNAS  240

SEQ ID NO: 27           moltype = AA  length = 561
FEATURE                 Location/Qualifiers
source                  1..561
                        mol_type = protein
                        organism = unidentified
                        note = Salmonella typhimurium
SEQUENCE: 27
MQIQSFYHSA SLKTQEAFKS LQKTLYNGMQ ILSGQGKAPA KAPDARPEII VLREPGATWG  60
NYLQHQKASN HSLHNLYNLQ RDLLTVAATV LGKQDPVLTS MANQMELAKV KADRPATKQE  120
EAAAKALKKN LIELIAARTQ QQDGLPAKEA HRFAAVAFRD AQVKQLNNQP WQTIKNTLTH  180
NGHHYTNTQL PAAEMKIGAK DIFPSAYEGK GVCSWDTKNI HHANNLWMST VSVHEDGKDK  240
TLFCGIRHGV LSPYHEKDPL LRHVGAENKA KEVLTAALFS KPELLNKALA GEAVSLKLVS  300
VGLLTASNIF GKEGTMVEDQ MRAWQSLTQP GKMIHLKIRN KDGDLQTVKI KPDVAAFNVG  360
```

```
VNELALKLGF GLKASDSYNA EALHQLLGND LRPEARPGGW VGEWLAQYPD NYEVVNTLAR  420
QIKDIWKNNQ HHKDGGEPYK LAQRLAMLAH EIDAVPAWNC KSGKDRTGMM DSEIKREIIS  480
LHQTHMLSAP GSLPDSGGQK IFQKVLLNSG NLEIQKQNTG GAGNKVMKNL SPEVLNLSYQ  540
KRVGDENIWQ SVKGISSLIT S                                            561

SEQ ID NO: 28          moltype = AA  length = 685
FEATURE                Location/Qualifiers
source                 1..685
                       mol_type = protein
                       organism = unidentified
                       note = Salmonella typhimurium
SEQUENCE: 28
MVTSVRTQPP VIMPGMQTEI KTQATNLAAN LSAVRESATT TLSGEIKGPQ LEDFPALIKQ  60
ASLDALFKCG KDAEALKEVF TNSNNVAGKK AIMEFAGLFR SALNATSDSP EAKTLLMKVG  120
AEYTAQIIKD GLKEKSAFGP WLPETKKAEA KLENLEKQLL DIIKNNTGGE LSKLSTNLVM  180
QEVMPYIASC IEHNFGCTLD PLTRSNLTHL VDKAAAKAVE ALDMCHQKLT QEQGTSVGRE  240
ARHLEMQTLI PLLLRNVFAQ IPADKLPDPK IPEPAAGPVP DGGKKAEPTG INININIDSS  300
NHSVDNSKHI NNSRSHVDNS QRHIDNSNHD NSRKTIDNSR TFIDNSQRNG ESHHSTNSSN  360
VSHSHSRVDS TTHQTETAHS ASTGAIDHGI AGKIDVTAHA TAEAVTNASS ESKDGKVVTS  420
EKGTTGETTS FDEVDGVTSK SIIGKPVQAT VHGVDDNKQQ SQTAEIVNVK PLASQLAGVE  480
NVKTDTLQSD TTVITGNKAG TTDNDNSQTD KTGPFSGLKF KQNSFLSTVP SVTNMHSMHF  540
DARETFLGVI RKALEPDTST PFPVRRAFDG LRAEILPNDT IKSAALKAQC SDIDKHPELK  600
AKMETLKEVI THHPQKEKLA EIALQFAREA GLTRLKGETD YVLSNVLDGL IGDGSWRAGP  660
AYESYLNKPG VDRVITTVDG LHMQR                                        685

SEQ ID NO: 29          moltype = AA  length = 732
FEATURE                Location/Qualifiers
source                 1..732
                       mol_type = protein
                       organism = Yersinia pseudotuberculosis
SEQUENCE: 29
MKSVKIMGTM PPSISLAKAH ERISQHWQNP VGELNIGGKR YRIIDNQVLR LNPHSGFSLF  60
REGVGKIFSG KMFNFSIARN LTDTLHAAQK TTSQELRSDI PNALSNLFGA KPQTELPLGW  120
KGEPLSGAPD LEGMRVAETD KFAEGESHIS IIETKDKQRL VAKIERSIAE GHLFAELEAY  180
KHIYKTAGKH PNLANVHGMA VVPYGNRKEE ALLMDEVDGW RCSDTLRTLA DSWKQGKINS  240
EAYWGTIKFI AHRLLDVTNH LAKAGVVHND IKPGNVVFDR ASGEPVVIDL GLHSRSGEQP  300
KGFTESFKAP ELGVGNLGAS EKSDVFLVVS TLLHCIEGFE KNPEIKPNQG LRFITSEPAH  360
VMDENGYPIH RPGIAGVETA YTRFITDILG VSADSRPDSN EARLHEFLSD GTIDEESAKQ  420
ILKDTLTGEM SPLSTDVRRI TPKKLRELSD LLRTHLSSAA TKQLDMGGVL SDLDTMLVAL  480
DKAEREGGVD KDQLKSFNSL ILKTYRVIED YVKGREGDTK NSSTEVSPYH RSNFMLSIVE  540
PSLQRIQKHL DQTHSFSDIG SLVRAHKHLE TLLEVLVTLS QQGQPVSSET YGFLNRLAEA  600
KITLSQQLNT LQQQQESAKA QLSILINRSG SWADVARQSL QRFDSTRPVV KFGTEQYTAI  660
HRQMMAAHAA ITLQQEVSEFT DDMRNFTVDS IPLLIQLGRS SLMDEHLVEQ REKLRELTTI  720
AERLNRLERE WM                                                      732

SEQ ID NO: 30          moltype = AA  length = 529
FEATURE                Location/Qualifiers
source                 1..529
                       mol_type = protein
                       organism = Yersinia sp.
SEQUENCE: 30
MFINPRNVSN TFLQEPLRHS SNLTEMPVEA ENVKSKTEYY NAWSEWERNA PPGNGEQREM  60
AVSRLRDCLD RQAHELELNN LGLSSLPELP PHLESLVASC NSLTELPELP QSLKSLQVEN  120
NNLKALPDLP PSLKKLHVRE NDLTDLPELP QSLESLRVDN NNLKALSDLP PSLEYLTASS  180
NKLEELPELQ NLPFLAAIYA DNNLLETLPD LPPSLKKLHV RENDLTDLPE LPQSLESLQV  240
DNNNLKALSD LPPSLEYLTA SSNKLEELPE LQNLPFLAAI YADNNLLETL PDLPPHLEIL  300
VASYNSLTEL PELPQSLKSL RVDNNNLKAL SDLPPSLEYL TASSNKLEEL PELQNLPFLA  360
AIYADNNLLE TLPDLPPSLK KLHVRENDLT DLPELPQSLT FLDVSDNNIS GLSELPPNLY  420
YLDASSNEIR SLCDLPPSLV DLNVKSNQLS ELPALPPHLE RLIASFNYLA EVPELPQNLK  480
QLHVEQNALR EFPDIPESLE ELEMDSERVV DPYEFAHETT DKLEDDVFE              529

SEQ ID NO: 31          moltype = AA  length = 35
FEATURE                Location/Qualifiers
REGION                 1..35
                       note = Description of Unknown: Amatoxin sequence
source                 1..35
                       mol_type = protein
                       organism = unidentified
SEQUENCE: 31
MSDINATRLP IWGIGCNPCV GDDVTTLLTR GEALC                             35

SEQ ID NO: 32          moltype = AA  length = 34
FEATURE                Location/Qualifiers
source                 1..34
                       mol_type = protein
                       organism = unidentified
                       note = Amanita phalloides
SEQUENCE: 32
MSDINATRLP AWLVDCPCVG DDVNRLLTRG ESLC                              34
```

```
SEQ ID NO: 33          moltype = AA  length = 291
FEATURE                Location/Qualifiers
source                 1..291
                       mol_type = protein
                       organism = Ustilago maydis
SEQUENCE: 33
MIKPERSILT ILIGILCLLA YVLANGEPHD GDNEWSSYCS DQGFRRSDDG LVTTPDVGQE  60
SIGKNSINGS ELVDYLQCLK VRLNGQKQVV SNDGWLLLLV QEPSVNVTQK AMSECNYNVS  120
SGHKAGSYIQ VTNTPADYKV ISRRGSYEGD QLPEDVKPYF GVQKTSDYRP ISKRINPNLT  180
LRQLAYNFAA LNMCSLWCNS CISRSCPYYI AELTVHVNNI HHGTVWLHHF CRNASPQGGN  240
LYSTLTISHK DTAYYVGTGW WKVRSTAATT NDVAGDWYPA SWNQYWCGPH Y           291

SEQ ID NO: 34          moltype = AA  length = 219
FEATURE                Location/Qualifiers
source                 1..219
                       mol_type = protein
                       organism = Ustilago maydis
SEQUENCE: 34
MLIFSVLMYL GLLLAGASAL PNGLSPRNNA FCAGFGLSCK WECWCTAHGT GNELRYATAA  60
GCGDHLSKSY YDARAGHCLF SDDLRNQFYS HCSSLNNNMS CRSLSKRTIQ DSATDTVDLG  120
AELHRDDPPP TASDIGKRGK RPRPVMCQCV DTTNGGVRLD AVTRAACSID SFIDGYYTEK  180
DGFCRAKYSW DLFTSGQFYQ ACLRYSHAGT NCQPDPQYE                         219

SEQ ID NO: 35          moltype = AA  length = 316
FEATURE                Location/Qualifiers
source                 1..316
                       mol_type = protein
                       organism = Saccharomyces cerevisiae
SEQUENCE: 35
MTKPTQVLVR SVSILFFITL LHLVVALNDV AGPAETAPVS LLPREAPWYD KIWEVKDWLL  60
QRATDGNWGK SITWGSFVAS DAGVVIFGIN VCKNCVGERK DDISTDCGKQ TLALLVSIFV  120
AVTSGHHLIW GGNRPVSQSD PNGATVARRD ISTVADGDIP LDFSALNDIL NEHGISILPA  180
NASQYVKRSD TAEHTTSFVV TNNYTSLHTD LIHHGNGTYT TFTTPHIPAV AKRYVYPMCE  240
HGIKASYCMA LNDAMVSANG NLYGLAEKLF SEDEGQWETN YYKLYWSTGQ WIMSMKFIEE  300
SIDNANNDFE GCDTGH                                                  316

SEQ ID NO: 36          moltype = AA  length = 296
FEATURE                Location/Qualifiers
source                 1..296
                       mol_type = protein
                       organism = Saccharomyces cerevisiae
SEQUENCE: 36
MGHLAILFSI IAVLNIATAV ASSDSIYLKG HRVGQDIDSL YRVYDNGTMY PVTFNEWLND  60
LTGMNDLATN NATILKRDSS DVSCVTETCQ YVDYHVDDEG VITIDISTYR IPVEWDSGSA  120
GNASYGVSKR DTKYETFCKK KICGINVSGF CNAYDFAVHA FDFGGSVYNP VSGITDRIKE  180
ATKRDKTECL GYELDHVRID PAVDWSISIS TWKQGSANCD TQASADSLKC AAQKALESEH  240
NHQKTAFCIH LDNGGSFNLD IRLISELSFS KYNPWALPCP KYKGSNSWQV VSDCFQ      296

SEQ ID NO: 37          moltype = AA  length = 708
FEATURE                Location/Qualifiers
source                 1..708
                       mol_type = protein
                       organism = Saccharomyces cerevisiae
SEQUENCE: 37
MPRFAIIFAL LIAYSLFLST LFTGSIPDRA NTVTSNAPCQ VVIWDWIRTR RICNCCSRLC  60
YSLLGRSNLS RTAKRGVCTI AGAVLATAAV IVAAVLVGKS SGSATKRGLT KTISVLNHTI  120
PFTDHILNGQ TLSNGTGSNF VTIGFSGYAV HATIKRASTT DIISWVIPES MEPTLARVAS  180
YVSSSSINLA AVPDTGGNAS ALSFQNAVQE FATSWVSMTY DQSYGDLRNV ANDEGGEEIL  240
ILMRKRSYRI SFQVIETGST ALLLRTRRVV SQLITMTYLV TVQARVGIQI GDIFQHYGGI  300
DNYVMTSISV LRTLEDKAFH ENKLLIVREP PNKSNQDANQ SYRLRPFSAN DLIQNLKSVD  360
IGFLAFCSFF DKYAHYPEII MMKITIFISK GNLWSIIYVI QARYVRKRVM KVRGQMPGGL  420
LTNMESLLNI VSTPNLNISE FHIQTHSMSQ SKPMYFQKQC YSSQNNIIYI YNSIHITCGA  480
VYVIVHDVRT PSVFVLIELR NCKPLKNSWC ETTKTSPRDT KIKKNEYNET VCRRAGALLD  540
GRVRTIRFLM MRTHWSRVKG VSCNTANRLS RFCNHVVSYY PSQNATIHLL PTSLRAESLE  600
QQYTTRPLSS SNNRFCCLKS IFINNCKKAC ESPSLVSCNL QQTAELLMVY YLYICEACYV  660
SRNHDLLSKQ CMSTVRAVYV ARMRLPKFRS TFPCMPRLCW LVNGVVVV               708

SEQ ID NO: 38          moltype = AA  length = 768
FEATURE                Location/Qualifiers
source                 1..768
                       mol_type = protein
                       organism = Bacillus anthracis
SEQUENCE: 38
MHVKEKEKNK DENKRKDEER NKTQEEHLKE IMKHIVKIEV KGEEAVKKEA AEKLLEKVPS  60
DVLEMYKAIG GKIYIVDGDI TKHISLEALS EDKKKIKDIY GKDALLHEHY VYAKEGYEPV  120
LVIQSSEDYV ENTEKALNVY YEIGKILSRD ILSKINQPYQ KFLDVLNTIK NASDSDGQDL  180
LFTNQLKEHP TDFSVEFLEQ NSNEVQEVFA KAFAYYIEPQ HRDVLQLYAP EAFNYMDKFN  240
EQEINLSLEE LKDQRMLSRY EKWEKIKQHY QHWSDSLSEE GRGLLKKLQI PIEPKKDDII  300
```

```
HSLSQEEKEL LKRIQIDSSD FLSTEEKEFL KKLQIDIRDS LSEEEKELLN RIQVDSSNPL  360
SEKEKEFLKK LKLDIQPYDI NQRLQDTGGL IDSPSINLDV RKQYKRDIQN IDALLHQSIG  420
STLYNKIYLY ENMNINNLTA TLGADLVDST DNTKINRGIF NEFKKNFKYS ISSNYMIVDI  480
NERPALDNER LKWRIQLSPD TRAGYLENGK LILQRNIGLE IKDVQIIKQS EKEYIRIDAK  540
VVPKSKIDTK IQEAQLNINQ EWNKALGLPK YTKLITFNVH NRYASNIVES AYLILNEWKN  600
NIQSDLIKKV TNYLVDGNGR FVFTDITLPN IAEQYTHQDE IYEQVHSKGL YVPESRSILL  660
HGPSKGVELR NDSEGFIHEF GHAVDDYAGY LLDKNQSDLV TNSKKFIDIF KEEGSNLTSY  720
GRTNEAEFFA EAFRLMHSTD HAERLKVQKN APKTFQFIND QIKFIINS              768

SEQ ID NO: 39          moltype = AA  length = 319
FEATURE                Location/Qualifiers
REGION                 1..319
                       note = Description of Unknown: Shiga toxin sequence
source                 1..319
                       mol_type = protein
                       organism = unidentified
SEQUENCE: 39
MKCILLKWVL CLLLGFSSVS YSREFTIDFS TQQSYVSSLN SIRTEISTPL EHISQGTTSV  60
SVINHTPPGS YFAVDIRGLD VYQARFDHLR LIIEQNNLYV AGFVNTATNT FYRFSDFAHI  120
SVPGVTTVSM TTDSSYTTLQ RVAALERSGM QISRHSLVSS YLALMEFSGN TMTRDASRAV  180
LRFVTVTAEA LRFRQIQREF RQALSETAPV YTMTPGDVDL TLNWGRISNV LPEYRGEDGV  240
RVGRISFNNI SAILGTVAVI LNCHHQGARS VRAVNEESQP ECQITGDRPV IKINNTLWES  300
NTAAAFLNRK SQSLYTTGE                                              319

SEQ ID NO: 40          moltype = AA  length = 299
FEATURE                Location/Qualifiers
source                 1..299
                       mol_type = protein
                       organism = Saponaria officinalis
SEQUENCE: 40
MKSWIMLVVT WLIILQTTVT AVIIYELNLQ GTTKAQYSTF LKQLRDDIKD PNLHYGGTNL  60
PVIKRPVGPP KFLRVNLKAS TGTVSLAVQR SNLYVAAYLA KNNNKQFRAY YFKGFQITTN  120
QLNNLFPEAT GVSNQQELGY GESYPQIQNA AGVTRQQAGL GIKKLAESMT KVNGVARVEK  180
DEALFLLIVV QMVGEAARFK YIENLVLNNF DTAKEVEPVP DRVIILENNW GLLSRAAKTA  240
NNGVFQTPLV LTSYAVPGVE WRVTTVAEVE IGIFLNVDNN GLPSIIYNNI ISGAFGDTY   299

SEQ ID NO: 41          moltype = AA  length = 565
FEATURE                Location/Qualifiers
source                 1..565
                       mol_type = protein
                       organism = Saponaria officinalis
SEQUENCE: 41
MYAVATWLCF GSTSGWSFTL EDNNIFPKQY PIINFTTAGA TVQSYTNFIR AVRGRLTTGA  60
DVRHDIPVLP NRVGLPINQR FILVELSNHA ELSVTLALDV TNAYVVGYRA GNSAYFFHPD  120
NQEDAEAITH LFTDVQNRYT FAFGGNYDRL EQLAGNLREN IELGNGPLEE AISALYYYST  180
GGTQLPTLAR SFIICIQMIS EAARFQYIEG EMRTRIRYNR RSAPDPSVIT LENSWGRLST  240
AIQESNQGAF ASPIQLQRRN GSKFSVYDVS ILIPIIALMV YRCAPPPSSQ FSLLIRPVVP  300
NFNADVCMDP EPIVRIVGRN GLCVDVRDGR FHNGNAIQLW PCKSNTDANQ LWTLKRDNTI  360
RSNGKCLTTY GYSPGVYVMI YDCNTAATDA TRWQIWDNGT IINPRSSLVL AATSGNSGTT  420
LTVQTNIYAV SQGWLPTNNT QPFVTTIVGL YGLCLQANSG QVWIEDCSSE KAEQQWALYA  480
DGSIRPQQNR DNCLTSDSNI RETVVKILSC GPASSGQRWM FKNDGTILNL YSGLVLDVRR  540
SDPSLKQIIL YPLHGDPNQI WLPLF                                        565

SEQ ID NO: 42          moltype = AA  length = 730
FEATURE                Location/Qualifiers
source                 1..730
                       mol_type = protein
                       organism = unidentified
                       note = Galerina marginata
SEQUENCE: 42
MSSVTWAPGN YPSTRRSDHV DTYQSASKGE VPVPDPYQWL EESTDEVDKW TTAQADLAQS  60
YLDQNADIQK LAEKFRASRN YAKFSAPTLL DDGHWYWFYN RGLQSQSVLY RSKEPALPDF  120
SKGDDNVGDV FFDPNVLAAD GSAGMVLCKF SPDGKFFAYA VSHLGGDYST IYVRSTSSPL  180
SQASVAQGVD GRLSDEVKWF KFSTIIWTKD SKGFLYQRYP ARERHEGTRS DRNAMMCYHK  240
VGTTQEEDII VYQDNEHPEW IYGADTSEDG KYLYLYQFKD TSKKNLLWVA ELDEDGVKSG  300
IHWRKVVNEY AADYNIITNH GSLVYIKTNL NAPQYKVITI DLSKDEPEIR DFIPEEKDAK  360
LAQVNCANEE YFVAIYKRNV KDEIYLYSKA GVQLTRLAPD FVGAASIANR QKQTHFFLTL  420
SGFNTPGTIA RYDFTAPETQ RFSILRTTKV NELDPDDFES TQVWYESKDG TKIPMFIVRH  480
KSTKFDGTAA AIQYGYGGFA TSADPFFSPI ILTFLQTYGA IFAVPSIRGG GEFGEEWHKG  540
GRRETKVNTF DDFIAAAQFL VKNKYAAPGK VAINGASNGG LLVMGSIVRA PEGTFGAAVP  600
EGGVADLLKF HKFTGGQAWI SEYGNPSIPE EFDYIYPLSP VHNVRTDKVM PATLITVNIG  660
DGRVVPMHSF KFIATLQHNV PQNPHPLLIK IDKSWLGHGM GKPTDKNVKD AADKWGFIAR  720
ALGLELKTVE                                                        730

SEQ ID NO: 43          moltype = AA  length = 730
FEATURE                Location/Qualifiers
source                 1..730
                       mol_type = protein
                       organism = unidentified
```

```
                        note = Amanita bisporigera
SEQUENCE: 43
MPPTPWAPHS YPPTRRSDHV DVYQSASRGE VPVPDPYQWL EENSNEVDEW TTAQTAFTQG  60
YLDKNADRQK LEEKFRASKD YVKFSAPTLL DSGHWYWFYN SGVQSQAVLY RSKKPVLPDF  120
QRGTRKVGEV YFDPNVLSAD GTAIMGTCRF SPSGEYFAYA VSHLGVDYFT IYVRPTSSSL  180
SQAPEAEGGD GRLSDGVKWC KFTTITWTKD SKGFLYQRYP ARESLVAKDR DKDAMVCYHR  240
VGTTQLEDII VQQDKENPDW TYGTDASEDG KYIYLVVYKD ASKQNLLWVA EFDKDGVKPE  300
IPWRKVINEF GADYHVITNH GSLIYVKTNV NAPQYKVVTI DLSTGEPEIR DFIPEQKDAK  360
LTQVKCVNKG YFVAIYKRNV KDEIYLYSKA GDQLSRLASD FIGVASITNR EKQPHSFLTF  420
SGFNTPGTIS RYDFTAPDTQ RLSILRTTKL NGLNADDFES TQVWYKSKDG TKVPMFIVRH  480
KSTKFDGTAP AIQNGYGGFA ITADPFFSPI MLTFMQTYGA ILAVPNIRGG GEFGGEWHKA  540
GRRETKGNTF DDFIAAAQFL VKNKYAAPGK VAITGASNGG FLVCGSVVRA PEGTFGAAVS  600
EGGVADLLKF NKFTGGMAWT SEYGNPFIKE DFDFVQALSP VHNVPKDRVL PATLLMTNAG  660
DDRVVPMHSL KFVANLQYNV PQNPHPLLIR VDKSWLGHGF GKTTDKHTKD AADKWSFVAQ  720
SLGLEWKTVD                                                        730

SEQ ID NO: 44           moltype = AA  length = 734
FEATURE                 Location/Qualifiers
source                  1..734
                        mol_type = protein
                        organism = unidentified
                        note = Hypsizygus marmoreus
SEQUENCE: 44
MAISPTPWTP NTYPPTRRSS HVDIYKSATR GEVRVADPYQ WLEENTEETD KWTTAQEEFT  60
RSYLDKNTDR QRLEDAFRTS TDYAKFSSPT LYEDGRWYWF YNSGLQPQPL IYRSKGKTLP  120
DFSQDDNVVG EVFFDPNLLS DDGTAALSIY DFSDCGKYFA YGISFSGSDF STIYVRSTES  180
PLAKKNSGST DDDRLSDEIK HVKFSAVTWT KDSKGFFYQR YPAHENAKEG IETGGDVDAM  240
IYYHVIGTSQ SEDILVHSDK SNPEWMWSID ITEDGKYLIL YTMKDSSRKN LMWIAELSKN  300
EIGPNIQWNK IIDVFDAEYH LITNDGPILY VKTNADAPQY KLVTMDISGD KDISRDLIPE  360
DKNANLVQVD CVNRDTFAVI YKRNVKDEIY LYSKTGIQLS RLASDFVGAA SISSREKQPH  420
FFVTMTGFST PGTVARYDFG APEEQRWSIY RSVKVNGLNP DDFESKQVWY ESKDGTKIPM  480
FIVRHKATKF DGTAPAIQYG YGGFSISINP FFSPTILTFL QTYGAVLAVP NIRGGAEFGE  540
DWHKAGTREK KGNVFDDFVA ATQYLVKNKY AGEGKVAING GSNGGLLVGA CINRAPEGTF  600
GAAVAEVGVM DLLKFSKFTI GKAWTSDYGD PDDPKDFDFI CPLSPLHNIP TDRVLPPTML  660
LTADHDDRVV PMHSFKHAAT LQYTLPHNPH PLVIRIDKKA GHGAGKSTEK RIKESADKWG  720
FVAQSLGLVW QEPA                                                   734

SEQ ID NO: 45           moltype = AA  length = 733
FEATURE                 Location/Qualifiers
source                  1..733
                        mol_type = protein
                        organism = unidentified
                        note = Conocybe apala
SEQUENCE: 45
MPPSTPNEYP PTRRSDDVLT YRSEKNGEVV VPDPYQWLEH NTEETDKWTT AQAAFTRAHL  60
DKNPKRNALE EAFTAANDYA KFSAPQLHDD GRWYWYYNTG LQAQTCLWRT RDDTIPDFSK  120
QLDEDVGEIF FDPNALSKDG TAALSTYRFS RDGKYFAYAI AQSGSDFNTI YVRPTDSPLT  180
KRDESGRDPS RLADEVKFVK FSGITWAPNS EGFFYQRYPH IDGATLEEGG IATRRDLHAM  240
VYYHRVGTPQ SEDILIHRDP ANPEWMFGVN VTDNGEYIEL YISKDSSRKN MLWVANFAMN  300
KIGEQFQWRK VINDFAAEYD VITNHGPVYY FRTDDGAPKH KILSINIDTN ERKLLVPESE  360
DAALFSTVCV NKNYMALIYK RNVKDEVHLY TLEGKPVRRL AEDFVGACTI SGKEKQPWFF  420
VTMSGFTSPS TVGRYNFQIP EEENRWSIFR AAKIKNLNPN DFEASQVWYK SKDGTNVPMF  480
IVRHKSTQFD GTAPALQYGY GGFSISIDPF FSASILTFLK VYGAILVVPS IRGGNEFGEE  540
WHRGGMKQNK VNCFDDFIAA TNHLVEHKYA APGKVAINGG SNGGLLVAAC INRAPEGTFG  600
AAIAEVGVHD MLKFHKFTIG KAWTSDYGNP DDPHDFDYIY PISPVHNVPT DKILPPTLLL  660
TADHDDRVVP MHTFKLAATL QHTLPHNPHP LLLRVDKKAG HGAGKPLQLK IREQADKWGF  720
VAQSFQLVWR DGV                                                    733

SEQ ID NO: 46           moltype = AA  length = 730
FEATURE                 Location/Qualifiers
source                  1..730
                        mol_type = protein
                        organism = unidentified
                        note = Amanita bisporigera
SEQUENCE: 46
MPPTPWAPHS YPPTRRSDHV DVYQSASRGE VPVPDPYQWL EENSNEVDEW TTAQTAFTQG  60
YLDKNADRQK LEEKFRASKD YVKFSAPTLL DSGHWYWFYN SGVQSQAVLY RSKKPVLPDF  120
QRGTRKVGEV YFDPNVLSAD GTAIMGTCRF SPSGEYFAYA VSHLGVDYFT IYVRPTSSSL  180
SQAPEAEGGD GRLSDGVKWC KFTTITWTKD SKGFLYQRYP ARESLVAKDR DKDAMVCYHR  240
VGTTQLEDII VQQDKENPDW TYGTDASEDG KYIYLVVYKD ASKQNLLWVA EFDKDGVKPE  300
IPWRKVINEF GADYHVITNH GSLIYVKTNV NAPQYKVVTI DLSTGEPEIR DFIPEQKDAK  360
LTQVKCVNKG YFVAIYKRNV KDEIYLYSKA GDQLSRLASD FIGVASITNR EKQPHSFLTF  420
SGFNTPGTIS RYDFTAPDTQ RLSILRTTKL NGLNADDFES TQVWYKSKDG TKVPMFIVRH  480
KSTKFDGTAP AIQNGYGGFA ITADPFFSPI MLTFMQTYGA ILAVPNIRGG GEFGGEWHKA  540
GRRETKGNTF DDFIAAAQFL VKNKYAAPGK VAITGASNGG FLVCGSVVRA PEGTFGAAVS  600
EGGVADLLKF NKFTGGMAWT SEYGNPFIKE DFDFVQALSP VHNVPKDRVL PATLLMTNAG  660
DDRVVPMHSL KFVANLQYNV PQNPHPLLIR VDKSWLGHGF GKTTDKHTKD AADKWSFVAQ  720
SLGLEWKTVD                                                        730
```

-continued

```
SEQ ID NO: 47          moltype = AA  length = 738
FEATURE                Location/Qualifiers
source                 1..738
                       mol_type = protein
                       organism = unidentified
                       note = Lentinula edodes
SEQUENCE: 47
MFSATQESPT MSVPQWDPYP PVSRDETSAI TYQSKLCGSV TVRDPYSALE VPFDDSEETK  60
AFVHAQRKFA RTYLDEIPDR ETWLQTLKES WNYRRFTVPK RESDGYTYFE YNDGLQSQMS  120
LRRVKVSEED TILTESGPGG ELFFDPNLLS LDGNAALTGS MMSPCGKYWA YGVSEHGSDW  180
MTTYVRKTSS PHMPSQEKGK DPGRMDDVIR YSRFFIVYWS SDSKGFFYSR YPPEDDEGKG  240
NTPAQNCMVY YHRLGEKQEK DTLVYEDPEH PFWLWALQLS PSGRYALLTA SRDASHTQLA  300
KIADIGTSDI QNGIQWLTIH DQWQARFVII GDDDSTIYFM TNLEAKNYLV ATLDIRHSEA  360
GVKTLVAENP DALLISASIL STDKLVLVYL HNARHEIHVH DLNTGKPIRQ IFDNLIGQFS  420
LSGRRDDNDM FVFHSGFTSP GTIYRFRLNE DSNKGTLFRA VQVPGLNLSD FTTESVFYPS  480
KDGTPIHMFI TRLKDTPVDG TAPVYIYGYG GFALAMLPTF SVSTLLFCKI YRAMYVVPNI  540
RGGSEFGESW HREGMLDKKQ NVFDDFNAAT KWLVANKYAN KYNVAIRGGS NGGVLTTACA  600
NQAPELYRCV ITIGGIIDML RFPKFTFGAL WRSEYGDPED PEDFDFIYKY SPYHNIPSGD  660
VVLPAMLFFT AAYDDRVSPL HSFKHVAALQ YNFPNGPNPV LMRIDLNTGH FAGKSTQKML  720
EETADEYRCD LLCCNLQL                                                738

SEQ ID NO: 48          moltype = AA  length = 723
FEATURE                Location/Qualifiers
source                 1..723
                       mol_type = protein
                       organism = unidentified
                       note = Omphalotacae olearis
SEQUENCE: 48
MSFPGWGPYP PVERDETSAI TYSSKLHGSV TVRDPYSQLE VPFEDSEETK AFVHSQRKFA  60
RTYLDENPDR EAWLETLKKS WNYRRFSALK PESDGHYYFE YNDGLQSQLS LYRVRMGEED  120
TVLTESGPGG ELFFNPNLLS LDGNAALTGF VMSPCGNYWA YGVSEHGSDW MSIYVRKTSS  180
PHLPSQERGK DPGRMNDKIR HVRFFIVSWT SDSKGFFYSR YPPEDDEGKG NAPAMNCMVY  240
YHRIGEDQES DVLVHEDPEH PFWISSVQLT PSGRYILFAA SRDASHTQLV KIADLHENDI  300
GTNMKWKNLH DPWEARFTIV GDEGSKIYFM TNLKAKNYKV ATFDANHPDE GLTTLIAEDP  360
NAFLVSASIH AQDKLLLVYL RNASHEIHIR DLTTGKPLGR IFEDLLGQFM VSGRRQDNDI  420
FVLFSSFLSP GTVYRYTFGE EKGHSSLFRA ISIPGLNLDD FMTESVFYPS KDGTSVHMFI  480
TRPKDVLLDG TSPVLQYGYG GFSLAMLPTF SLSTLLFCKI YRAIYAIPNI RGGSEYGESW  540
HREGMLDKKQ NVFDDFNAAT EWLIANKYAS KDRIAIRGGS NGGVLTTACA NQAPGLYRCV  600
ITIEGIIDML RFPKFTFGAS WRSEYGDPED PEDFDFIFKY SPYHNIPPPG DTIMPAMLFF  660
TAAYDDRVSP LHTFKHVAAL QHNFPKGPNP CLMRIDLNSG HFAGKSTQEM LEETADEYRL  720
KVQ                                                                723

SEQ ID NO: 49          moltype = AA  length = 417
FEATURE                Location/Qualifiers
source                 1..417
                       mol_type = protein
                       organism = unidentified
                       note = Lentinula edodes
SEQUENCE: 49
METPTLNKSG SLTIVGTGIE SIGQMTLQTL SYIEAADKVF YCVIDPATEA FILTKNKDCV  60
DLYQYYDNGK SRMDTYTQMS EVMLREVRKG LDVVGVFYGH PGVFVNPSLR ALAIAKSEGF  120
KARMLPGVSA EDCLYADLCI DPSNPGCLTY EASDFLIRER PTNIYSHFIL FQVGCVGIAD  180
FNFTGFENSK FGILVDRLEK EYGAEHPVVH YIAAMLPHED PVTDQWTIGQ LREPEFYKRV  240
GGVSTFYIPP KERKEINVDI IRELKFLPEG KVPDTRTQIY PPNQWEPEVP TVPAYGSNEH  300
AAIAQLDTHT PPEQYQPLAT SKAMTDVMTK LALDPKALAE YKADHRAFAQ SVPDLTANER  360
TALEIGDSWA FRCAMKEMPI SLLDNAKQSM EEASEQGFPW IIVVGVVGVV GSVVSSA     417

SEQ ID NO: 50          moltype = AA  length = 417
FEATURE                Location/Qualifiers
source                 1..417
                       mol_type = protein
                       organism = unidentified
                       note = Omphalotacae olearis
SEQUENCE: 50
METSTQTKAG SLTIVGTGIE SIGQMTLQAL SYIEAAAKVF YCVIDPATEA FILTKNKNCV  60
DLYQYYDNGK SRLNTYTQMS ELMVREVRKG LDVVGVFYGH PGVFVNPSHR ALAIAKSEGY  120
RARMLPGVSA EDCLFADLCI DPSNPGCLTY EASDFLIRDR PVSIHSHLVL FQVGCVGIAD  180
FNFTGFDNNK FGVLVDRLEQ EYGAEHPVVH YIAAMMPHQD PVTDKYTVAQ LREPEIAKRV  240
GGVSTFYIPP KARKASNLDI IRRLELLPAG QVPDKKARIY PANQWEPDVP EVEPYRPSDQ  300
AAIAQLADHA PPEQYQPLAT SKAMSDVMTK LALDPKALAD YKADHRAFAQ SVPDLTPQER  360
AALELGDSWA IRCAMKNMPS SLLDAARESG EEASQNGFPW VIVVGVIGVI GSVMSTE     417

SEQ ID NO: 51          moltype = AA  length = 417
FEATURE                Location/Qualifiers
source                 1..417
                       mol_type = protein
                       organism = unidentified
                       note = Dendrothele bispora
SEQUENCE: 51
```

```
MESSTQTKPG SLIVVGTGIE SIGQMTLQAL SYIEAASKVF YCVIDPATEA FILTKNKNCV  60
DLYQYYDNGK SRMDTYTQMA ELMLKEVRNG LDVVGVFYGH PGVFVNPSHR ALAIARSEGY  120
QARMLPGVSA EDCLFADLCI DPSNPGCLTY EASDFLIRER PVNVHSHLIL FQVGCVGIAD  180
FNFSGFDNSK FTILVDRLEQ EYGPDHTVVH YIAAMMPHQD PVTDKFTIGQ LREPEIAKRV  240
GGVSTFYIPP KARKDINTDI IRLLEFLPAG KVPDKHTQIY PPNQWEPDVP TLPPYGQNEQ  300
AAITRLEAHA PPEEYQPLAT SKAMTDVMTK LALDPKALAE YKADHRAFAQ SVPDLTPQER  360
AALELGDSWA IRCAMKNMPS SLLEAASQSV EEASMNGFPW VIVTGIVGVI GSVVSSA     417

SEQ ID NO: 52          moltype = AA  length = 410
FEATURE                Location/Qualifiers
source                 1..410
                       mol_type = protein
                       organism = unidentified
                       note = Rhizopogon vinicolor
SEQUENCE: 52
MTTDTKRGTL TIAGSGIASI AHITLETLSY IKESDKLFYL VCDPVTEAFI QDNATGDFFD  60
LSVFYDKNKS RYDSYIQMCE IMLRAVRAGH SVLGIFYGHP GVFVSPSHRA IAVAREEGYK  120
ARMLPGVSAE DYMFADLEFD PSQSTCNTYE ATELLLRDRP LDPAIQNIIW QVGSVGVVDM  180
EFEKSKFHLL VDRLEQDFGP DHKVVHYIGA VLPQSTTTMD IFTISDLRKE NVAKQFGTIS  240
TLYIPPRDEG PVSSSMTQAF DFKAGAMVYS PVKWAGPKLN IVSALSPYER DVISQIDTHV  300
APEGYKILHT SAAMNKFMTD LSLKPKFLEE YKLYPEAVVE SAEGLSNLEK FGLKFGSDGA  360
VYILMKATES DIASGRQLTE DEIAKAHKSV GFPTVLVILP TVIVVLIGRE             410

SEQ ID NO: 53          moltype = AA  length = 413
FEATURE                Location/Qualifiers
source                 1..413
                       mol_type = protein
                       organism = unidentified
                       note = Rhizopogon vinicolor
SEQUENCE: 53
MSTKRGTLTI AGSGIASVGH ITLGTLSYIK ESDKIFYLVC DPVTEAFIYD NSTADCFDLS  60
VFYDKTKGRY DSYIQMCEVM LKAVRAGHDV LGVFYGHPGV FVSPSHRAIA VARQEGYKAK  120
MLPGISAEDY MFADLEFDPS VSGCKTCEAT EILLRDKPLD PTIQNIIWQV GSVGVVDMEF  180
SKSKFQLLVD RLEKDFGPDH KVVHYIGAVL PQSTTTMDTF TIADLRKEDV AKQFGTISTL  240
YIPPRDEGHV NLSMAKVFGG PGASVKLNDS IKWAGPKLNI VSANDPHERD VIAQVDTHVA  300
PEGHKKLRVS AAMKKFMTDL ALKPKFLEEY KLDPVAVVES AEGLSNLERF GLKFARSGPA  360
DALMKATESD IASGRQLTEE EIAQGTGPVG LQTALALLVL LGLGVAIVTR PDD         413

SEQ ID NO: 54          moltype = AA  length = 569
FEATURE                Location/Qualifiers
source                 1..569
                       mol_type = protein
                       organism = unidentified
                       note = Rhizophogun vinicolor
SEQUENCE: 54
MAKVFGLVLG FLSQTFTYPS QVWFSPVGAN NGQVITPELS NSIQETLDVW NITGLSVAII  60
PKSGEPEYHS WGDRTEDGES VTQDTLFHMA SVSKAFCVSA LGILMDDFEH GRNVTPLPPA  120
LTEFNWHTSI QDLLPGEWQL MDEWASRKAN MKDILSHVSG LPRHDFAFGP YESPKEAVSR  180
LRYLRPAFEL REQWSYNNQM FMVAGHIVET YSGKTYTSFV EDRIFTPLGM SSSTFSPAKA  240
AKTGKFTQGW TSSGRLLPEL FPEDMVMLMA GAGGVISSAV DMSKWVALWL NKGVYDNVTV  300
IPSSVYGNAS QSYAVSISTP VDSEHSIQGY GLGWFQNSYL GHNVVYHSGS IPGLSMLVSF  360
LPDDDVGFVV FANGGDKAAP VMNISNSIID AALHLRSGPA PPIMPEKKAV TSPSEDIVNL  420
ELPLEEFSGT YTDPGYGTFT FCSPSSSSSY CQQVMTDFTA VDSVHPSAPS PLQLLAAWPR  480
MGSSHIRAVH QSGNKFLLLC TALFPEGYGR DSTPFETAEI GTPGATAEFV VEDGKVVGFG  540
LFGLVDQVTE RERTQTTVKD RAEVWFDKV                                    569

SEQ ID NO: 55          moltype = AA  length = 571
FEATURE                Location/Qualifiers
source                 1..571
                       mol_type = protein
                       organism = unidentified
                       note = Rhizophogun vinicolor
SEQUENCE: 55
MIMAKVFGLV LGFLSQTFTY PSQIRLSPVG VNNGQVITPE LSNSIQETLD VWNITGLSVA  60
IIPKSGEPEY HSWGDRTEDG ESVTQDTLFH MASVSKAFCV SALGILMDDF EHGRNVTPLP  120
PALTEFNWHT SIQDLLPGEW QLMDEWASRK ANVKDILSHV SGLPSHHFAF GPYESPKEVV  180
SRLRYLRPAF ELREQWSYNN QMFTVAGHIV ETYSGKTYTS FVEDRIFTPL GMFSSTFSPA  240
KAVKTGKFTQ GWTSSGRLLP EFFQEDMIMP MAGPGGVISS AVDMSKWVAL WLNKGVHDNV  300
TIIPSSVYGN ASQSYAVSIS TPVDSEHSIL GYGLGWFRNS YLGHDVVYHS GSIPGLSTLV  360
SFLPDDDVGF VVFANGDNKA APVMNISNRI IDAALHLRSG PAPPIMPEKK AVTSPSEDIV  420
NLELPLEEFS GTYTDPGYGT FTFCSPSSSS PYCQQVIANF TTVDSVRPSA PSSLQLLAAW  480
PRVGSSHIRT VHQSGNKFML LPTALFPEGY GRDSTPFETA EIGTRGAPVE FVVEDGRVVG  540
FGLFGLVGQV TERERTQTTV KDRAGVWFDK V                                 571

SEQ ID NO: 56          moltype = AA  length = 413
FEATURE                Location/Qualifiers
source                 1..413
                       mol_type = protein
                       organism = unidentified
```

```
                        note = Rhizophogun vinicolor
SEQUENCE: 56
MSTKRGTLTI AGSGIASVGH ITLGTLSYIK ESDKIFYLVC DPVTEAFIYD NSTADCFDLS  60
VFYDKTKGRY DSYIQMCEVM LKAVRAGHDV LGVFYGHPGV FVSPSHRAIA VARQEGYKAK  120
MLPGISAEDY MFADLEFDPS VSGCKTCEAT EILLRDKPLD PTIQNIIWQV GSVGVVDMEF  180
SKSKFQLLVD RLEKDFGPDH KVVHYIGAVL PQSTTTMDTF TIADLRKEDV AKQFGTISTL  240
YIPPRDEGHV NLSMAKVFGG PGASVKLNDS IKWAGPKLNI VSANDPHERD VIAQVDTHVA  300
PEGHKKLRVS AAMKKFMTDL ALKPKFLEEY KLDPVAVVES AEGLSNLERF GLKFARSGPA  360
DALMKATESD IASGRQLTEE EIAQGTGPVG LQTALALLVL LGLGVAIVTR PDD         413

SEQ ID NO: 57           moltype = AA  length = 598
FEATURE                 Location/Qualifiers
source                  1..598
                        mol_type = protein
                        organism = unidentified
                        note = Rhizophogun vinicolor
SEQUENCE: 57
MTSDNLQPEV ISANWLKSLE AASSTGDTAS FVSHFLPDGW FRDMLCFTWN FRTLSGGQEKI  60
HGFISEVVDG QSRLSYSHLH DFKLDDHSVN APSPFKLPGP PDIEGVQGAF TFSITKPAAY  120
GRGFFRLTQD VHGNWKALTL FTNMQDLVGH EESSADEYDP HEKANPTVVI VIKVGGGQSG  180
LICAARLGKL GIRALVIDKN ARVGDIWRQR YAEALPSFAV LSRQETQVPE PYAAYSQISK  240
LLPYPSNFPK YLPKGKLANF LESYAINQEL CIWLSSTVSP SPVYDSFSAR WTVEVEHENR  300
KVILHPKHLV LATGHGRPRI PTWNGMDDFQ GTLYHSDFHR DAEKFRGKCV VVIGAGNASG  360
DICEDFVAQG AAEVTIVQRS ATCVVSSATA DAFVFKLPFS DKTPIEELDF RHNSMPLAFV  420
LQLMKSGGTQ HMKAHDKEHH EGLRKAGFNL TWEPSPGSGE VGLLGFVFER AGSGTMIDTG  480
FGKLIVEGTV KVKQGQNISH FDKEGITFKD GSKLPADVIV AATGNELTMD AIRAVLGDTI  540
AEQLPPKVWG LDAEGELNQM YRPSGHPGLW FAVGSLGMTR FCSKHLGLQI LAQEVGIA    598

SEQ ID NO: 58           moltype = AA  length = 515
FEATURE                 Location/Qualifiers
source                  1..515
                        mol_type = protein
                        organism = unidentified
                        note = Galerina marginata
SEQUENCE: 58
MGKMAYHTVL DDIALYLLGS AALVIFYRSF FYPYFLSGRR LAPGPTKGEL SKELKQFNNE  60
INVHFLRHMV KEYGPIFRLV GAPMIPGPGL VVCTPTAQQR ILVSNSINYG QPRLAFFRWV  120
TGGLFTLPER EHRGMRKILD PVFSFRNLIS TTGVYYNTVQ SLITIFRSKI DGENGAKDGD  180
VILVYEWLAR LAIDNVSEAI LGFKLDTLHD PNNELITTLD ELSRIPTAAF ELLVRVPGFL  240
RLVTFDSVRH STLWQRRVPG RLGVFFTFMR CLSTIRKNAL AIKATILQED SANRDLNVIS  300
VLQHMQSSDE TANADIAGNI IMLWMSGRAT IATRISWLLW LLAKDQQCQQ QLRDEIAPLF  360
SRDPRPDYRS LDKLQWLDSV IMESIRLFLF GPNIRVALND DYIDGVFVPK GTVVVIPLDL  420
FTRGDIWGED PDQFKPARWL DSTKRYKISP PFLSFLTGPH RCIAKGMAIM QTKIVIASLI  480
ANFEFKPAYE GQHVEGNPSI IGHGMPLHVK PIRPS                             515

SEQ ID NO: 59           moltype = AA  length = 1318
FEATURE                 Location/Qualifiers
source                  1..1318
                        mol_type = protein
                        organism = unidentified
                        note = Galerina marginata
SEQUENCE: 59
MPYVPDPKYF EHREQSSGAT LYYCLVCRDG RERQPHHIKT HEASQAHRTA LSVFDSQAES  60
SSQQTHGNPT QPGYFDPVID DAVRALLVSG SGDPHQPLYP AGHPNVYGEP NFTDSRRRTS  120
PVTGIDWDQF EAQEDTHAVP SAQDQLRADI CQATLDWLND DISDDDEREP SEVDSVDSDA  180
ESDREPIPDD QPRKRARTNR DNPISEDWYP WQDKITCTLD ILMHLPRSVF SRKQLDLFLW  240
LLRVNNVDDV PTGKSMKMLN KILQGMCGIE TIAYEGKLGH NYHVNNIAQI LAQELCNPKV  300
GPHIYFYPED SGDNLAEARQ AARWLHELRP EETTPMIHLP SGDYYIYEPA MLSNRSFCIP  360
FRWFTRNGKF HARAWSLETG VVDNTLGWIV HKENEVEISE DDLLKDFTRF SSDCEAYNVP  420
HPSRILGVSC ADSGNLLPWN HTNPVLGNRW RQLAKGHRTL CLPLWMYCDD TSGNTSKKWN  480
EHNSFLFTLA GLPREHTAKE YNIHFLCTSN LAPPLEMMDG VVSQIEAAQQ NGIWAWDCVR  540
KEPVLIFPTI LALLGDNPMH SEFACHIGLR GKFFCRTCWV KGSDAQDDAN IVTPGLHETP  600
ENSPAPSPAP SPAPSPAPSP APSPALSMAP QSQPPTPSEP SMQVPAPPST AAPTKARGKK  660
KETMSAMLNR ITAFIKPGRL RNKSETQKTL QNFKEQAQTI GAKTKLKTAR TETGIKDTVQ  720
EFFFEKLFSS YKNKRGPQAK QEALDQAVNQ LPSDITSPVW RLKGLDPHQD TPVEILHVVL  780
LGFIKYFWRD LVQNQINDDQ KQTLIQRLNS FDVTGLGITQ LGGETLVNYA GSLTGRDFRA  840
VAQVAPFVIY DMVPADVFDA WLALSKLVPL VWQPYIENVA QYLTTLEHEI HVFLLRTARW  900
TTGWFNKSKF HIILHLPSHI RRFGPAILFA TEAFESFNAV IRAKSVHSNR QAPSRDIALA  960
FAQGNRIRHL LSGGHFLSAD THMVVDPDQP QLGQYERLAR GRWRSVGPGP GHLVSAEPIL  1020
PSYLGIPPQS TTSSAGLCKR TKTPPQTFLQ TLTGLKLPNV SRPGARELWQ TCSEVYLLND  1080
DKCLIGHHVI VQRQSEQASF VSPPFIARIG EILQKVGSAN HAHDKPDGIL VQTLKSSEVA  1140
DKFQMPRLVP QNEWSFVPLA DILCTVNAQH DCDRNGCTAS GFRYVYQERI QTNDQRPVVE  1200
HVNQPEDFIL NTAQMRDALH LQKFRIRSRS LDEQTIIHES VARTINQRKA QDNSSSGTGG  1260
AGVSGRGRGR GRGRGGGVEG PSTSRGRGGG IEGRGASSSS GNGRGRGRGA RSAQSVPF    1318

SEQ ID NO: 60           moltype = AA  length = 1262
FEATURE                 Location/Qualifiers
source                  1..1262
                        mol_type = protein
```

```
                         organism = unidentified
                         note = Galerina marginata
SEQUENCE: 60
MPRKKPAPEC FETDEASKMI RCLICKENDT VQQGTWIKHG SASQHIETNA HKLAVARREQ  60
LLQVQQEEER RLQEIYGGNT IPLSGNAQLY PTYPRANMYG NQDAVDTDMD NQNSPPQAYM  120
LCDADIPDLG IKPIERPDPS QERERLRQQV EQLLLQAEHE DEFGSPDDPD DLTSTNIAQA  180
FADLDLEEML DEEEVFDYFN QVSPEHDYYP YPNKTTMLLD ILDNLPRLRM SSNQLRLILW  240
LLKQTGVSNV PSFSGFRNMQ THLRNMCGTT PKQHVSSLGN IFYSNNIGES VMRDFANPEV  300
AKHLHLYPEE TEGPISEVWQ AERWKEFAPS ELTPMFSQGH RQFFIDEVAQ LQDGQYVIPR  360
NWVMRKGKLT SDCHIVTVNP VRFSKLHGSL VLVLKQCFQS GWTLLSETQI FHADDFQFNY  420
FDVVSRIRGP ISWSEGTEVP AMPNNLRELA GDDDLVVIMV PLWCDDVSGN KSKQYNKHIN  480
VYMANSNIPG RLLQQEYFVR FVSTSPNATS PEQFSALKDQ INETQKKPIQ CYNAHTNKKT  540
RAILRVPGLP ADNPQQSEES CHMGGNANCK CRKCHVGGPH EKKESNEGYH EHYLTGIKRS  600
AEETRLELEK QIKLAMYGVE KPINETQTNT GTKDKVAQHW IDILLAKSRE LKSANPSRSV  660
EEIAQELQTW FDEQPGDKIN PLLSIAGLDP TQDTPVEILH TILLGIVKYA WHHLHSNWTE  720
AEQNLFTVRL QSTDIDGLSV PPIRVAYMMQ YRNGLIGKHF KTLMQTLPFH VHGTVSDAQF  780
KLVKAIGELG SVLWVHEIGD MEKYLSDLEI LIGNVLDAFA EIDPSTAMYA RFIYEPMPVP  840
SKIIVKLKLH MLPHLIEDIK RFGPAIRNST EVFECFNAIF RLCSILSNHQ AASRDIALKF  900
ASMDRLKHML SGGYWLSEVE EGKFEWIRAG ENVRNILQSE PTIQRHLGWA PSAKFQSGRK  960
RTPPTSWENT KASQFMDSEE TAAIGFPNPR LLSWRKGVTT TAQSGDRCST GSWVVARNHK  1020
VCYILASHYC SIAKNDQGES CIGRIHEIIG PDEKSASSTG IITLECFQLG KEHHPDFGLP  1080
TLQRPQADLP KYILKAWQDP LFIFSAHHDC HTASCQATAL QPQLQERQLT SRMNKLIAHN  1140
DSDHFIINLY GLHNAILLRE FLPRELTAPQ PLHQDRKAFH YEVAAKLRVQ QAEKRAKTNA  1200
RRKATRAANK AKQVERQKQN PDHEQESEQE MDERPNSENG SDIELGGDDD IEVETRRKRR  1260
RN                                                                1262

SEQ ID NO: 61            moltype = AA  length = 1206
FEATURE                  Location/Qualifiers
source                   1..1206
                         mol_type = protein
                         organism = unidentified
                         note = Hypsizygus marmoreus
SEQUENCE: 61
MGRRAEELPA YVELSEDGTL VRCNLCLMHN RLDYSKEWIQ RKGWRSHKGS GIHDRSEAKQ  60
RVLDDAAMDL QEPASAEVEV VTFNDILIIN APKTPTGNMQ SEEQAMWDHF DAGSFTLEAG  120
EDPNHSSQRL YQDLARKADA YGAWDGTEAL PEYRDLDDVS QFLDEDEEED LLSEILRGLG  180
LEEEHEDSSD RNPAEELNSP WYPYGSKLMF LLDTIDNLPR LRISGAMMRV FLWLLREVGV  240
RQVPSFDKLR KIQRKLREGS GVPTVHWMSP KGNAYSFNDP AVIVANDWAS PITRPHLRRY  300
PVIPKDGVIT EVYHAEKWHR EINRHFLTPM YDDGFRHYFI DELAQLKDGR YAVPVRWLED  360
VDGRIVADAW RVELEDDNRA TIIDTATVRI HSQELALNFE EIIESNLMPE WSDTTTEAGH  420
PSRMPNPDRA LAEGDPIYTS FIDIFGDDVS GNRSKSWNKH WNMYISHRNL PRKLLHQQYH  480
THFVSTSTFA SIPEQFVGVK EAIESTHSKP VKVRDADTGK QIRLKIYCNC GPGDNPSQSE  540
TSGHIGGNGN YPCRKCHTGG TQKSKETDEG FYKMFTAGEA RSSKETLAEV KSQVEAACTG  600
VAKTVADAQS DTGVKDAYTQ YWIDAIIEKA RAMQKENPGM PTTTIQATLI KWVYDHEEAI  660
YNSFLTLDGF DASRDTPVEI LHTILLGIVK YLWHRSHTSW NAAQKKIYST RLQGTNTQGL  720
SIHHIRANYI MQYANSLIGR QLKTLAQVNV FHVYDLVDPL RFLFTKATGE LCALLWFTEI  780
RDLEEYLSDV DIAAANVLDI AAVIDPSKIV SKIKYHLLSH LREDIIRFGP LVGVATEVFE  840
CFNAVFRYCS ILSNHLAPSR DIAYKLAAQE TMKHFLSGGW WHVKDSVDLQ GNPKWVQPGP  900
SVRTFMASNP VLHTLCGWTR NNDSTPGTVK SEPRKRGPDK QTLLPLVRLA WLETQGSRAL  960
NNTSPNNETQ WQRCKYVIAE TQDQCNVGSW VFARSPLLEN IPIPGRIVEI LQDTSASPSA  1020
FVVIDVFQVS ATRDEVFGMP VLLRRFNECC LHVIPASSVI FDFNAQHDCR YAKCEATGEQ  1080
PLIQERVPSG VTENFVVHKA IDRYLINIHA LHNAHLIRAT LPRDLTAPIP YAPNREAHHS  1140
AIAAELRSAQ DTKRAKTAAK TAANAAAKKA EAALKDTTSG PAAKRRRVDD EGSGEEDNRD  1200
VDMVSV                                                            1206

SEQ ID NO: 62            moltype = AA  length = 1213
FEATURE                  Location/Qualifiers
source                   1..1213
                         mol_type = protein
                         organism = unidentified
                         note = Galerina marginata
SEQUENCE: 62
MAKGRKLNNP LPDFIEISND GLQVRCTLCL AARQHNGSGW IKRGSVSNHL KSDNHTNSLE  60
AHEMKKSAEK AEGRSVQEEI AMEEGMDFVI LSSKIQPEIT APARAPRRSN EEQEMWDRYT  120
LGGEVFDAGV DHTLVEAEER KRLEREATDF DLWHGADFLP EEDPNDGELL LDELEQDDIL  180
SELLRNAHLN APDAADVLTE EPRAAADPRI CDAWSPYESK MMFLLDTLDN LPRLRISNSL  240
MNVFLWILRE GGARDVPSLY HLRQVQTTLR KSTGVPTTQH KSPKGNVYSM NDPRTLVAMD  300
WANPVICDHI RRYPVIPRNG VISEVYHAQK WRKDVDPHTL SPMYDAGNCH YYIDEVARLK  360
NGTFIIPVRW LEDEDRNVCA DAYVVQFDDQ FIASVVDGET IIVQASDLQN NFLDLKDMGL  420
LPTWGNQTIE SGHPARMPNP DRALAEGDPL YTSWIDVFGD DVSGNRSKNW NKHWNIYISH  480
RNLPRKLLQQ EFHTHFVSTS PVASVTEQFH GIKQVIELTH KSPVKVRHGT SGAQIRFKIN  540
VNCGPGDNPA QSEVCGHIGV NGNKLCRKCH TGGTHEVKES DEGFNSLFEP GDARSAQEIV  600
ADVESQVQLA CLGIAQHVQN QQTKNGIKDA YTQYWIDYLI NRARTLRKEQ PRRTTADIQS  660
ELLVWVQEHK DEIYNPFLKL DGFDAAVDTP VEILHTILLG IVKYLWHGSH TSWTAIQKQT  720
YSVRLQSTDT SGLSIHAIRA NYIMQYANSL IGRQFKTIAQ VNVFHVYDLV DTTQFLLTKA  780
VGELTALLWI PEIANMEEYL LDVEAAAANV LDLFALIDPS KMTNKLKLHL LVHLKADILR  840
FGPLVGVATE TFECFNAIFR FCSIYSNHLA PSRDIAFQLA SQEVLKYRLT GGWWPASDGE  900
WKRPGPSVRN FIHDHPTLQA LLGWTKEEKL VNGSFRLEPL KRDASQKIES RKHLPWLQTQ  960
GAKAVNSSED NDSKWTACRF AVANSGDKCS VGSWVFATSP FNSNQSVTGR IVEVLAESEG  1020
```

-continued

```
KRAVVVLDIF EVCSTRHKIF GMPMLARRHE EPVYAVIAST NIEFLYNVQH DCPLAKCTAS  1080
GKQPLIQERV ESGLFKTYIE HKPIERFVIN THAFHNAHRL RAVLQRSLVV PIPLYPPEIR  1140
KTKHAEFAHN LQATQKVKLE ARAAQKAKEI ITPADKTDST IPKKRTRSEM ETETDDTAIA  1200
TQADVFFNAQ GCP                                                    1213

SEQ ID NO: 63          moltype = AA  length = 517
FEATURE                Location/Qualifiers
source                 1..517
                       mol_type = protein
                       organism = unidentified
                       note = Galerina marginata
SEQUENCE: 63
MVQIKRLLLG FLSSPSQTPL ESNHGPVPSK SIAVVGAGSA GLAMLRTLVE LEAFSRNNWE  60
VVLYEERESV GGIWLPDNND VFPPEIPKTP LYPLLRTNTP VPSMTYPGFP FPPSTPLYPR  120
HDHVEAYHLR YARRHNLLDF IKFDTMVEKA FWNGTPEEGY WNLTLSSKEG RMRYKTFDHL  180
VVATGNNHIP HIPVWKGQED WLASPANHSR KIIHSVYYRG PEAFSNQTVL IVGNGGSGRD  240
AATQILGYAS QTFMSIRRSY GPVDDGVIVK PDISHFTEAG VVFVDGTILD PDVILLGTGY  300
EMQKPLLSEG GELSFDPTAK DNSSVRGTLV TNGHYIFPLH RHIFSLSPRY PPNALAFIGL  360
LSFIASCPSD IAQSLFAAHA ILDPSILPPR HLLLEELASY EDKARRQGLD PYLKGPIMLN  420
NTSNDYQDEL VEYLKQKNAI PDDGKKFVEE WRREILAYHY LQRGWSRIEK LGMGPAWTEG  480
VKTEAQWFDL MTRVNEWQKN WETENGIAFR VDLDLTG                          517
```